(12) United States Patent
Lin et al.

(10) Patent No.: US 11,046,933 B2
(45) Date of Patent: *Jun. 29, 2021

(54) INDUCTION OF PLURIPOTENT CELLS

(71) Applicant: The Scripps Research Institute, La Jolla, CA (US)

(72) Inventors: Tongxiang Lin, San Diego, CA (US); Sheng Ding, Orinda, CA (US)

(73) Assignee: The Scripps Research Institute, La Jolla, CA (US)

( * ) Notice: Subject to any disclaimer, the term of this patent is extended or adjusted under 35 U.S.C. 154(b) by 465 days.

This patent is subject to a terminal disclaimer.

(21) Appl. No.: 15/875,928

(22) Filed: Jan. 19, 2018

(65) Prior Publication Data
US 2018/0163181 A1 Jun. 14, 2018

Related U.S. Application Data

(63) Continuation of application No. 14/637,089, filed on Mar. 3, 2015, now Pat. No. 9,909,105, which is a continuation of application No. 13/500,373, filed as application No. PCT/US2010/052896 on Oct. 15, 2010, now Pat. No. 9,005,968.

(60) Provisional application No. 61/252,548, filed on Oct. 16, 2009.

(51) Int. Cl.
C12N 5/074 (2010.01)

(52) U.S. Cl.
CPC ...... C12N 5/0696 (2013.01); *C12N 2501/065* (2013.01); *C12N 2501/602* (2013.01); *C12N 2501/603* (2013.01); *C12N 2501/604* (2013.01); *C12N 2501/606* (2013.01); *C12N 2501/727* (2013.01); *C12N 2501/999* (2013.01); *C12N 2506/094* (2013.01); *C12N 2506/1307* (2013.01); *C12N 2506/28* (2013.01); *C12N 2510/00* (2013.01)

(58) Field of Classification Search
CPC ............ C12N 5/0695; C12N 2501/999; C12N 2501/602; C12N 2501/604; C12N 2501/606; C12N 2501/603; C12N 2501/727

See application file for complete search history.

(56) References Cited

U.S. PATENT DOCUMENTS

| | | | |
|---|---|---|---|
| 5,824,837 A | 10/1998 | Chen et al. | |
| 5,843,780 A | 12/1998 | Thomson | |
| 6,200,806 B1 | 3/2001 | Thomson | |
| 7,029,913 B2 | 4/2006 | Thomson | |
| 7,265,138 B2 | 9/2007 | Doherty et al. | |
| 8,298,825 B1 | 10/2012 | Hochedlinger et al. | |
| 8,603,818 B1 | 12/2013 | Hochedlinger et al. | |
| 8,906,677 B2 | 12/2014 | Li et al. | |
| 9,005,968 B2 | 4/2015 | Lin et al. | |
| 9,905,105 B1 | 3/2018 | Lin et al. | |
| 2002/0142457 A1 | 10/2002 | Umezawa et al. | |
| 2004/0157324 A1 | 8/2004 | Spradling et al. | |
| 2006/0182724 A1 | 8/2006 | Riordan | |
| 2007/0032447 A1 | 2/2007 | Eilertsen | |
| 2007/0128719 A1 | 6/2007 | Tseng et al. | |
| 2007/0134215 A1 | 6/2007 | Fukuda et al. | |
| 2007/0141703 A1 | 6/2007 | Stanley et al. | |
| 2007/0161107 A1 | 7/2007 | Mummery et al. | |
| 2007/0172946 A1 | 7/2007 | Smith et al. | |
| 2007/0196919 A1 | 8/2007 | Reh et al. | |
| 2007/0254359 A1 | 11/2007 | Rezania et al. | |
| 2007/0259423 A1 | 11/2007 | Odorico et al. | |
| 2007/0264709 A1 | 11/2007 | Smith et al. | |
| 2007/0269412 A1 | 11/2007 | Kopyov | |
| 2007/0281355 A1 | 12/2007 | Dalton et al. | |
| 2008/0066197 A1 | 3/2008 | Ying et al. | |
| 2008/0242594 A1 | 10/2008 | McKay et al. | |
| 2008/0268533 A1 | 10/2008 | Dalton et al. | |
| 2009/0068742 A1 | 3/2009 | Yamanaka | |
| 2009/0117439 A1 | 5/2009 | Fujinami et al. | |
| 2009/0203690 A1 | 8/2009 | Akritopoulou-Zanze et al. | |
| 2009/0227032 A1 | 9/2009 | Yamanaka et al. | |
| 2010/0233804 A1 | 9/2010 | Zhou et al. | |
| 2010/0267141 A1 | 10/2010 | Shi et al. | |
| 2011/0033931 A1 | 2/2011 | Schwartz et al. | |
| 2011/0039332 A1 | 2/2011 | Sakurada et al. | |
| 2012/0122212 A1 | 5/2012 | Grskovic et al. | |
| 2012/0129172 A1 | 5/2012 | Okano et al. | |
| 2012/0196360 A1 | 8/2012 | Okita et al. | |
| 2013/0323833 A1 | 12/2013 | Zhu et al. | |

(Continued)

FOREIGN PATENT DOCUMENTS

| | | |
|---|---|---|
| CN | 101356270 A1 | 1/2009 |
| EP | 1970446 A1 | 9/2008 |

(Continued)

OTHER PUBLICATIONS

Aasen et al., Nat Biotechnol 26:1276-1284 (2008).
Aoi et al., "Generation of Pluripotent Stem Cells from Adult Mouse Liver and Stomach Cells," Sciencexpress, Feb. 2008, DOI 10.1126/science.1154884, 8 pages.
Artyomov et al., PLoS Comput Biol 6, e1000785 (2010).
Beaujean et al., Dev. Biol., 2000, vol. 221, pp. 337-354.
Brambrink et al., Cell Stem Cell 2, 151-9 (2008).
Brons et al., Nature, 2007, vol. 448, pp. 191-195.
Chambers et al., Nature, 2007, vol. 450, pp. 1230-1234.

(Continued)

*Primary Examiner* — Marcia S Noble
(74) *Attorney, Agent, or Firm* — Kilpatrick Townsend & Stockton LLP

(57) ABSTRACT

The slow kinetics and low efficiency of reprogramming methods to generate human induced pluripotent stem cells (iPSCs) impose major limitations on their utility in biomedical applications. Here we describe a chemical approach that dramatically improves (>200 fold) the efficiency of iPSC generation from human fibroblasts, within seven days of treatment. This will provide a basis for developing safer, more efficient, non-viral methods for reprogramming human somatic cells.

6 Claims, 24 Drawing Sheets

Specification includes a Sequence Listing.

(56) References Cited

U.S. PATENT DOCUMENTS

| | | | |
|---|---|---|---|
| 2015/0079675 | A1 | 3/2015 | Li et al. |
| 2015/0240214 | A1 | 8/2015 | Lin et al. |

FOREIGN PATENT DOCUMENTS

| | | | |
|---|---|---|---|
| GB | 2 436 737 | | 10/2007 |
| GB | 2 450 603 | A | 12/2008 |
| JP | 2007/508026 | | 4/2007 |
| JP | 2008099662 | | 5/2008 |
| JP | 2009-215191 | A | 9/2009 |
| JP | 2008/307007 | | 6/2010 |
| JP | 2012510526 | | 5/2012 |
| WO | 03/095628 | A2 | 11/2003 |
| WO | 09/032456 | A1 | 3/2006 |
| WO | 2007/016566 | A2 | 2/2007 |
| WO | 2007/069666 | | 6/2007 |
| WO | 2007/113505 | | 10/2007 |
| WO | 2008/015418 | A2 | 2/2008 |
| WO | 2008035110 | | 3/2008 |
| WO | 2008/056173 | A2 | 5/2008 |
| WO | 2008/088882 | | 7/2008 |
| WO | 2008/089351 | | 7/2008 |
| WO | 08/105630 | A1 | 9/2008 |
| WO | 2009/006422 | A1 | 1/2009 |
| WO | 2009007852 | | 1/2009 |
| WO | 2009/032194 | A1 | 3/2009 |
| WO | 2009/057831 | | 5/2009 |
| WO | 2009061442 | | 5/2009 |
| WO | 09/067756 | A1 | 6/2009 |
| WO | 09/067757 | A1 | 6/2009 |
| WO | 09/073523 | A2 | 6/2009 |
| WO | 2009/117439 | A1 | 9/2009 |
| WO | 2010/065721 | A1 | 6/2010 |
| WO | 2011/047300 | A1 | 4/2011 |
| WO | 2011/109695 | A1 | 9/2011 |

OTHER PUBLICATIONS

Chen et al., "Self-renewal of embryonic stem cells by a small molecule," PNAS, 103(46):17266-17271, 2006.
Chen et al., Proc Natl Acad Sci USA, 2007, vol. 104, pp. 10482-10487.
Chou et al., Cell, 2008, vol. 135, pp. 449-461.
Christen et al., BMC Biol 8, 5 (2010).
Claassen et al., "ROCK inhibition enhances the recovery and growth of cryopreserved human embryonic stem cells and human induced pluripotent stem cells," Molecular Reproduction and Developments, 2009, vol. 76, No. 8, pp. 722-732.
Collas et al., Reproductive BioMedicine Online: 762-770, 2006.
D'Amour et al., Nat Biotechnol, 2005, vol. 23, pp. 1534-1541.
Debs et al., J. Biol. Chem., 1990, vol. 265, pp. 10189-10192.
Demers et al., Cloning Stem Cells, 2007, vol. 9, pp. 512-522.
Dimos et al., Science, 2008, vol. 321, pp. 1218-1221.
Djuric et al., 202, Stem Cell Research and Therapy, 2010, 1:3.
Dvorak et al., Stem Cells, 2005, vol. 23, pp. 1200-1211.
Ernst et al., "gp130-mediated Signal Transduction in Embryonic Stem Cells Involves Activation of Jak and Ras/Mitogen-activated Protein Kinase Pathways," J. Biol. Chem., Nov. 22, 1996, vol. 271, No. 47, pp. 30163-30143.
Feldman et al., "G9a-mediated irreversible epigenetic inactivation of Oct-3/4 during early embryogenesis," Nature Cell Biology, 2006, vol. 8(2), pp. 188-194.
Feng et al, "Molecules that Promote or Enhance Reprogramming of Somatic Cells to Induced Pluripotent Stem Cells," Cell Stem Cell, 2009, 4, 301-12.
Graf et al., Nature 462(7273):587-594 (2009).
Guo et al., Development, 2009, vol. 136, pp. 1063-1069.
Han et al., Curr Stem Cell Res Ther, 2008, vol. 3, pp. 66-74.
Han et al., Nat Cell Biol 13(1):66-71 (2011).
Hanna et al., Cell 133, 250-64.
Hanna et al., Nature 462, 595-601 (2009).

Hanna et al, "Treatment of Sickle Cell Anemia Mouse Model with iPS Cells Generated from Autologous Skin," Science, Dec. 21, 2007, vol. 318, pp. 1920-1922.
Hayashi et al., Cell Stem Cell, 2008, vol. 3, pp. 391-401.
Hindie et al., Structure and allosteric effects of low-molecular-weight activators on the protein kinase PDK1, Nat. Chem Biol., Oct. 2009, vol. 5, No. 10, pp. 758-764.
Ho et al., Cancer Res., 2001, vol. 61, pp. 474-477.
Hochedlinger et al., Development 136, 509-23 (2009).
Hochedlinger, et al., "Nuclear reprogramming and pluripotency," Nature, Jun. 2006, vol. 441, pp. 1061-1067.
Huangfu et al., Induction of pluripotent stem cells by defined factors is greatly improved by small-molecule compounds, Nature Biotechnology, 2008, vol. 26, pp. 795-797.
Huangfu et al., "Induction of pluripotent stem cells from primary human fibroblasts with only Oct4 and Sox2," 2008, Nature Biotechnology, 26:11, pp. 1269-1275.
Hudecz et al., Medicinal Research Reviews, 25(6): 679-736, 2005.
Ieda et al., Cell 142, 375-86 (2010).
Jia et al., Nat Methods 7(3):197-199 (2010).
Kanatsu-Shinohara et al., Cell, 2004, vol. 119, pp. 1001-1012.
Kim et al., Cell, 2009, vol. 136, pp. 411-419.
Kim et al., Cell Stem Cell, 4(6):472-476, 2009.
Kim et al., "Direct reprogramming of mouse fibroblasts to neural progenitors," Proc. Natl. Acad. Sci., USA, May 10, 2011, vol. 108, No. 9, pp. 7838-7843.
Krippl et al., Proc. Natl. Acad. Sci. USA, 1984, vol. 81, pp. 6988-6992.
Kubicek, et al., "Reversal of H3K9me2 by a Small-Molecule Inhibitor for the G9a Histone Methyltransferase," Molecular Cell, Feb. 2007, vol. 25, No. 3, pp. 473-481.
Kuzmenkin et al., FASEB J. 23, 4168-80 (2009).
Li et al., "Generation of rat and human induced pluripotent stem cells by combining genetic reprogramming and chemical inhibitors," Cell Stem Cell, 2009, vol. 4, pp. 16-19.
Li et al., Differentiation, 2007, vol. 75, pp. 299-307.
Li et al., "Small molecules that modulate embryonic stem cell fate and somatic cell reprogramming," Trends Pharmacol Sci, Jan. 2010, vol. 31, No. 1, pp. 36-45.
Li et al., "Generation of Human-Induced Pluripotent Stem Cells in the Absence of Exogenous Sox2," Stem Cells 27:2992-3000 (2009).
Lin et al., Nat Methods 6:805-808 (2009).
Lin et al., Nat Methods 6:805-808 (2009), Supplemental Information, 7 pages.
Lowry et al., Proc Natl Acad Sci USA, 2008, vol. 105, pp. 2883-2888.
Maherali et al., "Directly Reprogrammed Fibroblasts Show Global Epigenetic Remodeling and Widespread Tissue Contribution," Cell Stem Cell, 2007, 1, pp. 55-70.
Maherali et al., "Tgfβ Signal Inhibition Cooperates in the Induction of iPSCs and Replaces Sox2 and cMyc," Current Biology, 2009, vol. 19, pp. 1718-1723.
Meissner, et al., "Direct reprogramming of genetically unmodified fibroblasts into pluripotent stem cells," Nature Biotechnology, Oct. 2007, vol. 25, No. 10, pp. 1177-1181.
Mi et al., Mol. Ther., 2001, vol. 4, pp. 339-347.
Mikkelsen et al., Nature 454(7200):49-55 (2008).
Muller et al., "Upping the Ante: Recent Advances in Direct Reprogramming," Mol. Ther., 2009, vol. 17, pp. 947-953.
Nakagawa et al., Nat Biotechnol, 2008, vol. 26, pp. 101-106.
Noggle et al., "A Molecular Basis for Human Embryonic Stem Cell Pluripotency," Stem Cell Reviews and Reports, Jan. 2005, vol. 1(2), pp. 1550-8943; DOI: 10.1385/scr:1:2:111.
Okada et al., Biochem Biophys Acta 1800, 956-63 (2010).
Okita et al., Nature 448, 313-317 (2007).
Okita et al., Science 322:949-953, 2008.
Oliveri et al., Regenerative Medicine, 2(5): 795-816, Sep. 2007.
Pan et al., J. Biol. Chem., 2004, vol. 279, pp. 37013-37020.
Peerani et al., EMBO J., 2007, vol. 26, pp. 4744-4755.
Plath et al., Nature Reviews, 12: 253-265, 2011.
Plews, et al., "Activation of Pluripotency Genes in Human Fibroblast Cells by a Novel mRNA Based Approach," PLoS ONE, Dec. 2010, vol. 5, No. 12, pp. 1-10.

(56) References Cited

OTHER PUBLICATIONS

Roberts et al., (PD98059 Enhanced Insulin, Cytokine, and Growth Factor Activation of Xanthine Oxidoreductase in Epithelial Cells Involves STAT3 and the Glucocoticoid Receptor, Journal of Cellular Biochemistry 2007, 101: 1567-1587.
Ruhnke et al., Stem Cells, 2003, vol. 21, pp. 428-436.
Saha et al., Biophys. J., 2008, vol. 94, pp. 4123-4133.
Sato et al., Dev. Biol., 2003, vol. 260, pp. 404-413.
Schenke-Layland et al., Stem Cell 26, 1537-46 (2008).
Schugar et al., Gene Ther, 2008, vol. 15, pp. 126-135.
Schulze et al., Methods Mol Biol, 2006, vol. 329, pp. 45-58.
Sells et al., BioTechniques, 1995, vol. 19, pp. 72-78.
Shi, et al., "A Combined Chemical and Genetic Approach for the Generation of Induced Pluripotent Stem Cells," Cell Stem Cell, Jun. 2008, vol. 2, No. 6, pp. 525-528.
Shi "Induction of Pluripotent Stem Cells from Mouse Embryonic Fibroblasts by Oct4 and Klf4 with Small-Molecule Compounds," Cell Stem Cell, 2008, vol. 3, pp. 568-574.
Shields et al., J. Biol. Chem., 1997, vol. 272, pp. 18504-18507.
Silva et al., Cell 138, 722-37 (2009).
Silva et al., PLoS Biology, 6(10): 2237-2247, Oct. 2008.
Singh et al., Stem Cells, 2007, vol. 25, pp. 2534-2542.
Sridharan et al., Cell 136(2):364-377 (2009).
Stacey et al., Mol. Cell. Biol., 1987, vol. 7, pp. 523-527.
Stadtfeld et al., "Reprogramming of Pancreatic β Cells into Pluripotent Stem Cells," Curr. Biol., Jun. 2008, vol. 18(12): 890, doi: 10.1016/j.cub.2008.05.010.
Stadtfeld et al., Cell Stem Cell 2, 230-40 (2008).
Stadtfeld et al., Nat Methods 7, 53-55 (2010).
Stadtfeld et al., Science 322:945-949, 2008.
Sullivan et al., Reproductive BioMed. Online, 16(1): 41-50, Nov. 2008.
Sylvester et al. (Arch Surg. 136:93-99, 2004).
Szabo et al., Nature 468(7323):521-526 (2010).
Tada, et al., "Nuclear reprogramming of somatic cells by in vitro hybridization with ES cells," Current Biology, 2001, vol. 11, pp. 1553-1558.
Takahashi, et al., "Induction of Pluripotent Stem Cells from Mouse Embryonic and Adult Fibroblast Cultures by Defined Factors," Cell, Aug. 2006, vol. 126, No. 4, pp. 663-676.
Takahashi et al.; "Induction of Pluripotent Stem Cells from Adult Human Fobroblasts by Defined Factors"; Cell, 2007, vol. 131, pp. 861-872.
Takahashi et al., Nat Protoc 2, 3081-9 (2007).
Taranger et al., "Induction of Dedifferentiation, Genomewide Transcriptional Programming, and Epigenetic Reprogramming by Extracts of Carcinoma and Embryonic Stem Cells," Molecular Biology of the Cell, 2005, vol. 16, pp. 5719-5735.
Tesar et al., Nature, 2007, vol. 448, pp. 196-199.
Tighe et al., BMC 8:34 doi//:www.biomedcentral.com/1471-2121/8/34, printout pp. 1-17.
Tojo, et al., "The ALK-5 inhibitor A-83-01 inhibits Smad signaling and epithelia-to-mesenchymal transition by transforming growth factor-β," Cancer Sci, Nov. 2005, vol. 96, No. 11, pp. 791-800.
Toyooka et al., Development, 2008, vol. 135, pp. 909-918.
Ueda et al., PLoS ONE 3, 2008, e2800.
Vallier et al., "Activin/Nodal and FGF pathways cooperate to maintain pluripotency of human embryonic stem cells," Journal of Cell Science, Oct. 2005, vol. 118(19), pp. 4495-4509, DOI: 10.1111/J.1432-0436.2006.00143.X.
Vierbuchen et al., "Direct conversion of fibroblasts to functional neurons by defined factors," Nature, Feb. 25, 2010, vol. 463, No. 7284, pp. 1035-1042.
Wadia et al., Curr. Opin. Biotechnol., 2002, vol. 13, pp. 52-56.
Warren et al., Cell Stem Cell 7(5):618-630 (2010).
Watanabe et al., "A Rock inhibitor permits survival of dissociated human embryonic stem cells," Nature Biotechnology, 25(6):681-868, 2007.
Wenlin et al., "Generation of novel rat and human pluripotent stem cells by reprogramming and chemical approaches," Methods in Molecular Biology, Jan. 2010, vol. 636, pp. 293-300.
Wernig et al., Nat Biotechnol 26, 916-24 (2008).
Wering et al., "c-Myc is Dispensable for Direct Reprogramming of Mouse Fibroblasts," Cell Stem Cell, 2008, 2, 10-12.
Wernig, et al., "In vitro reprogramming of fibroblasts into a pluripotent ES-cell-like state," Nature, Jul. 2007, vol. 448, No. 7151, pp. 318-324.
Wu et al., "Cellular senescence is an important mechanism of tumor regression upon c-Myc inactivation," PNAS, 2007, vol. 104(32), pp. 13028-13033.
Xiong et al., "Histone deacetylase inhibitors DNA methyltransferase-3B messenger RNA stability and down-regulate de novo DNA methyltransferase activity in human endometrial cells," Cancer Res., Apr. 2005, vol. 65(7), pp. 2684-2689.
Xu et al., Nat. Biotechnol, 2002, vol. 20, pp. 1261-1264.
Xu et al., Nature 453, 338-44 (2008).
Xu et al., "Revealing a core signaling regulatory mechanism for pluripotent stem cell survival and self-renewal by small molecules," PNAS, 2010, vol. 107(8), pp. 8129-8134.
Yamanaka, S. Cell 126, 663-676 (2006).
Yamanaka, "Strategies and New Developments in the Generation of Patient-Specific Pluripotent Stem Cells," Cell Stem Cell, Jul. 2007, vol. 1, pp. 39-49.
Ying et al, Nature, 2008, vol. 453, pp. 519-523.
Ying et al., Cell, 2003, vol. 115, pp. 281-292.
Yu et al., Science, 2007, vol. 318, pp. 1917-1920.
Zhao et al., Cell Death and Differentiation, 2007, vol. 14, pp. 489-499.
Zheng et al., Cancer Res., 2003, vol. 63, pp. 6909-6913.
Zhou et al., "Conversion of Mouse Epiblast Stem Cells to an Earlier Pluripotency State by Small Molecules," Journal of Biological Chemistry, Sep. 2010, vol. 285(39), pp. 29676-29680; DOI: 10.1074/jbc.C110.150599.
Zhou et al., Nature 455(7213):627-632 (2008).
Zhou, Hongyan et al.; Generation of Induced Pluripotent Stem Cells Using Recombinant Proteins; Cell Stem Cell, 4: 381-384 (2009).
Zhu et al, "Reprogramming of human primary somatic cells by OCT4 and chemical compounds," Cell Stem Cell, Dec. 2010, vol. 7, No. 6, pp. 651-655.
Egler et al., "Histone Deacetylase Inhibition and Blockade of the Glycolytic Pathway Synergistically Induce Glioblastoma Cell Death," Clin. Cancer Res., 2008, vol. 14(10), pp. 3132-3140.
Engel et al., "Allosteric activation of the protein kinase PDK1 with low molecular weight compounds," The EMBO Journal, 2006, vol. 25, pp. 5469-5480.
Gonzalez et al., "Generation of mouse-induced pluripotent stem cells by transient expression of a single nonviral polycistronic vector," PNAS, Jun. 2009, vol. 106(22), pp. 8918-8922.
Hakelien et al., "Transient alteration of cell fate using a nuclear and cytoplasmic extract of an insulinoma cell line," BBRC, vol. 316, pp. 834-841.
Pesce et al., "Differential expression of the Oct-4 transcription factor during mouse germ cell differentiation," Mechanisms of Development, 1998, vol. 71, pp. 89-98.
Wang et al., "The Immunophilin FKBP12 Functions as a Common Inhibitor of the TGFβ Family Type 1 Receptors," Cell, Aug. 1996, vol. 86, pp. 435-444.
Watanabe et al., "Activation of Akt signaling is sufficient to maintain pluripotency in mouse and primate embryonic stem cells," Oncogene, 2006, vol. 25, pp. 2697-2707.
Zhao et al., "Resorcylic Acid Lactones: Naturally Occurring Potent and Selective Inhibitors of MEK," The Journal of Antibiotics, Dec. 1999, vol. 52(12), pp. 1086-1094.
Condorelli, G. et al., "Cardiomyocytes induce endothelial cells to trans-differentiate into cardiac muscle: Implications for myocardium regeneration," PNAS, vol. 98, No. 19, Sep. 11, 2001, pp. 10733-10738.
Dravida, S. et al., "The transdifferentiation potential of limbal fibroblast-like cells," Developmental Brain Research, vol. 160, No. 2, Dec. 7, 2005, pp. 239-251.

(56) References Cited

OTHER PUBLICATIONS

Efe, Jem E. et al., "Conversion of mouse fibroblasts into cardiomyocytes using a direct reprogramming strategy," Nature Cell Biology, vol. 13, No. 3, Mar. 1, 2011, pp. 215-222.

Kaji et al., "Virus free induction of pluripotency and subsequent excision of reprogramming factors," Nature, Apr. 2009, vol. 458(7239), pp. 771-775.

Kim et al., "Pluripotent stem cells induced from adult neural stem cells by reprogramming with two factors," 2008, Nature 454:646-651.

Loh et al., "Generation of induced pluripotent stem cells from human blood," Blood, May 2009, vol. 113(22), pp. 5476-5479.

Takei, Shunsuke et al., "Bone morphogenetic protein-4 promotes induction of cardiomyocytes from human embryonic stem cells in serum-based embryoid body development," AJP Heart and Circulatory Physiology, vol. 296, No. 6, Jun. 2009, pp. H1793-H1803.

Takeuchi, Jun K. et al., "Directed transdifferentiation of mouse mesoderm to heart tissue by defined factors," Nature, vol. 459, No. 7247, Jun. 4, 2009, pp. 708-711.

EP10824189.4 , "Extended European Search Report", May 29, 2013, 8 Pages.

PCT/US2010/052896, "International Search Report and Written Opinion", Mar. 15, 2011, 14 pages.

Colman et al., Induced pluripotent stem cells and the stability of the differentiated state, EMBO Rep. vol. 10, No. 7. Jul. 2009, pp. 714-721.

Park et al., Reprogramming of human somatic cells to pluripotency with defined factors, Nature, vol. 451 No. 7175, Jan. 10, 2008, pp. 141-146.

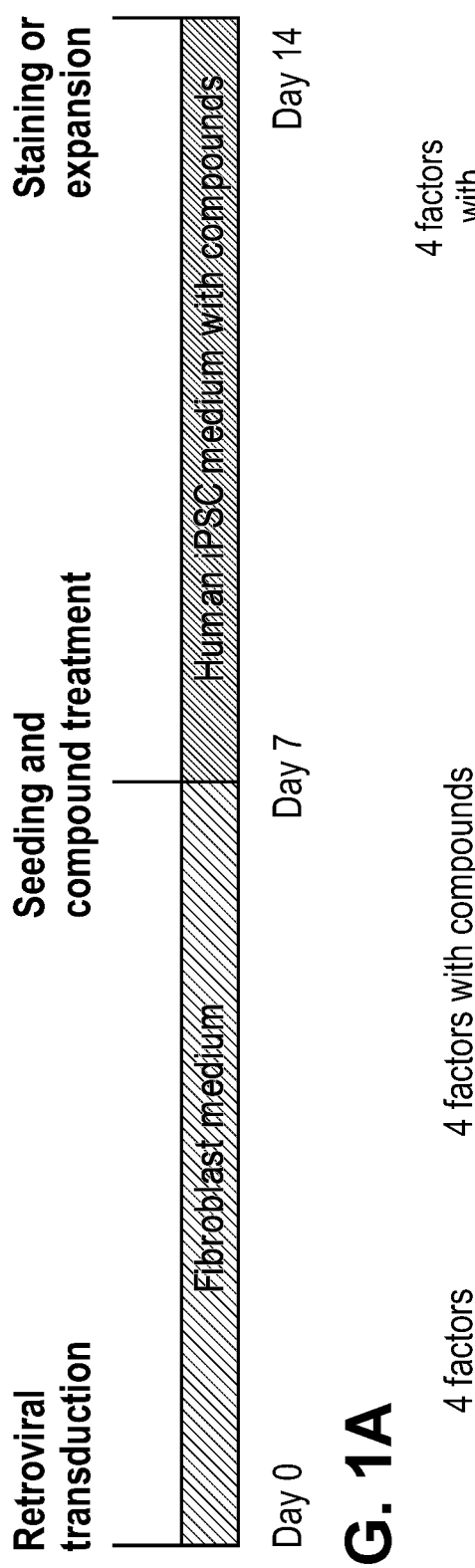
FIG. 1A
FIG. 1B
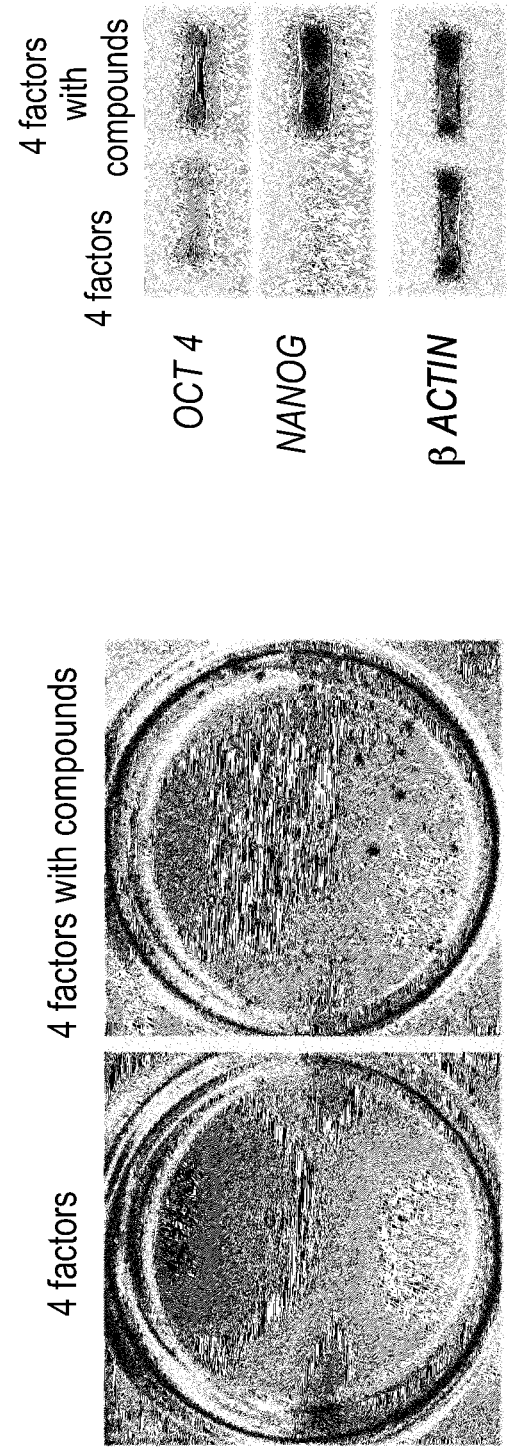
FIG. 1C

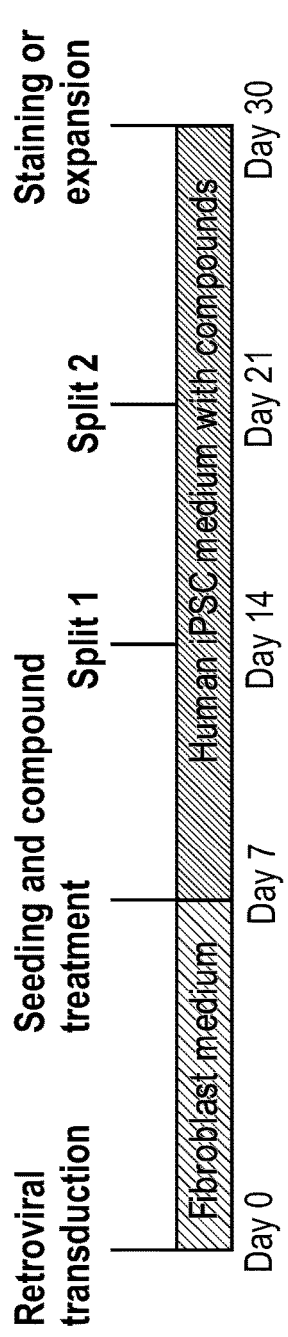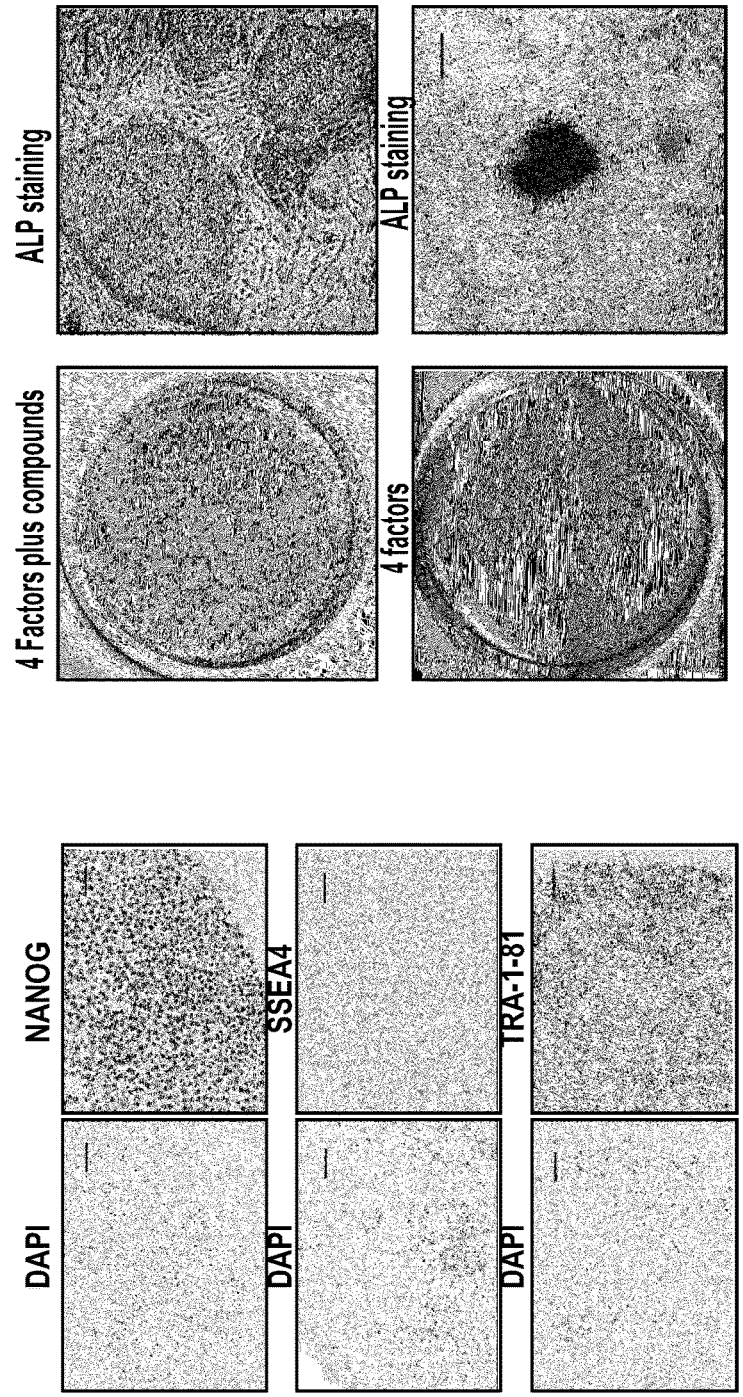
FIG. 2A
FIG. 2B
FIG. 2C

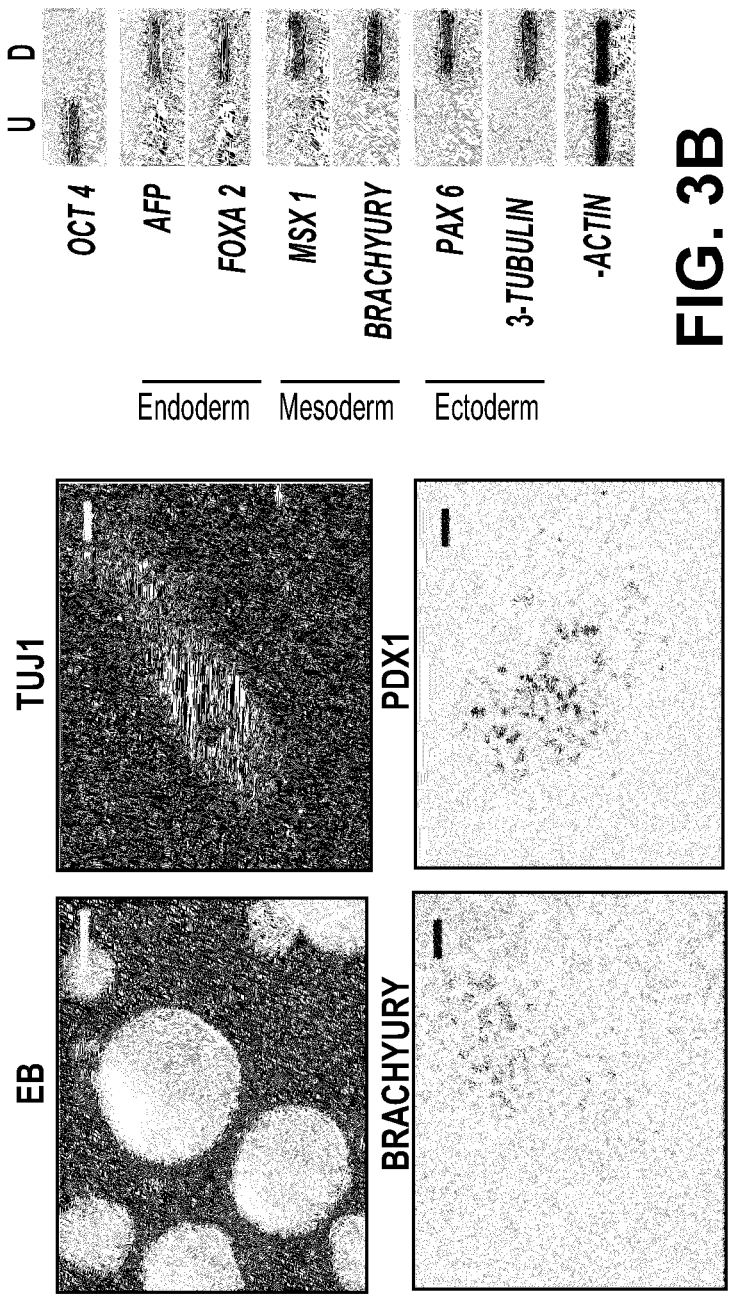
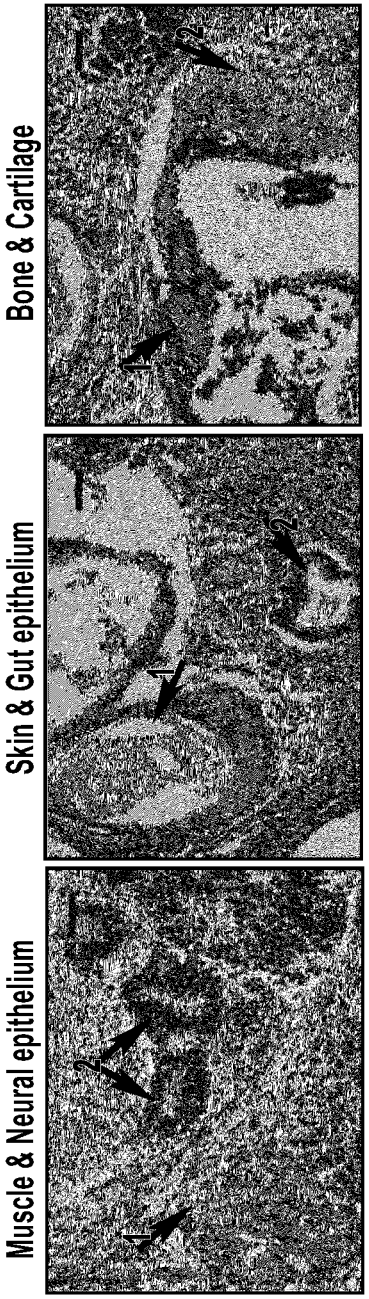
FIG. 3A
FIG. 3B
FIG. 3C

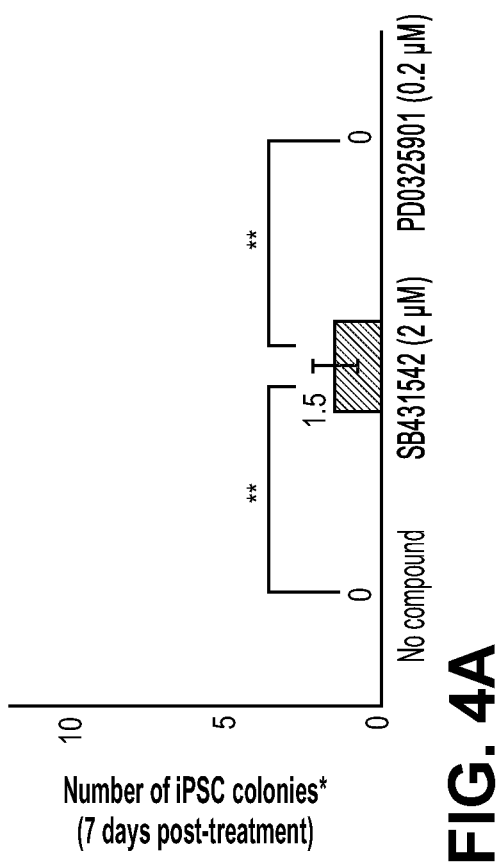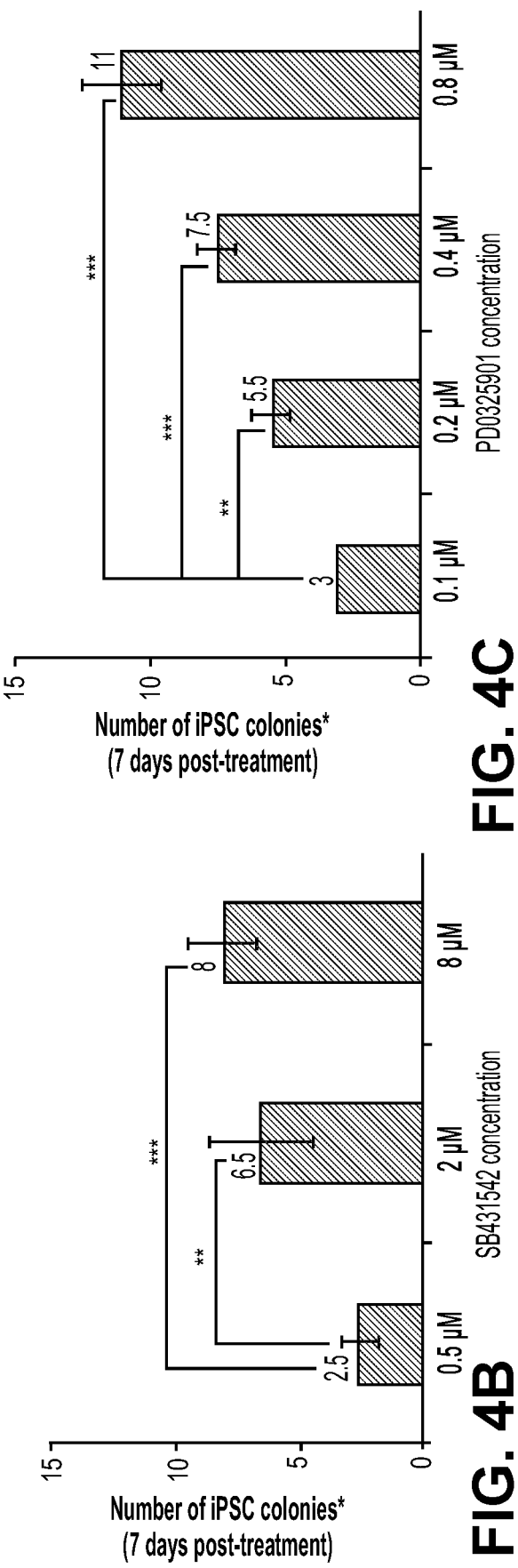
FIG. 4A
FIG. 4B
FIG. 4C

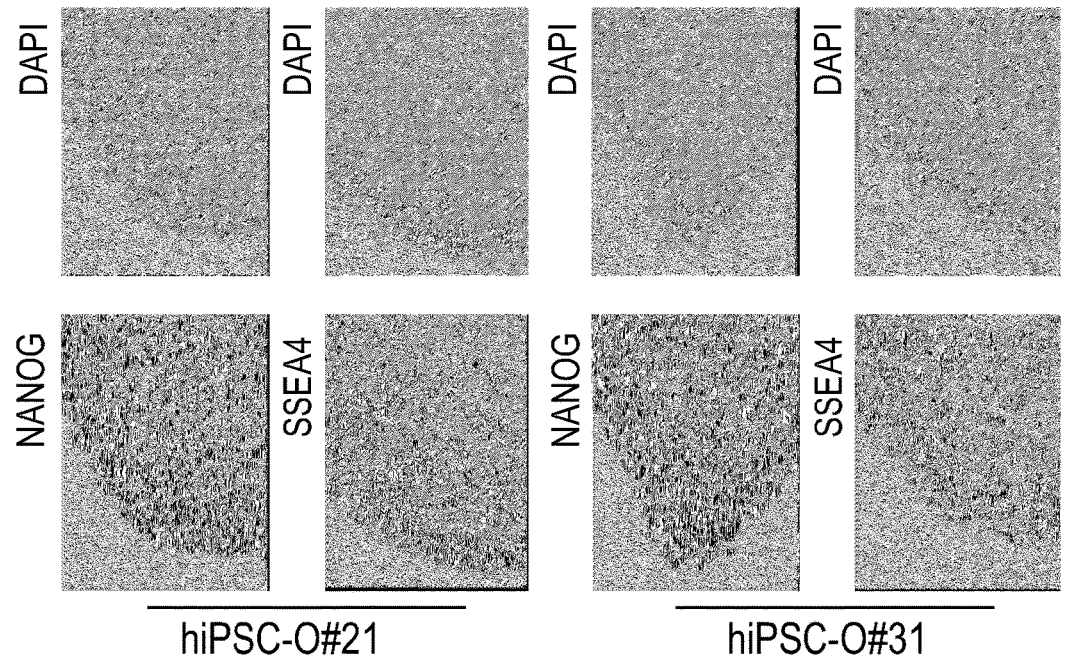
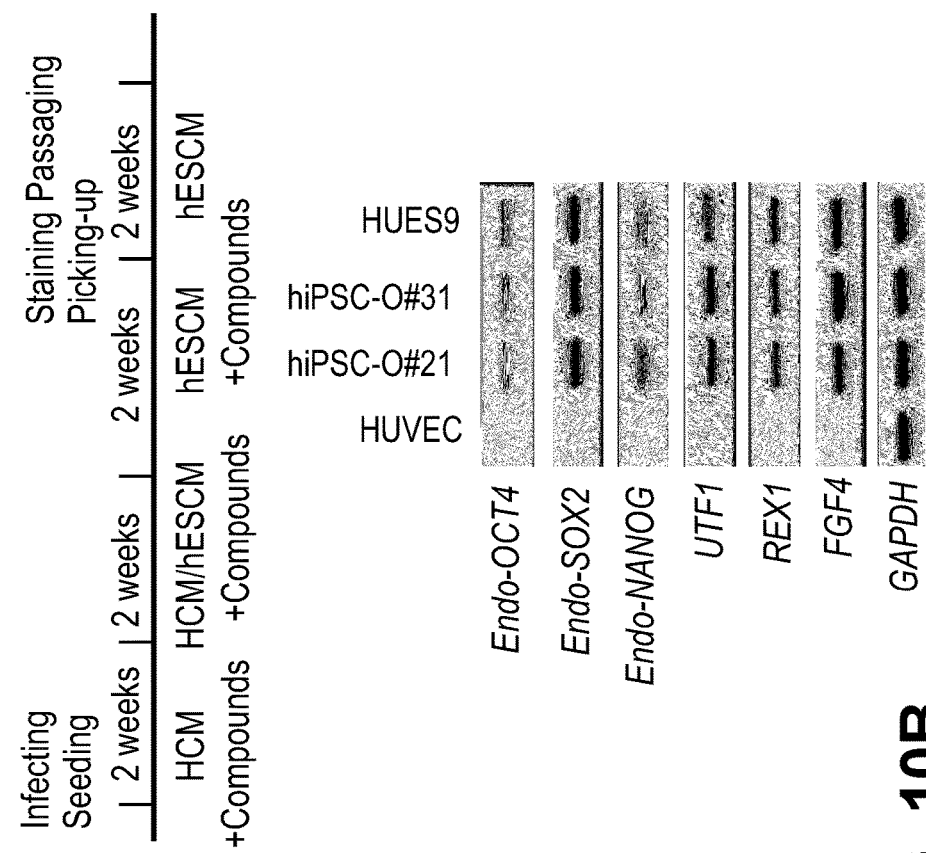
FIG. 10A FIG. 10B FIG. 10C

NANOG

DAPI

SOX2

DAPI

SSEA4

DAPI

TUJ1/DAPI

SMA/DAPI

AFP/DAPI

NANOG     DAPI

SOX2     DAPI

SSEA4     DAPI

TUJ1/DAPI

SMA/DAPI

AFP/DAPI

SEQUENCE LISTING

<160> NUMBER OF SEQ ID NOS: 47

<210> SEQ ID NO 1
<211> LENGTH: 20
<212> TYPE: DNA
<213> ORGANISM: Artificial Sequence
<220> FEATURE:
<223> OTHER INFORMATION: synthetic RT-PCR forward primer Endo-OCT4

<400> SEQUENCE: 1
agtttgtgcc agggttttg                                       20

<210> SEQ ID NO 2
<211> LENGTH: 20
<212> TYPE: DNA
<213> ORGANISM: Artificial Sequence
<220> FEATURE:
<223> OTHER INFORMATION: synthetic RT-PCR reverse primer Endo-OCT4

<400> SEQUENCE: 2
acttcacctt ccctccaacc                                      20

<210> SEQ ID NO 3
<211> LENGTH: 20
<212> TYPE: DNA
<213> ORGANISM: Artificial Sequence
<220> FEATURE:
<223> OTHER INFORMATION: synthetic RT-PCR forward primer Endo-SOX2

<400> SEQUENCE: 3
caaaaatggc catgcaggtt                                      20

<210> SEQ ID NO 4
<211> LENGTH: 24
<212> TYPE: DNA
<213> ORGANISM: Artificial Sequence
<220> FEATURE:
<223> OTHER INFORMATION: synthetic RT-PCR reverse primer Endo-SOX2

<400> SEQUENCE: 4
agttgggatc gaacaaaagc tatt                                 24

<210> SEQ ID NO 5
<211> LENGTH: 20

```
<212> TYPE: DNA
<213> ORGANISM: Artificial Sequence
<220> FEATURE:
<223> OTHER INFORMATION: synthetic RT-PCR forward primer Endo-NANOG

<400> SEQUENCE: 5
tttggaagct gctggggaag                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic RT-PCR reverse primer Endo-NANOG

<400> SEQUENCE: 6
gatgggagga ggggagagga                                              20

<210> SEQ ID NO 7
<211> LENGTH: 25
<212> TYPE: DNA
<213> ORGANISM: Artificial Sequence
<220> FEATURE:
<223> OTHER INFORMATION: synthetic RT-PCR forward primer Endo-KLF4

<400> SEQUENCE: 7
acgatcgtgg ccccggaaaa ggacc                                        25

<210> SEQ ID NO 8
<211> LENGTH: 27
<212> TYPE: DNA
<213> ORGANISM: Artificial Sequence
<220> FEATURE:
<223> OTHER INFORMATION: synthetic RT-PCR reverse primer Endo-KLF4

<400> SEQUENCE: 8
gattgtagtg ctttctggct gggctcc                                      27

<210> SEQ ID NO 9
<211> LENGTH: 26
<212> TYPE: DNA
<213> ORGANISM: Artificial Sequence
<220> FEATURE:
<223> OTHER INFORMATION: synthetic RT-PCR forward primer Endo-cMYC

<400> SEQUENCE: 9
gcgtcctggg aagggagatc cggagc                                       26

<210> SEQ ID NO 10
<211> LENGTH: 26
<212> TYPE: DNA
<213> ORGANISM: Artificial Sequence
<220> FEATURE:
<223> OTHER INFORMATION: synthetic RT-PCR reverse primer Endo-cMYC

<400> SEQUENCE: 10
ttgaggggca tcgtcgcggg aggctg                                       26

<210> SEQ ID NO 11
<211> LENGTH: 24
<212> TYPE: DNA
<213> ORGANISM: Artificial Sequence
<220> FEATURE:
<223> OTHER INFORMATION: synthetic RT-PCR forward primer REX1

<400> SEQUENCE: 11
```

```
cagatcctaa acagctcgca gaat                                          24
```

<210> SEQ ID NO 12
<211> LENGTH: 23
<212> TYPE: DNA
<213> ORGANISM: Artificial Sequence
<220> FEATURE:
<223> OTHER INFORMATION: synthetic RT-PCR reverse primer REX1

<400> SEQUENCE: 12

```
gcgtacgcaa attaaagtcc aga                                           23
```

<210> SEQ ID NO 13
<211> LENGTH: 24
<212> TYPE: DNA
<213> ORGANISM: Artificial Sequence
<220> FEATURE:
<223> OTHER INFORMATION: synthetic RT-PCR forward primer UTF1

<400> SEQUENCE: 13

```
ccgtcgctga acaccgccct gctg                                          24
```

<210> SEQ ID NO 14
<211> LENGTH: 24
<212> TYPE: DNA
<213> ORGANISM: Artificial Sequence
<220> FEATURE:
<223> OTHER INFORMATION: synthetic RT-PCR reverse primer UTF1

<400> SEQUENCE: 14

```
cgcgctgccc agaatgaagc ccac                                          24
```

<210> SEQ ID NO 15
<211> LENGTH: 25
<212> TYPE: DNA
<213> ORGANISM: Artificial Sequence
<220> FEATURE:
<223> OTHER INFORMATION: synthetic RT-PCR forward primer TDGF2

<400> SEQUENCE: 15

```
ctgctgcctg aatgggggaa cctgc                                         25
```

<210> SEQ ID NO 16
<211> LENGTH: 27
<212> TYPE: DNA
<213> ORGANISM: Artificial Sequence
<220> FEATURE:
<223> OTHER INFORMATION: synthetic RT-PCR reverse primer TDGF2

<400> SEQUENCE: 16

```
gccacgaggt gctcatccat cacaagg                                       27
```

<210> SEQ ID NO 17
<211> LENGTH: 23
<212> TYPE: DNA
<213> ORGANISM: Artificial Sequence
<220> FEATURE:
<223> OTHER INFORMATION: synthetic RT-PCR forward primer FGF4

<400> SEQUENCE: 17

```
ctacaacgcc tacgagtcct aca                                           23
```

<210> SEQ ID NO 18
<211> LENGTH: 24
<212> TYPE: DNA
<213> ORGANISM: Artificial Sequence

```
<220> FEATURE:
<223> OTHER INFORMATION: synthetic RT-PCR reverse primer FGF4

<400> SEQUENCE: 18
gttgcaccag aaaagtcaga gttg                                          24

<210> SEQ ID NO 19
<211> LENGTH: 20
<212> TYPE: DNA
<213> ORGANISM: Artificial Sequence
<220> FEATURE:
<223> OTHER INFORMATION: synthetic RT-PCR forward primer Exo-OCT4

<400> SEQUENCE: 19
tgtctccgtc accactctgg                                               20

<210> SEQ ID NO 20
<211> LENGTH: 18
<212> TYPE: DNA
<213> ORGANISM: Artificial Sequence
<220> FEATURE:
<223> OTHER INFORMATION: synthetic RT-PCR reverse primer Exo-OCT4

<400> SEQUENCE: 20
atgcatgcgg atccttcg                                                 18

<210> SEQ ID NO 21
<211> LENGTH: 18
<212> TYPE: DNA
<213> ORGANISM: Artificial Sequence
<220> FEATURE:
<223> OTHER INFORMATION: synthetic RT-PCR forward primer PAX6

<400> SEQUENCE: 21
tgtccaacgg atgtgagt                                                 18

<210> SEQ ID NO 22
<211> LENGTH: 20
<212> TYPE: DNA
<213> ORGANISM: Artificial Sequence
<220> FEATURE:
<223> OTHER INFORMATION: synthetic RT-PCR reverse primer PAX6

<400> SEQUENCE: 22
tttcccaagc aaagatggac                                               20

<210> SEQ ID NO 23
<211> LENGTH: 20
<212> TYPE: DNA
<213> ORGANISM: Artificial Sequence
<220> FEATURE:
<223> OTHER INFORMATION: synthetic RT-PCR forward primer betaIII TUBULIN

<400> SEQUENCE: 23
caacagcacg gccatccagg                                               20

<210> SEQ ID NO 24
<211> LENGTH: 21
<212> TYPE: DNA
<213> ORGANISM: Artificial Sequence
<220> FEATURE:
<223> OTHER INFORMATION: synthetic RT-PCR reverse primer betaIII TUBULIN

<400> SEQUENCE: 24
cttggggccc tgggcctccg a                                             21
```

```
<210> SEQ ID NO 25
<211> LENGTH: 20
<212> TYPE: DNA
<213> ORGANISM: Artificial Sequence
<220> FEATURE:
<223> OTHER INFORMATION: synthetic RT-PCR forward primer FOXF1

<400> SEQUENCE: 25
aaaggagcca cgaagcaagc                                                     20

<210> SEQ ID NO 26
<211> LENGTH: 21
<212> TYPE: DNA
<213> ORGANISM: Artificial Sequence
<220> FEATURE:
<223> OTHER INFORMATION: synthetic RT-PCR reverse primer FOXF1

<400> SEQUENCE: 26
aggctgaagc gaaggaagag g                                                   21

<210> SEQ ID NO 27
<211> LENGTH: 20
<212> TYPE: DNA
<213> ORGANISM: Artificial Sequence
<220> FEATURE:
<223> OTHER INFORMATION: synthetic RT-PCR forward primer HAND1

<400> SEQUENCE: 27 tccctttcc gcttgctctc                                                      20

<210> SEQ ID NO 28
<211> LENGTH: 20
<212> TYPE: DNA
<213> ORGANISM: Artificial Sequence
<220> FEATURE:
<223> OTHER INFORMATION: synthetic RT-PCR reverse primer HAND1

<400> SEQUENCE: 28
catcgcctac ctgatggacg                                                     20

<210> SEQ ID NO 29
<211> LENGTH: 20
<212> TYPE: DNA
<213> ORGANISM: Artificial Sequence
<220> FEATURE:
<223> OTHER INFORMATION: synthetic RT-PCR forward primer AFP

<400> SEQUENCE: 29
agcagcttgg tggtggatga                                                     20

<210> SEQ ID NO 30
<211> LENGTH: 21
<212> TYPE: DNA
<213> ORGANISM: Artificial Sequence
<220> FEATURE:
<223> OTHER INFORMATION: synthetic RT-PCR reverse primer AFP

<400> SEQUENCE: 30
cctgagcttg gcacagatcc t                                                   21

<210> SEQ ID NO 31
<211> LENGTH: 22
<212> TYPE: DNA
<213> ORGANISM: Artificial Sequence
<220> FEATURE:
<223> OTHER INFORMATION: synthetic RT-PCR forward primer GATA6
```

```
<400> SEQUENCE: 31
tgtgcgttca tggagaagat ca                                              22

<210> SEQ ID NO 32
<211> LENGTH: 27
<212> TYPE: DNA
<213> ORGANISM: Artificial Sequence
<220> FEATURE:
<223> OTHER INFORMATION: synthetic RT-PCR reverse primer GATA6

<400> SEQUENCE: 32
tttgataaga gacctcatga accgact                                         27

<210> SEQ ID NO 33
<211> LENGTH: 20
<212> TYPE: DNA
<213> ORGANISM: Artificial Sequence
<220> FEATURE:
<223> OTHER INFORMATION: synthetic RT-PCR forward primer GAPDH

<400> SEQUENCE: 33
gtggacctga cctgccgtct                                                 20

<210> SEQ ID NO 34
<211> LENGTH: 20
<212> TYPE: DNA
<213> ORGANISM: Artificial Sequence
<220> FEATURE:
<223> OTHER INFORMATION: synthetic RT-PCR reverse primer GAPDH

<400> SEQUENCE: 34
ggaggagtgg gtgtcgctgt                                                 20

<210> SEQ ID NO 35
<211> LENGTH: 25
<212> TYPE: DNA
<213> ORGANISM: Artificial Sequence
<220> FEATURE:
<223> OTHER INFORMATION: synthetic bisulfate-sequencing forward primer
      OCT4-1

<400> SEQUENCE: 35
ttaggaaaat gggtagtagg gattt                                           25

<210> SEQ ID NO 36
<211> LENGTH: 30
<212> TYPE: DNA
<213> ORGANISM: Artificial Sequence
<220> FEATURE:
<223> OTHER INFORMATION: synthetic bisulfate-sequencing reverse primer
      OCT4-1

<400> SEQUENCE: 36
tacccaaaaa acaaataaat tataaaacct                                      30

<210> SEQ ID NO 37
<211> LENGTH: 27
<212> TYPE: DNA
<213> ORGANISM: Artificial Sequence
<220> FEATURE:
<223> OTHER INFORMATION: synthetic bisulfate-sequencing forward primer
      OCT4-2

<400> SEQUENCE: 37
ggatgttatt aagatgaaga tagttgg                                         27
```

<210> SEQ ID NO 38
<211> LENGTH: 25
<212> TYPE: DNA
<213> ORGANISM: Artificial Sequence
<220> FEATURE:
<223> OTHER INFORMATION: synthetic bisulfate-sequencing reverse primer OCT4-2

<400> SEQUENCE: 38
cctaaactcc ccttcaaaat ctatt                                         25

<210> SEQ ID NO 39
<211> LENGTH: 30
<212> TYPE: DNA
<213> ORGANISM: Artificial Sequence
<220> FEATURE:
<223> OTHER INFORMATION: synthetic bisulfate-sequencing forward primer NANOG

<400> SEQUENCE: 39
gagttaaaga gttttgtttt taaaaattat                                    30

<210> SEQ ID NO 40
<211> LENGTH: 30
<212> TYPE: DNA
<213> ORGANISM: Artificial Sequence
<220> FEATURE:
<223> OTHER INFORMATION: synthetic bisulfate-sequencing reverse primer NANOG

<400> SEQUENCE: 40
tcccaaatct aataatttat catatctttc                                    30

<210> SEQ ID NO 41
<211> LENGTH: 19
<212> TYPE: DNA
<213> ORGANISM: Artificial Sequence
<220> FEATURE:
<223> OTHER INFORMATION: synthetic genotyping forward primer OCT4-Int

<400> SEQUENCE: 41
cagtgcccga aacccacac                                                19

<210> SEQ ID NO 42
<211> LENGTH: 24
<212> TYPE: DNA
<213> ORGANISM: Artificial Sequence
<220> FEATURE:
<223> OTHER INFORMATION: synthetic genotyping forward primer OCT4-Int

<400> SEQUENCE: 42
agaggaactg cttccttcac gaca                                          24

<210> SEQ ID NO 43
<211> LENGTH: 20
<212> TYPE: DNA
<213> ORGANISM: Artificial Sequence
<220> FEATURE:
<223> OTHER INFORMATION: synthetic genotyping forward primer SOX2-Int

<400> SEQUENCE: 43
tacctcttcc tcccactcca                                               20

<210> SEQ ID NO 44
<211> LENGTH: 24

```
<212> TYPE: DNA
<213> ORGANISM: Artificial Sequence
<220> FEATURE:
<223> OTHER INFORMATION: synthetic genotyping reverse primer SOX2-Int

<400> SEQUENCE: 44
agaggaactg cttccttcac gaca                                          24

<210> SEQ ID NO 45
<211> LENGTH: 24
<212> TYPE: DNA
<213> ORGANISM: Artificial Sequence
<220> FEATURE:
<223> OTHER INFORMATION: synthetic genotyping forward primer KLF4-Int

<400> SEQUENCE: 45
caccttgcct tacacatgaa gagg                                          24

<210> SEQ ID NO 46
<211> LENGTH: 22
<212> TYPE: DNA
<213> ORGANISM: Artificial Sequence
<220> FEATURE:
<223> OTHER INFORMATION: synthetic genotyping reverse primer KLF4-Int

<400> SEQUENCE: 46
cgtagaatcg agaccgagga ga                                            22

<210> SEQ ID NO 47
<211> LENGTH: 11
<212> TYPE: PRT
<213> ORGANISM: Artificial Sequence
<220> FEATURE:
<223> OTHER INFORMATION: synthetic L803 GSK3beta Inhibitor XIII
<221> NAME/KEY: PHOSPHORYLATION
<222> LOCATION: (10)...(10)
<223> OTHER INFORMATION: phosphoserine
<221> NAME/KEY: AMIDATION
<222> LOCATION: (11)...(11)
<223> OTHER INFORMATION: prolinamide

<400> SEQUENCE: 47

Lys Glu Ala Pro Pro Ala Pro Pro Gln Ser Pro
1               5                   10
```

INDUCTION OF PLURIPOTENT CELLS

CROSS-REFERENCE TO RELATED APPLICATIONS

This application is a continuation of U.S. application Ser. No. 14/637,089, filed Mar. 3, 2015, which is a continuation of U.S. application Ser. No. 13/500,373, filed Jun. 26, 2012, issued as U.S. Pat. No. 9,005,968, which is a U.S. National Stage application under 35 U.S.C. § 371 of International Application No. PCT/US2010/052896, filed Oct. 15, 2010, which claims priority to U.S. Provisional Application No. 61/252,548, filed Oct. 16, 2009, the contents of each of which are incorporated by reference in their entirety.

STATEMENT AS TO RIGHTS TO INVENTIONS MADE UNDER FEDERALLY SPONSORED RESEARCH AND DEVELOPMENT

This invention was made with government support under Contract No. HD-058110 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SEQTXT_77103-003820US-930402.txt, created on Mar. 2, 2015, 9,986 bytes, machine format IBM-PC, MS-Windows operating system, is hereby incorporated by reference in its entirety for all purposes.

BACKGROUND OF THE INVENTION

Recent advances in generating human induced pluripotent stem cells (iPSCs) (Takahashi, K. et al., *Cell* 131, 861-72 (2007); Yu, J. et al., *Science* 318, 1917-20 (2007); Muller, L. U. W., et al., *Mol. Ther.* 17, 947-53 (2009)) have raised hopes for their utility in biomedical research and clinical applications. However, iPSC generation is still a very slow (~4 weeks) and inefficient (<0.01% (Takahashi, K. et al., *Cell* 131, 861-72 (2007); Yu, J. et al., *Science* 318, 1917-20 (2007)) process that results in a heterogeneous population of cells. Identifying fully reprogrammed iPSCs from such a mixture is tedious, and requires specific expertise in human pluripotent cell culture.

Although the dangers of genomic insertion of exogenous reprogramming factors is being overcome, the low efficiency and slow kinetics of reprogramming continue to present a formidable problem for ultimate applications of human iPSC. For example, an increase in genetic or epigenetic abnormalities could occur during the reprogramming process, where tumor suppressors may be inhibited and oncogenic pathways may be activated. Though recent studies have reported an improved efficiency of reprogramming by genetic manipulations (Feng, B. et al., *Cell Stem Cell* 4, 301-12 (2009)) in addition to the original four factors, such manipulations typically make the process even more complex and increase the risk of genetic alterations and tumorigenicity. Thus, there is still a tremendous need for a safer, easier and more efficient procedure for human iPSC generation and facilitate identifying and characterizing fundamental mechanisms of reprogramming.

BRIEF SUMMARY OF THE INVENTION

The present invention provides for mixtures (e.g., useful for inducing iPSCs). In some embodiments, the mixture comprises:
mammalian cells;
a TGFβ receptor/ALK5 inhibitor;
a MEK inhibitor; and
a Rho GTPase/ROCK pathway inhibitor.

In some embodiments, at least 99% of the cells are non-pluripotent cells. In some embodiments, all or essentially all of the cells are non-pluripotent cells.

In some embodiments, the cells are human cells.

In some embodiments, the TGFβ receptor/ALK5 inhibitor is SB431542.

In some embodiments, the MEK inhibitor is PD0325901.

In some embodiments, the ROCK inhibitor is a compound having the formula:

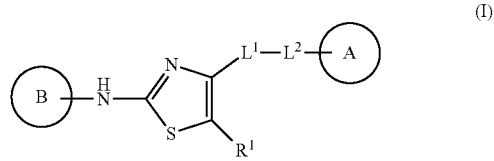

ring A is a substituted or unsubstituted cycloalkyl, substituted or unsubstituted heterocycloalkyl, substituted or unsubstituted aryl, or substituted or unsubstituted heteroaryl;
ring B is a substituted or unsubstituted heterocycloalkyl, or substituted or unsubstituted heteroaryl;
$L^1$ is —C(O)—NR$^2$— or —C(O)—NR$^2$—;
$L^2$ is a bond, substituted or unsubstituted alkylene or substituted or unsubstituted heteroalkylene; and
$R^1$ and $R^2$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl In some embodiments, the ROCK inhibitor has the formula:

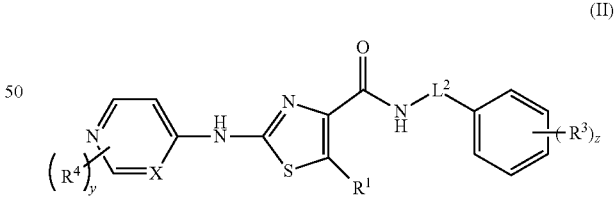

wherein, y is an integer from 0 to 3; z is an integer from 0 to 5; X is —N═, —CH═ or —CR$^5$═; R$^3$, R$^4$ and R$^5$ are independently CN, S(O)nR$^6$, NR$^7$R$^8$, C(O)R$^9$, NR$^{10}$—C(O)R$^{11}$, NR$^{12}$—C(O)—OR$^{13}$, —C(O)NR$^{14}$R$^{15}$, —NR$^{16}$S(O)2R$^{17}$, —OR$^{18}$, —S(O)2NR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two R$^3$ moieties are optionally joined together to form a substituted or unsubstituted cycloalkyl, substituted or unsubstituted heterocycloalkyl, substituted or unsubstituted aryl, or substituted or unsubstituted heteroaryl; and $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In some embodiments, the ROCK inhibitor has the formula:

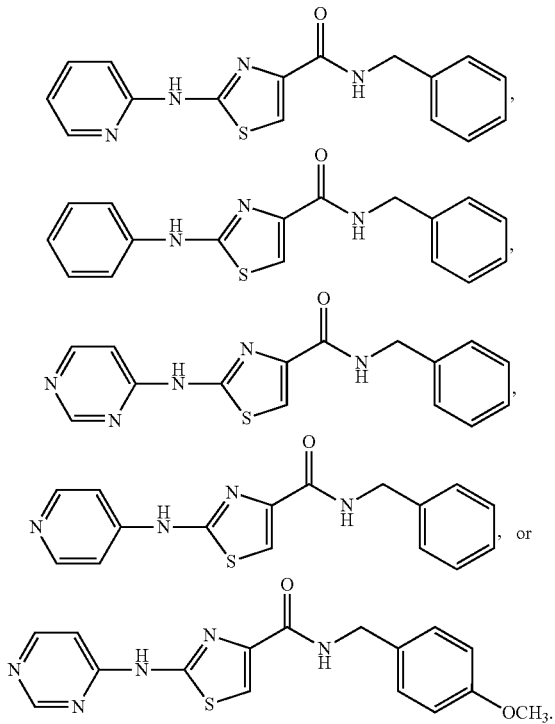

In some embodiments, the ROCK inhibitor is

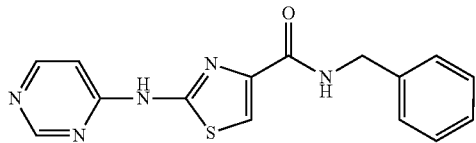 [SMILES: O=C(NCc1ccccc1)c1csc(Nc2ccncn2)n1]

In some embodiments, the concentration of the inhibitors is sufficient to improve by at least 10% the efficiency of induction of non-pluripotent cells in the mixture into induced pluripotent stem cells when the mixture is submitted to conditions sufficient to induce conversion of the cells into induced pluripotent stem cells.

In some embodiments, the mixture further comprises a GSK3 inhibitor and/or HDAC inhibitor.

In some embodiments, the polypeptides are selected from Oct-3/4, Sox2, KLF4 and c-Myc. In some embodiments, the cells are selected from human cell, non-human animal cells, mouse cells, non-human primates, or other animal cells.

The present invention also provides methods of inducing non-pluripotent mammalian cells into induced pluripotent stem cells. In some embodiments, the method comprises contacting non-pluripotent cells with:
a TGFβ receptor/ALK5 inhibitor;
a MEK inhibitor; and
a ROCK inhibitor,
under conditions sufficient to induce at least some cells to become pluripotent stem cells.

In some embodiments, the conditions comprise introducing at least one exogenous transcription factor into the non-pluripotent cells. In some embodiments, the at least one exogenous transcription factor is an Oct polypeptide and the cells are further contacted with a histone deacetylase (HDAC) inhibitor.

In some embodiments, the transcription factor is selected from the group consisting of an Oct polypeptide, a Klf polypeptide, a Myc polypeptide, and a Sox polypeptide.

In some embodiments, the method comprises introducing at least two, three or four exogenous transcription factor into the non-pluripotent cells, wherein the transcription factors are selected from the group consisting of an Oct polypeptide, a Klf polypeptide, a Myc polypeptide, and a Sox polypeptide. In some embodiments, the polypeptides are selected from Oct-3/4, Sox2, KLF4 and c-Myc. In some embodiments, the cells are selected from human cell, non-human animal cells, mouse cells, non-human primates, or other animal cells.

In some embodiments, the at least one transcription factor is introduced by introducing a polynucleotide into the non-pluripotent cells, wherein the polynucleotide encodes the at least one exogenous transcription factor, thereby expressing the transcription factor(s) in the cells.

In some embodiments, the at least one transcription factor is introduced by contacting an exogenous polypeptide to the non-pluripotent cells, wherein the polypeptide comprises the amino acid sequence of the transcription factor, wherein the introduction is performed under conditions to introduce the polypeptide into the cells. In some embodiments, the polypeptide comprises an amino acid sequence that enhances transport across cell membranes.

In some embodiments, the cells are human cells.
In some embodiments, the TGFβ receptor/ALK5 inhibitor is SB431542.

In some embodiments, the MEK inhibitor is PD0325901
In some embodiments, the ROCK inhibitor is a compound having the formula:

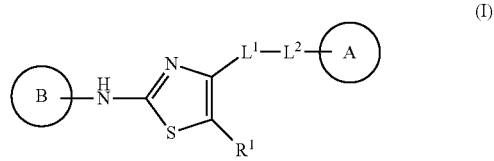

(I)

ring A is a substituted or unsubstituted cycloalkyl, substituted or unsubstituted heterocycloalkyl, substituted or unsubstituted aryl, or substituted or unsubstituted heteroaryl;
ring B is a substituted or unsubstituted heterocycloalkyl, or substituted or unsubstituted heteroaryl;
$L^1$ is —C(O)—$NR^2$— or —C(O)—$NR^2$—;
$L^2$ is a bond, substituted or unsubstituted alkylene or substituted or unsubstituted heteroalkylene; and
$R^1$ and $R^2$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, the ROCK inhibitor has the formula:

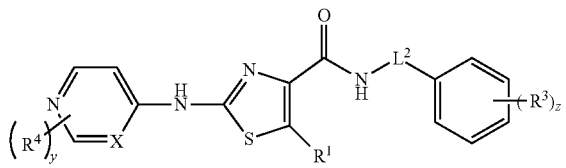

(II)

wherein, y is an integer from 0 to 3; z is an integer from 0 to 5; X is —N═, —CH═ or —CR⁵═; R³, R⁴ and R⁵ are independently CN, S(O)nR⁶, NR⁷R⁸, C(O)R⁹, NR¹⁰—C(O) R¹¹, NR¹²—C(O)—OR¹³, —C(O)NR¹⁴R¹⁵, —NR¹⁶S(O) 2R¹⁷, —OR¹⁸, —S(O)2NR¹⁹, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two R³ moieties are optionally joined together to form a substituted or unsubstituted cycloalkyl, substituted or unsubstituted heterocycloalkyl, substituted or unsubstituted aryl, or substituted or unsubstituted heteroaryl; and R⁶, R⁷, R⁸, R⁹, R¹⁰, R¹¹, R¹², R¹³, R¹⁴, R¹⁵, R¹⁶, R¹⁷, R¹⁸ and R¹⁹ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In some embodiments, the ROCK inhibitor has the formula:

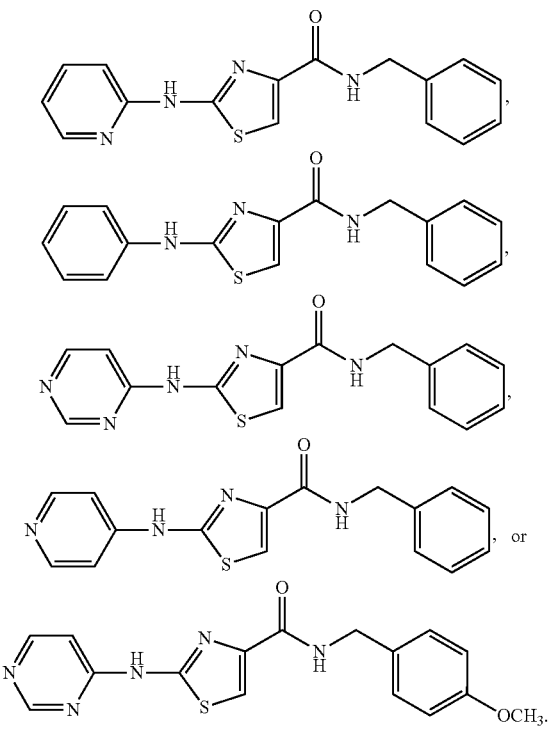

In some embodiments, the ROCK inhibitor is

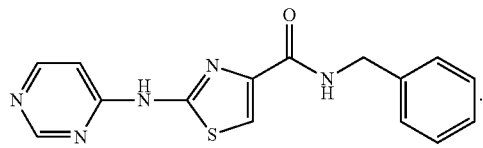 [SMILES: O=C(NCc1ccccc1)c1csc(Nc2ccncn2)n1]

In some embodiments, the concentration of the inhibitors is sufficient to improve by at least 10% the efficiency of induction of non-pluripotent cells in the mixture into induced pluripotent stem cells, when the mixture is subjected to conditions sufficient to induce conversion of the cells into induced pluripotent stem cells.

In some embodiments, the mixture further comprises a GSK3 inhibitor.

The present invention also provides for kits for inducing pluripotency in non-pluripotent mammalian cells. In some embodiments, the kit comprises, a TGFβ receptor/ALK5 inhibitor;
a MEK inhibitor; and
a ROCK inhibitor.

In some embodiments, the TGFβ receptor/ALK5 inhibitor is SB431542.

In some embodiments, the MEK inhibitor is PD0325901.

In some embodiments, the ROCK inhibitor is a compound having the formula:

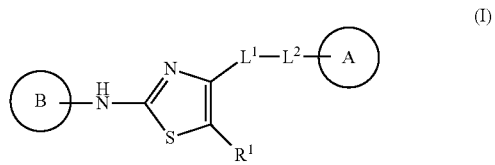

(I)

ring A is a substituted or unsubstituted cycloalkyl, substituted or unsubstituted heterocycloalkyl, substituted or unsubstituted aryl, or substituted or unsubstituted heteroaryl;

ring B is a substituted or unsubstituted heterocycloalkyl, or substituted or unsubstituted heteroaryl;

L¹ is —C(O)—NR²— or —C(O)—NR²—;

L² is a bond, substituted or unsubstituted alkylene or substituted or unsubstituted heteroalkylene; and R¹ and R² are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl In some embodiments, the ROCK inhibitor has the formula:

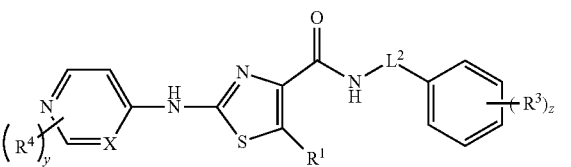

(II)

wherein, y is an integer from 0 to 3; z is an integer from 0 to 5; X is —N=, —CH= or —CR$^5$=; R$^3$, R$^4$ and R$^5$ are independently CN, S(O)nR$^6$, NR$^7$R$^8$, C(O)R$^9$, NR$^{10}$—C(O)R$^{11}$, NR$^{12}$—C(O)—OR$^{13}$, —C(O)NR$^{14}$R$^{15}$, —NR$^{16}$S(O)2R$^{17}$, —OR$^{18}$, —S(O)2NR$^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two R$^3$ moieties are optionally joined together to form a substituted or unsubstituted cycloalkyl, substituted or unsubstituted heterocycloalkyl, substituted or unsubstituted aryl, or substituted or unsubstituted heteroaryl; and R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$ and R$^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In some embodiments, the ROCK inhibitor has the formula:

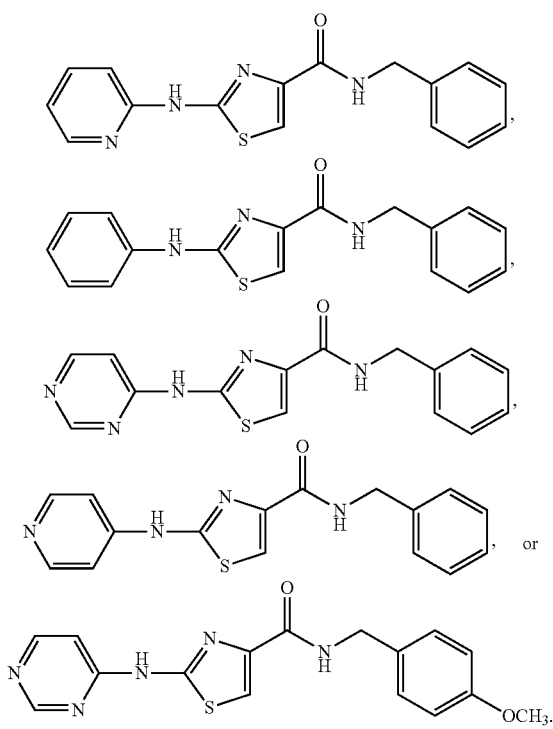

In some embodiments, the ROCK inhibitor is

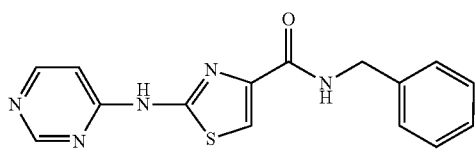 [SMILES: O=C(NCc1ccccc1)c1csc(Nc2ccncn2)n1]

In some embodiments, the kit further comprises a GSK3 inhibitor and/or a histone deacetylase (HDAC) inhibitor.

Other embodiments will be clear from the remainder of this disclosure.

Definitions

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Oct polypeptides include, Oct-1, Oct-2, Oct-3/4, Oct-6, Oct-7, Oct-8, Oct-9, and Oct-11. e.g. Oct3/4 (referred to herein as "Oct4") contains the POU domain, a 150 amino acid sequence conserved among Pit-1, Oct-1, Oct-2, and uric-86. See, Ryan, A. K. & Rosenfeld, M. G. Genes Dev. 11, 1207-1225 (1997). In some embodiments, variants have at least 85%, 90%, or 95% amino acid sequence identity across their whole sequence compared to a naturally occurring Oct polypeptide family member such as to those listed above or such as listed in Genbank accession number NP 002692.2 (human Oct4) or NP_038661.1 (mouse Oct4). Oct polypeptides (e.g., Oct3/4) can be from human, mouse, rat, bovine, porcine, or other animals. Generally, the same species of protein will be used with the species of cells being manipulated.

A "Klf polypeptide" refers to any of the naturally-occurring members of the family of Krüppel-like factors (Klfs), zinc-finger proteins that contain amino acid sequences similar to those of the *Drosophila* embryonic pattern regulator Krüppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, Dang, D. T., Pevsner, J. & Yang, V. W. Cell Biol. 32, 1103-1121 (2000). Exemplary Klf family members include, Klf1, Klf2, Klf3, Klf-4, Klf5, Klf6, Klf7, Klf8, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. See, Nakagawa, et al., Nature Biotechnology 26:101-106 (2007). In some embodiments, variants have at least 85%, 90%, or 95% amino acid sequence identity across their whole sequence compared to a naturally occurring Klf polypeptide family member such as to those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. To the extent a Klf polypeptide is described herein, it can be replaced with an estrogen-related receptor beta (Essrb) polypeptide. Thus, it is intended that for each Klf polypeptide embodiment described herein, a corresponding embodiment using Essrb in the place of a Klf4 polypeptide is equally described.

A "Myc polypeptide" refers any of the naturally-occurring members of the Myc family (see, e.g., Adhikary, S. & Eilers, M. *Nat. Rev. Mol. Cell Biol.* 6:635-645 (2005)), or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as to those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated.

A "Sox polypeptide" refers to any of the naturally-occurring members of the SRY-related HMG-box (Sox) transcription factors, characterized by the presence of the high-mobility group (HMG) domain, or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, e.g., Dang, D. T., et al., *Int. J. Biochem. Cell Biol.* 32:1103-1121 (2000). Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. See, Nakagawa, et al., *Nature Biotechnology* 26:101-106 (2007). In some embodiments, variants have at least 85%, 90%, or 95% amino acid sequence identity across their whole sequence compared to a naturally occurring Sox polypeptide family member such as to those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated.

"H3K9" refers to histone H3 lysine 9. H3K9 modifications associated with gene activity include H3K9 acetylation and H3K9 modifications associated with heterochromatin, include H3K9 di-methylation or tri-methylation. See, e.g., Kubicek, et al., *Mol. Cell* 473-481 (2007).

The term "pluripotent" or "pluripotency" refers to cells with the ability to give rise to progeny cells that can undergo differentiation, under the appropriate conditions, into cell types that collectively demonstrate characteristics associated with cell lineages from all of the three germinal layers (endoderm, mesoderm, and ectoderm). Pluripotent stem cells can contribute to all embryonic derived tissues of a prenatal, postnatal or adult animal. A standard art-accepted test, such as the ability to form a teratoma in 8-12 week old SCID mice, can be used to establish the pluripotency of a cell population, however identification of various pluripotent stem cell characteristics can also be used to detect pluripotent cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least some, and in some embodiments, all of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics.

As used herein, "non-pluripotent cells" refer to mammalian cells that are not pluripotent cells. Examples of such cells include differentiated cells as well as progenitor cells. Examples of differentiated cells include, but are not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and T-cells.

In some embodiments where an individual is to be treated with the resulting pluripotent cells, the individual's own non-pluripotent cells are used to generate pluripotent cells according to the methods of the invention.

Cells can be from, e.g., humans or non-human mammals. Exemplary non-human mammals include, but are not limited to, mice, rats, cats, dogs, rabbits, guinea pigs, hamsters, sheep, pigs, horses, bovines, and non-human primates (e.g., chimpanzees, macaques, and apes).

A "recombinant" polynucleotide is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

"Expression cassette" refers to a polynucleotide comprising a promoter or other regulatory sequence operably linked to a sequence encoding a protein.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "heterologous sequence" or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA, being linked to a heterologous promoter, being linked to a reporter gene, etc.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Inhibitors," "activators," and "modulators" of expression or of activity are used to refer to inhibitory, activating, or modulating molecules, respectively, identified using in vitro and in vivo assays for expression or activity of a described target protein (or encoding polynucleotide), e.g., ligands, agonists, antagonists, and their homologs and mimetics. The term "modulator" includes inhibitors and activators. Inhibitors are agents that, e.g., inhibit expression or bind to, partially or totally block stimulation or protease inhibitor activity, reduce, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100%. Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more higher.

Where chemical substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being exemplified in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from a aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S(O2)—R', where R' is an alkyl group as defined above. R' may have a specified number of carbons (e.g. "C1-C4 alkylsulfonyl").

Each of the above terms (e.g., "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', —halogen, —SiR'R"R'", —OC(O)R, —C(O)W, —CO₂R, —CONR'R", —OC(O)NR'R", —NR"C(O)R, —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —CN and —NO₂ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: halogen, —OR', —NR'R", —SR', —halogen, —SiR'R"R'", —OC(O)R, —C(O)R', —CO₂R, —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —CN and —NO₂, —R', —N₃, —CH(Ph)₂, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula —T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH₂)$_r$—B—, wherein A and B are independently —CRR'—, —O—, —NR—, —S—, —S(O)—, —S(O)₂—, —S(O)₂NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X$^1$—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:
(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds;

the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

BRIEF DESCRIPTION OF THE DRAWINGS

FIG. 1A-1F. Compound treatment for seven days is sufficient to induce pluripotent stem cells from human fibroblasts transduced with the four reprogramming factors. (FIG. 1A) Timeline for human iPSC induction using combined SB431542 and PD0325901 treatment along with 4TFs. Treatment began with cell re-seeding at day 7 after 4TF transduction and was maintained for 7 days. (FIG. 1B) Staining for ALP$^+$ colonies that emerged in the untreated (left) or 2 compound-treated (right) cultures within seven days. (FIG. 1C) RT-PCR showing elevated endogenous mRNA expression of pluripotency markers OCT4 and NANOG in 2 compound-treated cultures. (FIG. 1D) TRA-1-81 staining at day 14 without (left) or with (right) 2 compound treatment. (FIG. 1E) The numbers of NANOG$^+$ colonies at day 14 under different treatment conditions are plotted. (FIG. 1F) Typical staining for hESC-specific markers (NANOG and SSEA4) exhibited by D14 iPSCs. Scale bars, 50 μm in (d & f).

FIG. 2A-2F. Prolonged compound treatment and cell passaging dramatically increased the number of reprogrammed colonies. (FIG. 2A) Timeline of human iPSC induction using SB431542, PD0325901 and thiazovivin. (FIG. 2B) Day 30 iPSCs expressed pluripotency markers NANOG, SSEA4 and TRA-1-81. Scale bars, 50 μm (FIG. 2C) ALP staining of day 30 cultures with (upper panels) or without (lower panels) 3 compound treatment. Boxed areas in the left panels are enlarged in the right panels. Scale bars, 200 μm (FIG. 2D) Number of NANOG$^+$ colonies on day 30 under different treatment conditions, without splitting. (FIG. 2E) Number of NANOG$^+$ colonies on day 30 from 3 compound-treated cultures trypsinized as indicated. (FIG. 2F) RT-PCR on iPSC colonies obtained with 3 compound treatment shows reactivated expression of endogenous pluripotency markers. HDF: Human Dermal Fibroblast.

FIG. 3A-3C. In vitro and in vivo differentiation of iPSCs generated with 3 compound treatment. (FIG. 3A) Micrographs show embryoid bodies (EB) generated from iPSCs and in vitro differentiation into ectodermal TUBULIN), mesodermal (BRACHYURY) and endodermal (PDX1) cell types. Scale bars, EB: 100 μm; others 10 μm (FIG. 3B) RT-PCR showing expression of representative lineage markers and the absence of OCT4 mRNA expression in differentiating cells. U—undifferentiated, D—differentiated. (FIG. 3C) Teratomas generated in nude mice from iPSCs (3 independent colonies tested) consist of tissues from all three germ layers. Left panel: 1-muscle, 2-neural epithelium; middle panel: 1-skin, 2-gut epithelium; right panel: 1-bone, 2-cartilage. Scale bars, 20 μm.

FIG. 4A-4C. Compound treatment enhanced iPS cell generation in a dose dependent manner.

(FIG. 6A) The reprogramming effect of the SB431542 and PD0325901 combination was tested on BJ cells transduced with lentiviral vectors (pSin) carrying the four factors (OCT4, NANOG, SOX2, and LIN28). On day 30 the compound-treated cultures showed a substantially increased number of ALP+ hESC-like colonies when compared to 4TFs control. (FIG. 6B) BJ cells were transduced with retrovirus carrying a YFP expression vector and were cultured either in the presence or absence of SB431542, PD0325901, and Thiazovivin. (FIG. 6C-6F) Cells were subjected to (FIG. 6C) FACS analysis on day 10 and day 38 or (FIG. 6D-6F) fluorescence microscopy on day 3 (FIG. 6D), day 10 (FIG. 6E), and day 28 (FIG. 6F).

(FIG. 8A) Treatment with 0.5 μM PD0325901 (PD) and 0.5 μM A-83-01 (A83) significantly improved generation of iPSCs from primary human keratinocytes transduced with either 4TFs (4F, OKSM) or 3TFs (3F, OKS). NHEKs were seeded at a density of 100,000 transduced cells per 10 cm dish. (FIG. 8B) Further chemical screens identified PS48, NaB, and their combination that can substantially enhance reprogramming of primary human keratinocytes transduced with 2TFs (OK). NHEKs were seeded at a density of 100,000 transduced cells per 10 cm dish. (FIG. 8C) Experimental scheme for generation of human iPSCs from primary human keratinocytes transduced by a single reprogramming gene, OCT4. KCM, keratinocyte culture medium; hESCM, human ESC culture media. (FIG. 8D) Live immunostaining with TRA-1-81 of iPSC colonies that were generated from primary human keratinocytes transduced with 2TFs/OK or 1TF/OCT4 before picking-up of colonies. (FIG. 8E) The established human iPSC-OK and iPSC-O cells express typical pluripotency markers, including ALP (alkaline phosphatase), OCT4, SOX2, NANOG, SSEA-4 and TRA-1-81. Nuclei were stained with DAPI.

(FIG. 9A) Expression analysis by RT-PCR of the endogenous pluripotency genes and exogenous OCT4 and KLF4. GAPDH was used as an input control. (FIG. 9B) Methylation analysis of the OCT4 and NANOG promoters by bisulfate genomic sequencing. Open circles and closed circles indicate unmethylated and methylated CpGs in the promoter regions, respectively. (FIG. 9C) Scatter plots comparing global gene expression patterns between iPSC-O cells and NHEKs, and hESCs. The positions of the pluripotency genes OCT4, NANOG, and SOX2 are shown by arrows. Black lines indicate the linear equivalent and twofold changes in gene expression levels between the samples. (FIG. 9D) Human iPSC-OK and iPSC-O could effectively differentiate in vitro into cells in the three germ layers, including neural ectodermal cells tubulin), mesodermal cells (SMA), and endodermal cells (AFP) using EB method. (FIG. 9E) Quantitative PCR test of three germ layer markers from differentiated human iPSCs using EB method: ectoderm (PAX6, βIII TUBULIN), mesoderm (FOXF1, HAND1) and endoderm (AFP, GATA6). Data denotes GAPDH-normalized fold changes relative to undifferentiated parental human iPSCs. (FIG. 9F) Human iPSC-OK and iPSC-O could effectively produce full teratoma, which contains differentiated cells in the three germ layers, in SCID mice.

FIG. 10A-10F. Generation and characterizations of human induced pluripotent stem cells from human umbilical vein endothelial cells by single gene, OCT4, and small molecules. (FIG. 10A) Experimental scheme for generation of human iPSCs from HUVECs transduced by OCT4. HCM, HUVEC culture medium; hESCM, human ESC culture media. (FIG. 10B) The established hiPSC-O cells from HUVECs express typical pluripotency markers, including NANOG and SSEA-4. Nuclei were stained with DAPI. (FIG. 10C) Expression analysis by RT-PCR of the endogenous pluripotency genes. GAPDH was used as an input control. (FIG. 10D) Methylation analysis of the OCT4 and NANOG promoters by bisulfate genomic sequencing. Open circles and closed circles indicate unmethylated and methylated CpGs in the promoter regions, respectively. (FIG. 10E) hiPSC-O cells from HUVECs could effectively differentiate in vitro into cells in the three germ layers, including neural ectodermal cells tubulin), mesodermal cells (SMA), and endodermal cells (AFP) using EB method. (FIG. 10F) hiPSC-O cells could effectively produce full teratoma, which contains differentiated cells in the three germ layers in SCID mice.

(FIG. 11A) The established hiPSC-O cells from adult keratinocytes express typical pluripotency markers, including NANOG, SOX2 and SSEA-4. Nuclei were stained with DAPI. (FIG. 11B) These hiPSC-O cells could effectively differentiate in vitro into cells in the three germ layers, including neural ectodermal cells tubulin), mesodermal cells (SMA), and endodermal cells (AFP) using EB method.

(FIG. 12A) The established hiPSC-O cells from amniotic fluid derived cells express typical pluripotency markers, including NANOG, SOX2 and SSEA-4. Nuclei were stained with DAPI. (FIG. 12B) These hiPSC-O cells could effectively differentiate in vitro into cells in the three germ layers, including neural ectodermal cells tubulin), mesodermal cells (SMA), and endodermal cells (AFP) using EB method.

DETAILED DESCRIPTION

I. Introduction

Figure 1D:
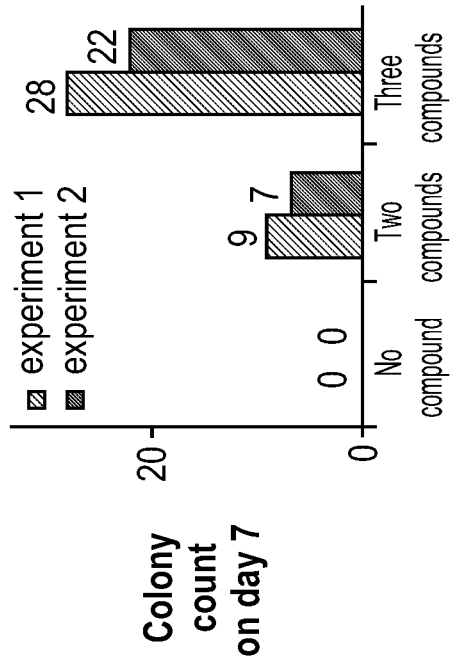

The present invention is based on the surprising discovery that a combination of an ALK5 inhibitor, a MEK inhibitor, and a ROCK inhibitor greatly improves efficiency of induction of pluripotency in non-pluripotent mammalian cells transformed with four transcription factors. Accordingly, the present invention provides for methods of inducing pluripotency in non-pluripotent mammalian cells wherein the method comprises contacting the non-pluripotent cells with at least a TGFβ receptor/ALK5 inhibitor, preferably in combination with a MEK/ERK pathway inhibitor, and in particular embodiments, a Rho GTPase/ROCK inhibitor.

II. TGFβ Receptor/ALK5 Inhibitors

Activin receptor-like kinase 5 (ALK-5) is the principal TGFβ receptor that mediates cellular responses to TGF-βs (Massague J. *Annu Rev Biochem* 67:753-791 (1998); Massague J, Chen YG. *Genes Dev* 14:627-644 (2000); Franzen P, et al. Cell 75:681-692 (1993)). Upon ligand binding, constitutively active TORII kinase phosphorylates ALK-5 which, in turn, activates the downstream signal transduction cascades. ALK-5-activated Smad2 and Smad3 phosphorylation is the most prominent pathway (Massague J, Chen YG. *Genes Dev* 14:627-644 (2000)). Once activated, Smad2/3 associates with Smad4 and translocates to the nucleus, where the complex transcriptionally regulates target gene expression.

TGFβ receptor (i.e. ALK5) inhibitors can include antibodies to, dominant negative variants of, and siRNA, microRNA, antisense nucleic acids, and other polynucleotides that suppress expression of, TGFβ receptors (e.g., ALK5). Exemplary TGFβ receptor/ALK5 inhibitors include, but are not limited to, SB431542 (see, e.g., Inman, et al., *Molecular Pharmacology* 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo, et al., *Cancer Science* 96(11):791-800 (2005), and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton, et al., WO2008/094597, herein incorporated by reference), BMP4 (see, Dalton, supra), GW788388 (-{4-[3-(pyridin-2-yl)-1H-pyrazol-4-yl]pyridin-2-yl}-N—(tetrahydro-2H-pyran-4-yl)benzamide) (see, e.g., Gellibert, et al., *Journal of Medicinal Chemistry* 49(7):2210-2221 (2006)), SM16 (see, e.g., Suzuki, et al., *Cancer Research* 67(5):2351-2359 (2007)), IN-1130 (3-((5-(6-methylpyridin-2-yl)-4-(quinoxalin-6-yl)-1H-imidazol-2-yl)methyl)benzamide) (see, e.g., Kim, et al., *Xenobiotica* 38(3):325-339 (2008)), GW6604 (2-phenyl-4-(3-pyridin-2-yl-1H-pyrazol-4-yl)pyridine) (see, e.g., de Gouville, et al., *Drug News Perspective* 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta, et al., *Molecular Pharmacology* 65(3):744-752 (2004)) and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., *J, Mol. Phamacol.* 62(1): 65-74 (2002).

In view of the data herein showing the effect of inhibiting ALK5, it is believed that inhibition of the TGFβ/activin pathway will have similar effects. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

TGFβ receptor inhibitors can include antibodies to, dominant negative variants of and siRNA or antisense nucleic acids that target TGFβ receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY209761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGFβ receptors. (See, e.g., Wrzesinski, et al., *Clinical Cancer Research* 13(18):5262-5270 (2007); Kaminska, et al., *Acta Biochimica Polonica* 52(2):329-337 (2005); and Chang, et al., *Frontiers in Bioscience* 12:4393-4401 (2007). In addition, the inventors have found that the TGFβ inhibitors BMP-4 and BMP-7 have similar cellular reprogramming effects as the ALK5 inhibitor described in the examples, thereby providing further evidence that TGFβ inhibitors can be used for reprogramming (e.g., in combination with a MEK/ERK pathway inhibitor and a Rho GTPase/ROCK inhibitor). Exemplary human BMP-4 and BMP-7 protein sequences are set forth in, for example, U.S. Pat. No. 7,405,192.

Inhibitors of SMAD 2/3 phosphorylation can include antibodies to, dominant negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., *Oncogene* 26:3311-3320 (2007); and Kataoka, et al., EP1992360, incorporated herein by reference.)

Inhibitors of the interaction of SMAD 2/3 and smad4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., *Oncogene* 24:3864-3874 (2005) and Zhao, et al., *Molecular Biology of the Cell*, 17:3819-3831 (2006).)

Activators/agonists of SMAD 6 and SMAD 7 include but are not limited to antibodies to, dominant negative variants of and antisense nucleic acids that target SMAD 6 or SMAD 7. Specific examples of inhibitors include but are not limited to smad7-as PTO-oligonucleotides. See, e.g., Miyazono, et al., U.S. Pat. No. 6,534,476, and Steinbrecher, et al., US2005119203, both incorporated herein by reference.

Those of skill will appreciate that the concentration of the TGFβ receptor/ALK5 inhibitor will depend on which specific inhibitor is used. Generally, the concentration of a TGFβ receptor/ALK5 inhibitor in a cell culture will be in the range of IC20-IC100 (i.e., concentrations in which 20% inhibition to 100% inhibition in cells is achieved. For example, SB432542 would be used at 0.5-10 μM, optimally around 1-5 μM. In certain embodiments, a combination of two or more different TGFβ receptor/ALK5 inhibitors can be used.

III. MEK/ERK Pathway Inhibitors

The MEK/ERK pathway refers to the MEK and ERK serine/threonine kinases that make up part of a signal transduction pathway. Generally, activated Ras activates the protein kinase activity of RAF kinase. RAF kinase phosphorylates and activates MEK, which in turn phosphorylates and activates a mitogen-activated protein kinase (MAPK). MAPK was originally called "extracellular signal-regulated kinases" (ERKs) and microtubule-associated protein kinase (MAPK). Thus, "ERK" and "MAPK" are used synonymously.

MEK/ERK pathway inhibitors refer to inhibitors of either MEK or ERK that are part of the Raf/MEK/ERK pathway. Because the inventors have found that MEK inhibitors are effective in improving induction of iPSCs, and because MEK directly controls ERK activity, it is believed that MEK inhibitors as described for the present invention, can be replaced with an ERK inhibitor as desired.

Inhibitors of MEK (i.e., MEK1 (also known as mitogen-activated protein kinase kinase 1) and/or MEK2 (also known as mitogen-activated protein kinase kinase 2)) can include antibodies to, dominant negative variants of, and siRNA and siRNA, microRNA, antisense nucleic acids, and other polynucleotides that suppress expression of, MEK. Specific examples of MEK inhibitors include, but are not limited to, PD0325901, (see, e.g., Rinehart, et al., *Journal of Clinical Oncology* 22: 4456-4462 (2004)), PD98059 (available, e.g., from Cell Signaling Technology), U0126 (available, for example, from Cell Signaling Technology), SL 327 (available, e.g., from Sigma-Aldrich), ARRY-162 (available, e.g., from Array Biopharma), PD184161 (see, e.g., Klein, et al., *Neoplasia* 8:1-8 (2006)), PD184352 (CI-1040) (see, e.g., Mattingly, et al., *The Journal of Pharmacology and Experimental Therapeutics* 316:456-465 (2006)), sunitinib (see, e.g., Voss, et al., US2008004287 incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluate in Phase I and II clinical trials for cancer (see, e.g., Rinehart, et al., *Journal of Clinical Oncology* 22(22):4456-4462 (2004)). Other MEK inhibitors being evaluated in clinical trials include PD184352 (see, e.g., English, et al., *Trends in Pharmaceutical Sciences* 23(1):40-45 (2002)), BAY 43-9006 (see, e.g., Chow, et al., *Cytometry (Communications in Clinical Cytometry)* 46:72-78 (2001)), PD-325901 (also PD0325901), GSK1120212, ARRY-438162, RDEA119, AZD6244 (also ARRY-142886 or ARRY-886), RO5126766, XL518 and AZD8330 (also ARRY-704). (See, e.g., information from the National Institutes of Health located on the World Wide Web at clinicaltrials.gov as well as information from the Nation Cancer Institute located on the World Wide Web at cancer.gov/clinicaltrials.

Exemplary ERK (i.e., ERK1 (also known as MAPK3) and/or ERK2 (also known as MAPK1)) inhibitors include PD98059 (see, e.g., Zhu, et al., *Oncogene* 23:4984-4992 (2004)), U0126 (see, Zhu, supra), FR180204 (see, e.g., Ohori, Drug News Perspective 21(5):245-250 (2008)), sunitinib (see, e.g., US2008004287 incorporated herein by reference), sorafenib, Vandetanib, pazopanib, Axitinib and PTK787.

Those of skill will appreciate that the concentration of the MEK/ERK pathway inhibitor will depend on which specific inhibitor is used. In particular embodiments, a combination of two or more different MEK/ERK pathway inhibitors can be used.

IV. Rho GTPase/ROCK Inhibitors

The present invention provides for uses and compositions comprising inhibitors of the Rho-GTPase/ROCK pathway. The pathway includes the downstream protein Myosin II, which is further downstream of ROCK (Rho-ROCK-Myosin II forms the pathway/axis). Thus, one can use any or all of a Rho GTPase inhibitor, a ROCK inhibitor, or a Myosin II inhibitor to achieve the effects described herein. Those of skill will appreciate that the concentration of the Rho-GTPase/ROCK pathway inhibitor will depend on which specific inhibitor is used. In additional embodiments, a combination of two or more different Rho-GTPase/ROCK pathway inhibitors can be used.

Any Rho GTPase should be effective in the methods and compositions of the invention. Inhibitors of Rho GTPase can include antibodies that bind, dominant negative variants of, and siRNA, microRNA, antisense nucleic acids, and other polynucleotides that target Rho GTPase. An exemplary Rho GTPase inhibitor is *Clostridium botulinum* C3 toxin.

Any Myosin II inhibitor should be effective in the methods and compositions of the invention. Inhibitors of Myosin II can include antibodies that bind, dominant negative variants of, and siRNA, microRNA, antisense nucleic acids, and other polynucleotides that target Myosin II. An exemplary Myosin II inhibitor is blebbistatin. The inventors have found that blebbistatin can be substituted for SB431542 (an ALK5 inhibitor), albeit with a reduced effect, in the mixtures and methods described in the example section. Other inhibitors include but are not limited to those described in U.S. Pat. No. 7,585,844.

"ROCK" used herein refers to a serine/threonine kinase that acts downstream of Rho. ROCK I (also referred to as ROK β or p160ROCK) and ROCK II (also referred to as ROK α or Rho kinase) are both regulated by RhoA. See e.g., Riento, K. and Ridley, A. J., *Nat. Rev. Mol. Cell. Biol.*, 4, 446-456 (2003). A "ROCK inhibitor" refers to agents that inhibit both or either of the ROCKs. Inhibitors of ROCK can include antibodies that bind, dominant negative variants of, and siRNA, microRNA, antisense nucleic acids, and other polynucleotides that target ROCK. Some exemplary ROCK inhibitors include, but are not limited to, those described in International Publication Nos.: WO98/06433, WO00/78351, WO01/17562, WO02/076976, WO02/076977, WO2003/062227, WO2003/059913, WO2003/062225, WO2002/076976, WO2004/039796, WO03/082808, WO05/035506, WO05/074643 and United States Patent Application Nos.: 2005/0209261, 2005/0192304, 2004/0014755, 2004/0002508, 2004/0002507, 2003/0125344 and 2003/0087919. ROCK inhibitors include, for example, (+)—(R)-trans-4-(1-aminoethyl)-N-(4-piridyl)cyclohexanecarboxamide dihydrochloride, or Wf536; 4—[(1R)-1-aminoethyl]-N-(4-piridyl)benzamide monohydrochloride or Fasudil; 5-(hexahydro-1H-1,4-diazepin-1-ylsulfonyl)isoquinoline hydrochloride or Compound 1; 4-[(trans-4-aminocyclohexyl)amino]-2,5-difluorobenzamide or Compound 2; 4-[(trans-4-aminocyclohexyl)amino]-5-chloro-2-fluorobenzamide or Compound 3; 2-[4-(1H-indazol-5-yl)phenyl]-2-propanamine dihydrochloride or Compound 4; N-(3-methoxybenzyl)-4-(4-piridyl)benzamide, Y-27632 (see, e.g., Ishizaki et al., *Mol. Pharmacol.* 57, 976-983 (2000); Narumiya et al., *Methods Enzymol.* 325, 273-284 (2000)), Fasudil (also referred to as HA1077) (for example, refer to Uenata et al., *Nature* 389: 990-994 (1997)), sc-3536 (see, e.g., Darenfed, H., et al. *Cell Motil. Cytoskeleton.* 64: 97-109, 2007), H-1152 (for example, refer to Sasaki et al., *Pharmacol. Ther.* 93: 225-232 (2002)), Wf-536 (for example, refer to Nakajima et al., *Cancer Chemother Pharmacol.* 52(4): 319-324 (2003)), Y-30141 (described in U.S. Pat. No. 5,478,838) and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof.

The above compounds may be made as acid addition salts with pharmaceutically acceptable inorganic acids or organic acids, as required. Examples of the acid addition salts include salts with mineral acids such as hydrochloric acid, hydrobromic acid, sulfuric acid, phosphoric acid and the like; salts with organic carboxylic acids such as formic acid, acetic acid, fumaric acid, maleic acid, oxalic acid, citric acid, malic acid, tartaric acid, aspartic acid and glutamic acid; and salts with sulfonic acids such as methanesulfonic acid, benzenesulfonic acid, p-toluenesulfonic acid, hydroxybenzenesulfonic acid, dihydroxybenzene sulfonic acid and the like.

The compounds and acid addition salts thereof may be an anhydride, hydrate or solvate thereof.

To practice the present invention ROCK inhibitors generally are suitable without limitation so long as an inhibitor can inhibit the function of Rho-kinase (ROCK), and suitable inhibitors include Y-27632 (for example, refer to Ishizaki et al., *Mol. Pharmacol.* 57, 976-983 (2000); Narumiya et al., *Methods Enzymol.* 325, 273-284 (2000)), sc-3536 (see, e.g., Darenfed, H., et al. *Cell Motil. Cytoskeleton.* 64: 97-109, 2007), Fasudil (also referred to as HA1077) (for example, refer to Uenata et al., *Nature* 389: 990-994 (1997)), H-1152 (for example, refer to Sasaki et al., *Pharmacol. Ther.* 93: 225-232 (2002)), Wf-536 (for example, refer to Nakajima et al., *Cancer Chemother Pharmacol.* 52(4): 319-324 (2003)), Y-30141 (described in U.S. Pat. No. 5,478,838) and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in the present invention (for example, refer to United State Patent Application Nos. 20050209261, 20050192304, 20040014755, 20040002508, 20040002507, 20030125344 and 20030087919, and International Patent Publication Nos. 2003/062,227, 2003/059,913, 2003/062,225, 2002/076,976 and 2004/039,796). In the present invention, a combination of one or two or more of the ROCK inhibitors can also be used Additional ROCK inhibitors include, e.g., HA1100, 3-(4-Pyridyl)-1H-indole and N-(4-Pyridyl)-N'—(2,4,6-trichlorophenyl) urea, each of which is commercially available (e.g., from Alexis Biochemicals (Plymouth Meeting, Pa.).

In some embodiments, ROCK inhibitors have the formula:

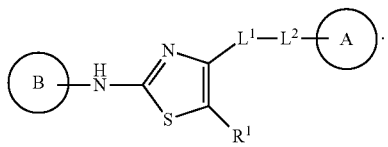
(I)

In Formula (I), ring A is a substituted or unsubstituted cycloalkyl, substituted or unsubstituted heterocycloalkyl, substituted or unsubstituted aryl, or substituted or unsubstituted heteroaryl. Ring B is a substituted or unsubstituted heterocycloalkyl, or substituted or unsubstituted heteroaryl.

$L^1$ is —C(O)—$NR^2$— or —$NR^2$—C(O)—. $L^2$ is a bond, substituted or unsubstituted alkylene or substituted or unsubstituted heteroalkylene.

$R^1$ and $R^2$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, ring A is a substituted or unsubstituted aryl. Ring A may also be a substituted or unsubstituted phenyl.

In other embodiments, ring B is a substituted or unsubstituted heterocycloalkyl, or substituted or unsubstituted heteroaryl. Ring B may also be a substituted or unsubstituted heteroaryl. In still other embodiments, ring B is a substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, or substituted or unsubstituted dimethylhydantoin.

$L^2$ may be substituted or unsubstituted $C_1$-$C_{10}$ alkyl. In some embodiments, $L^2$ is unsubstituted $C_1$-$C_{10}$ alkyl. $L^2$ may also be substituted or unsubstituted methylene (e.g. unsubstituted methylene).

$R^2$ may be hydrogen. $R^1$ may be hydrogen or unsubstituted $C_1$-$C_{10}$ alkyl. In some embodiments, $R^1$ is simply hydrogen.

In some embodiments of Formula (I), ring A is substituted or unsubstituted aryl, ring B is substituted or unsubstituted heteroaryl, $R^1$ is hydrogen, and $L^2$ is unsubstituted $C_1$-$C_{10}$ alkyl.

In another embodiment, the ROCK inhibitor has the formula:

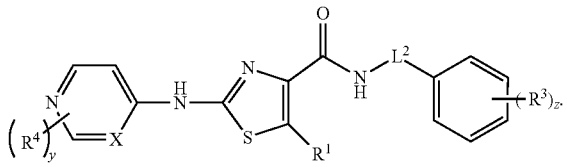
(II)

In Formula (II), y is an integer from 0 to 3 and z is an integer from 0 to 5. X is —N=, —CH= or —$CR^4$=. $R^1$ and $L^2$ are as defined above in the definitions of Formula (I).

$R^3$, $R^4$ and $R^5$ are independently —CN, —S(O)n$R^6$, —$NR^7R^8$, —C(O)$R^9$, —$NR^{10}$—C(O)$R^{11}$, —$NR^{12}$—C(O)—$OR^{13}$, —C(O)$NR^{14}R^{15}$, —$NR^{16}$S(O)$_2R^{17}$, —$OR^{18}$, —S(O)$_2NR^{19}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 2, wherein if z is greater than 1, two $R^3$ moieties are optionally joined together to form a substituted or unsubstituted cycloalkyl, substituted or unsubstituted heterocycloalkyl, substituted or unsubstituted aryl, or substituted or unsubstituted heteroaryl.

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, unsubstituted cycloalkyl, substituted or unsubstituted heterocycloalkyl, substituted or unsubstituted aryl, or substituted or unsubstituted heteroaryl.

In some embodiments, $L^2$ is substituted or unsubstituted $C_1$-$C_{10}$ alkyl. $L^2$ may also be unsubstituted $C_1$-$C_{10}$ alkyl. Alternatively, $L^2$ is substituted or unsubstituted methylene (e.g. unsubstituted methylene).

In other embodiments, X is —N= or —CH=. The symbol z may be 2. In still other embodiments, two $R^3$ moieties at adjacent vertices are joined together to from a substituted or unsubstituted heterocycloalkyl. The symbol z may also be 1. The symbol y may be 0 or 1.

$R^3$ may be —$OR^{18}$. $R^{18}$ may be hydrogen or unsubstituted $C_1$-$C_{10}$ alkyl.

In some embodiments, $L^2$ is substituted or unsubstituted methylene (e.g. substituted methylene), X is —N= or —CH=, $R^1$ is hydrogen, and y and z are 0.

In other embodiments, the compounds has the formula:

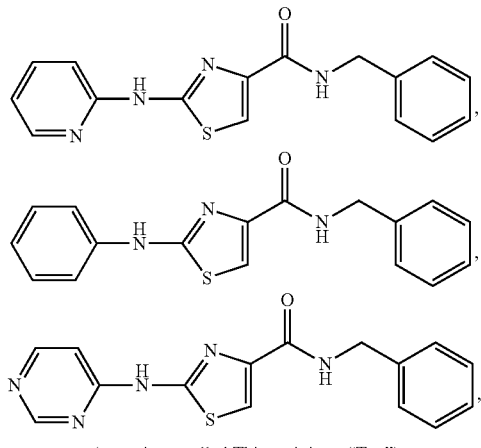

(sometimes called Thiazovivin or "Tzv")

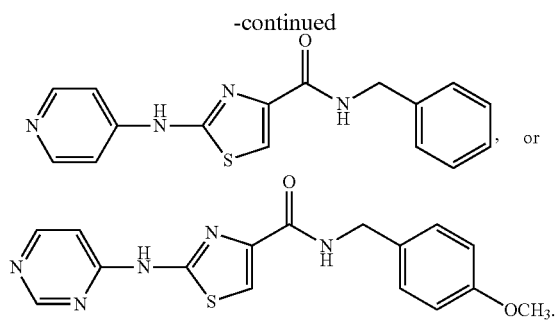

V. GSK3 Inhibitors

In various embodiments, one or more GSK3 inhibitors can be included in the methods, mixtures and kits of the invention. The inventors have found that the inclusion of GSK3 inhibitors with at least a TGFβ receptor/ALK5 inhibitor, preferably in combination with a MEK/ERK pathway inhibitor and in particular embodiments, a Rho GTPase/ROCK inhibitor. Inhibitors of GSK3 can include antibodies that bind, dominant negative variants of, and siRNA, microRNA, antisense nucleic acids, and other polynucleotides that target GSK3. Specific examples of GSK3 inhibitors include, but are not limited to, Kenpaullone, 1-Azakenpaullone, CHIR99021, CHIR98014, AR-A014418 (see, e.g., Gould, et al., *The International Journal of Neuropsychopharmacology* 7:387-390 (2004)), CT 99021 (see, e.g., Wagman, *Current Pharmaceutical Design* 10:1105-1137 (2004)), CT 20026 (see, Wagman, supra), SB216763 (see, e.g., Martin, et al., *Nature Immunology* 6:777-784 (2005)), AR-A014418 (see, e.g., Noble, et al., *PNAS* 102:6990-6995 (2005)), lithium (see, e.g., Gould, et al., *Pharmacological Research* 48: 49-53 (2003)), SB 415286 (see, e.g., Frame, et al., *Biochemical Journal* 359:1-16 (2001)) and TDZD-8 (see, e.g., Chin, et al., *Molecular Brain Research*, 137(1-2): 193-201 (2005)). Further exemplary GSK3 inhibitors available from Calbiochem (see, e.g., Dalton, et al., WO2008/094597, herein incorporated by reference), include but are not limited to BIO (2′Z,3′£)-6-Bromoindirubin-3′-oxime (GSK3 Inhibitor IX); BIO-Acetoxime (2′Z,3′E)-6-Bromoindirubin-3′-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N′-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWSl 19 pyrrolopyrimidine compound (GSK3beta Inhibitor XII); L803 H-KEAP-PAPPQSpP-NH$_2$ (SEQ ID NO:47) or its myristoylated form (GSK3beta Inhibitor XIII); 2-Chloro-1-(4,5-dibromo-thiophen-2-yl)-ethanone (GSK3beta Inhibitor VI); AR-AO144-18; SB216763; and SB415286. Residues of GSK3b that interact with inhibitors have been identified. See, e.g., Bertrand et al., *J. Mol Biol.* 333(2): 393-407 (2003). GSK3 inhibitors can activate, for example, the Wnt/β-catenin pathway. Many of β-catenin downstream genes co-regulate pluripotency gene networks. For example, a GSK inhibitor activates cMyc expression as well as enhances its protein stability and transcriptional activity. Thus, in some embodiments, GSK3 inhibitors can be used to stimulate endogenous MYC polypeptide expression in a cell, thereby eliminating the need for MYC expression to induce pluripotency.

Those of skill will appreciate that the concentration of the GSK3 inhibitor will depend on which specific inhibitor is used. In certain embodiments, a combination of two or more different GSK3 inhibitors can be used.

VI. Methods of Inducing Pluripotency

To date, a large number of different methods and protocols have been established for inducing non-pluripotent mammalian cells into induced pluripotent stem cells (iPSCs). It is believed that the agents described herein can be used in combination with essentially any protocol for generating iPSCs and thereby improve the efficiency of the protocol. Thus, the present invention provides for incubation of non-pluripotent cells with at least a TGFβ receptor/ALK5 inhibitor, preferably in combination with a MEK/ERK pathway inhibitor, and in particular embodiments, a Rho GTPase/ROCK inhibitor in combination with any protocol for generating iPSCs. A selection of protocols is described below and each is believed to be combinable with the agents of the invention to improve efficiency of the protocol.

The improvement in efficiency of an iPSC generation protocol will depend on the protocol and which agents of the invention are used. In some embodiments, the efficiency is improved by at least 10%, 20%, 50%, 75%, 100%, 150%, 200%, 300% or more compared to the same protocol without inclusion of the agents of the invention (i.e., TGFβ receptor/ALK5 inhibitor, MEK/ERK pathway inhibitor and Rho GTPase/ROCK inhibitor). Efficiency is measured with regard to improvement of the number of iPSCs generated in a particular time frame or the speed by which iPSCs are generated.

Studies have shown that retroviral transduction of mouse fibroblasts with four transcription factors that are highly expressed in ESCs (Oct-3/4, Sox2, KLF4 and c-Myc) generate induced pluripotent stem (iPS) cells. See, Takahashi, K. & Yamanaka, S. *Cell* 126, 663-676 (2006); Okita, K., Ichisaka, T. & Yamanaka, S. *Nature* 448, 313-317 (2007); Wernig, M. et al. *Nature* 448, 318-324 (2007); Maherali, N. et al. *Cell Stem Cell* 1, 55-70 (2007); Meissner, A., Wernig, M. & Jaenisch, R. *Nature Biotechnol.* 25, 1177-1181 (2007); Takahashi, K. et al. *Cell* 131, 861-872 (2007); Yu, J. et al. *Science* 318, 1917-1920 (2007); Nakagawa, M. et al. *Nature Biotechnol.* 26, 101-106 (2007); Wernig, M., Meissner, A., Cassady, J. P. & Jaenisch, R. *Cell Stem Cell.* 2, 10-12 (2008). iPS cells are similar to ESCs in morphology, proliferation, and pluripotency, judged by teratoma formation and chimaera contribution.

As noted above, while the original protocol involved introduction of four transcription factors into non-pluripotent cells, it has been more recently discovered that some transcription factors can be omitted. Thus, in some embodiments, the protocols involves introducing one, two or three of an Oct polypeptide, a Klf polypeptide, a Myc polypeptide, and a Sox polypeptide to non-pluripotent cells under conditions that allow for the non-pluripotent cells to become iPSCs. For example, each of Maherali and Konrad Hochedlinger, "Tgfβ Signal Inhibition Cooperates in the Induction of iPSCs and Replaces Sox2 and cMyc" *Current Biology* (2009) and WO/2009/117439 describe protocols that do not require all four transcription factors to induce pluripotency. Moreover, the inventors have found that iPSCs can be generated by introducing Oct4 alone into cells and incubating the cells with a TGFβ receptor/ALK5 inhibitor, a MEK/ERK pathway inhibitor, a Rho GTPase/ROCK inhibitor, and a histone deacetylase (HDAC) inhibitor. For example, introduction of exogenous Oct4 into mammalian cells, in the presence of a sufficient amount of SB431542, PD0325901, Tzv, and valproic acid or sodium butyrate, successfully generated iPSC cells.

Exemplary HDAC inhibitors can include antibodies that bind, dominant negative variants of, and siRNA and antisense nucleic acids that target one or more HDACs. HDAC inhibitors include, but are not limited to, TSA (trichostatin A) (see, e.g., Adcock, *British Journal of Pharmacology* 150:829-831 (2007)), VPA (valproic acid) (see, e.g., Munster, et al., *Journal of Clinical Oncology* 25:18S (2007): 1065), sodium butyrate (NaBu) (see, e.g., Han, et al., *Immunology Letters* 108:143-150 (2007)), SAHA (suberoylanilide hydroxamic acid or vorinostat) (see, e.g., Kelly, et al., *Nature Clinical Practice Oncology* 2:150-157 (2005)), sodium phenylbutyrate (see, e.g., Gore, et al., *Cancer Research* 66:6361-6369 (2006)), depsipeptide (FR901228, FK228) (see, e.g., Zhu, et al., *Current Medicinal Chemistry* 3(3):187-199 (2003)), trapoxin (TPX) (see, e.g., Furumai, et al., *PNAS* 98(1):87-92 (2001)), cyclic hydroxamic acid-containing peptide 1 (CHAP1) (see, Furumai supra), MS-275 (see, e.g., Carninci, et al., WO2008/126932, incorporated herein by reference)), LBH589 (see, e.g., Goh, et al., WO2008/108741 incorporated herein by reference) and PXD101 (see, Goh, supra). In general, at the global level, pluripotent cells have more histone acetylation, and differentiated cells have less histone acetylation. Histone acetylation is also involved in regulation of histone and DNA methylation. In some embodiments, HDAC inhibitors facilitate activation of silenced pluripotency genes.

To address the safety issues that arise from target cell genomes harboring integrated exogenous sequences, a number of modified genetic protocols have been further developed. These protocols produce iPS cells with potentially reduced risks, and include non-integrating adenoviruses to deliver reprogramming genes (Stadtfeld, M., et al. (2008) *Science* 322, 945-949), transient transfection of reprogramming plasmids (Okita, K., et al. (2008) *Science* 322, 949-953), piggyBac transposition systems (Woltjen, K., et al. (2009). *Nature* 458, 766-770, Kaji, K., et al. (2009) *Nature* 458, 771-775), Cre-excisable viruses (Soldner, F., et al. (2009) *Cell* 136, 964-977), and oriP/EBNA1-based episomal expression system (Yu, J., et al. (2009) *Science* DOI: 10.1126). Furthermore, strategies of exploiting endogenous gene expression in certain cell types also allowed easier reprogramming and/or with less required exogenous genes (Shi, Y., et al. (2008b). *Cell Stem Cell* 2, 525-528; Aasen, T., et al. (2008) *Nat Biotechnol* 26, 1276-1284; Kim, J. B., et al. (2008). *Nature* 454, 646-650). Moreover, small molecules have been identified that enhance reprogramming efficiency and replace certain reprogramming factors (Shi, Y., et al. (2008) *Cell Stem Cell* 2, 525-528, Shi, Y., et al. (2008) *Cell Stem Cell* 3, 568-574, Li, W., et al. (2009) *Cell Stem Cell* 4, 16-19; Huangfu, D., et al. (2008) *Nat Biotechnol* 26, 1269-1275, Huangfu, D., et al. (2008) *Nat Biotechnol* 26, 795-797).

Moreover, recently, it has been shown that transcription factors can be delivered as exogenous protein to non-pluripotent cells, to generate iPSCs. See, e.g., WO/2009/117439; Zhou et al., *Cell Stem Cell* 4:381-384 (2009). One can introduce an exogenous polypeptide (i.e., a protein provided from outside the cell and/or that is not produced by the cell) into the cell by a number of different methods that do not involve introduction of a polynucleotide encoding the polypeptide. Thus, in some embodiments, non-pluripotent cells are contacted with a TGFβ receptor/ALK5 inhibitor, preferably in combination with a MEK/ERK pathway inhibitor, and in particular embodiments, a Rho GTPase/ROCK inhibitor and one or more exogenous transcription factor proteins, e.g., one, two, three or all four of an Oct polypeptide, a Klf polypeptide, a Myc polypeptide, and a Sox polypeptide.

A variety of ways have been described for introducing the relevant protein factors into the target cells. In one embodiment, introduction of a polypeptide into a cell can comprise introduction of a polynucleotide comprising one or more expression cassettes into a cell and inducing expression, thereby introducing the polypeptides into the cell by transcription and translation from the expression cassette.

Alternatively, one or more proteins can simply be cultured in the presence of target cells under conditions to allow for introduction of the proteins into the cell. See, e.g., Zhou H et al., *Generation of induced pluripotent stem cells using recombinant proteins. Cell Stem Cell.* 2009 May 8; 4(5): 381-4. In some embodiments, the exogenous proteins comprise the transcription factor polypeptide of interest linked (e.g., linked as a fusion protein or otherwise covalently or non-covalently linked) to a polypeptide that enhances the ability of the transcription factor to enter the cell (and in some embodiments the cell nucleus).

Examples of polypeptide sequences that enhance transport across membranes include, but are not limited to, the *Drosophila* homeoprotein antennapedia transcription protein (AntHD) (Joliot et al., *New Biol.* 3: 1121-34, 1991; Joliot et al., *Proc. Natl. Acad. Sci. USA,* 88: 1864-8, 1991; Le Roux et al., *Proc. Natl. Acad. Sci. USA,* 90: 9120-4, 1993), the herpes simplex virus structural protein VP22 (Elliott and O'Hare, *Cell* 88: 223-33, 1997); the HIV-1 transcriptional activator TAT protein (Green and Loewenstein, *Cell* 55: 1179-1188, 1988; Frankel and Pabo, *Cell* 55: 1 289-1193, 1988); delivery enhancing transporters such as described in U.S. Pat. No. 6,730,293 (including but not limited to an peptide sequence comprising at least 7-25 contiguous arginines); and commercially available Penetratin™ 1 peptide, and the Diatos Peptide Vectors ("DPVs") of the Vectocell® platform available from Daitos S. A. of Paris, France. See also, WO/2005/084158 and WO/2007/123667 and additional transporters described therein. Not only can these proteins pass through the plasma membrane but the attachment of other proteins, such as the transcription factors described herein, is sufficient to stimulate the cellular uptake of these complexes.

In some embodiments, the transcription factor polypeptides described herein are exogenously introduced as part of a liposome, or lipid cocktail such as commercially available Fugene6 and Lipofectamine). In another alternative, the transcription factor proteins can be microinjected or otherwise directly introduced into the target cell.

As discussed in the Examples of WO/2009/117439, incubation of cells with the transcription factor polypeptides of the invention for extended periods is toxic to the cells. Therefore, the present invention provides for intermittent incubation of non-pluripotent mammalian cells with one or more of a Klf polypeptide, an Oct polypeptide, a Myc polypeptide, and/or a Sox polypeptide, with intervening periods of incubation of the cells in the absence of the one or more polypeptides. In some embodiments, the cycle of incubation with and without the polypeptides can be repeated for 2, 3, 4, 5, 6, or more times and is performed for sufficient lengths of time (i.e., the incubations with and without proteins) to achieve the development of pluripotent cells. Various agents (e.g., MEK/ERK pathway inhibitor and/or GSK3 inhibitor and/or TGFbeta/ALK5 inhibitor and/or Rho GTPase/ROCK pathway inhibitor) can be included to improve efficiency of the method.

The various inhibitors (e.g., TGFβ receptor/ALK5 inhibitor, MEK/ERK pathway inhibitor, and in particular embodiments, Rho GTPase/ROCK inhibitor, and/or GSK3 inhibitor, etc.) can be contacted to non-pluripotent cells either prior to, simultaneously with, or after delivery of, programming transcription factors (for example, delivered via expression cassette or as proteins). For convenience, the day the reprogramming factors are delivered is designated "day 1". In some embodiments, the inhibitors are contacted to cells in aggregate (i.e., as a "cocktail") at about days 3-7 and continued for 7-14 days. Alternatively, in some embodiments, the cocktail is contacted to the cells at day 0 (i.e., a day before the preprogramming factors) and incubated for about 14-30 days.

In other embodiments, different inhibitors are added at different times. In some embodiments, at 1-7 days after the delivery of the reprogramming factors, the cells are contacted with compound combination of an TGFβ receptor/ALK5 inhibitor (e.g., SB431542) and a ROCK inhibitor for 1-8 days, followed by contacting the cells with the TGFβ receptor/ALK5 inhibitor, ROCK inhibitor and a MEK/ERK pathway inhibit (e.g., PD0325901) for 1-8 days. This can be optionally followed by contact with the TGFβ receptor/ALK5 inhibitor and MEK/ERK pathway inhibitor (but not necessarily the ROCK inhibitor) for 1-4 days, followed by contact with the MEK/ERK pathway inhibitor (but not the TGFβ receptor/ALK5 inhibitor or ROCK inhibitor), and optionally finally with basal (e.g., basal human) ES medium without inhibitors for 1-4 days. Other combinations can also be employed.

IV. Transformation

This invention employs routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

In some embodiments, the species of cell and protein to be expressed is the same. For example, if a mouse cell is used, a mouse ortholog is introduced into the cell. If a human cell is used, a human ortholog is introduced into the cell.

It will be appreciated that where two or more proteins are to be expressed in a cell, one or multiple expression cassettes can be used. For example, where one expression cassette expresses multiple polypeptides, a polycistronic expression cassette can be used.

A. Plasmid Vectors

In certain embodiments, a plasmid vector is contemplated for use to transform a host cell. In general, plasmid vectors containing replicon and control sequences which are derived from species compatible with the host cell are used in connection with these hosts. The vector can carry a replication site, as well as marking sequences which are capable of providing phenotypic selection in transformed cells.

B. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

i. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a ~36 kb, linear, double-stranded DNA virus, allows substitution of large pieces of adenoviral DNA with foreign sequences up to 7 kb (Grunhaus et al., Seminar in Virology, 200(2):535-546, 1992)).

ii. AAV Vectors

The nucleic acid may be introduced into the cell using adenovirus assisted transfection. Increased transfection efficiencies have been reported in cell systems using adenovirus coupled systems (Kelleher and Vos, Biotechniques, 17(6): 1110-7, 1994; Cotten et al., *Proc Natl Acad Sci USA*, 89(13):6094-6098, 1992; Curiel, *Nat Immun*, 13(2-3):141-64, 1994). Adeno-associated virus (AAV) is an attractive vector system as it has a high frequency of integration and it can infect non-dividing cells, thus making it useful for delivery of genes into mammalian cells, for example, in tissue culture (Muzyczka, *Curr Top Microbiol Immunol*, 158:97-129, 1992) or in vivo. Details concerning the generation and use of rAAV vectors are described in U.S. Pat. Nos. 5,139,941 and 4,797,368, each incorporated herein by reference.

iii. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller et al., *Am. J. Clin. Oncol.*, 15(3):216-221, 1992).

In order to construct a retroviral vector, a nucleic acid (e.g., one encoding gene of interest) is inserted into the viral genome in the place of certain viral sequences to produce a virus that is replication-defective. To produce virions, a packaging cell line containing the gag, pol, and env genes but without the LTR and packaging components is constructed (Mann et al., *Cell*, 33:153-159, 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubinstein, In: *Vectors: A survey of molecular cloning vectors and their uses*, Rodriguez and Denhardt, eds., Stoneham: Butterworth, pp. 494-513, 1988; Temin, In: *Gene Transfer*, Kucherlapati (ed.), New York: Plenum Press, pp. 149-188, 1986; Mann et al., *Cell*, 33:153-159, 1983). The media containing the recombinant retroviruses is then collected, optionally concentrated, and used for gene transfer. Retroviral vectors are able to infect a broad variety of cell types. However, integration and stable expression typically involves the division of host cells (Paskind et al., *Virology*, 67:242-248, 1975).

Lentiviruses are complex retroviruses, which, in addition to the common retroviral genes gag, pol, and env, contain other genes with regulatory or structural function. Lentiviral vectors are well known in the art (see, for example, Naldini et al., *Science*, 272(5259):263-267, 1996; Zufferey et al., *Nat Biotechnol*, 15(9):871-875, 1997; Blomer et al., *J Virol.*, 71(9):6641-6649, 1997; U.S. Pat. Nos. 6,013,516 and 5,994, 136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

iv. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., *Proc. Nat'l Acad. Sci. USA*, 86:9079-9083, 1989). Using antibodies against major histocompatibility complex class I and class II antigens, they demonstrated the infection of a variety of human cells that bore those surface antigens with an ecotropic virus in vitro (Roux et al., 1989).

C. Vector Delivery and Cell Transformation

Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art. Such methods include, but are not limited to, direct delivery of DNA such as by ex vivo transfection (Wilson et al., *Science*, 244:1344-1346, 1989, Nabel and Baltimore, *Nature* 326: 711-713, 1987), optionally with Fugene6 (Roche) or Lipofectamine (Invitrogen), by injection (U.S. Pat. Nos. 5,994, 624, 5,981,274, 5,945,100, 5,780,448, 5,736,524, 5,702,932, 5,656,610, 5,589,466 and 5,580,859, each incorporated herein by reference), including microinjection (Harland and Weintraub, *J. Cell Biol.*, 101:1094-1099, 1985; U.S. Pat. No. 5,789,215, incorporated herein by reference); by electroporation (U.S. Pat. No. 5,384,253, incorporated herein by reference; Tur-Kaspa et al., *Mol. Cell Biol.*, 6:716-718, 1986; Potter et al., *Proc. Nat'l Acad. Sci. USA*, 81:7161- 7165, 1984); by calcium phosphate precipitation (Graham and Van Der Eb, *Virology*, 52:456-467, 1973; Chen and Okayama, *Mol. Cell Biol.*, 7(8):2745-2752, 1987; Rippe et al., *Mol. Cell Biol.*, 10:689-695, 1990); by using DEAE-dextran followed by polyethylene glycol (Gopal, *Mol. Cell Biol.*, 5:1188-1190, 1985); by direct sonic loading (Fechheimer et al., *Proc. Nat'l Acad. Sci. USA*, 84:8463-8467, 1987); by liposome mediated transfection (Nicolau and Sene, *Biochim. Biophys. Acta*, 721:185-190, 1982; Fraley et al., *Proc. Nat'l Acad. Sci. USA*, 76:3348-3352, 1979; Nicolau et al., *Methods Enzymol.*, 149:157-176, 1987; Wong et al., *Gene*, 10:87-94, 1980; Kaneda et al., *Science*, 243:375- 378, 1989; Kato et al., *J Biol. Chem.*, 266:3361-3364, 1991) and receptor-mediated transfection (Wu and Wu, *Biochemistry*, 27:887-892, 1988; Wu and Wu, *J. Biol. Chem.*, 262: 4429-4432, 1987); and any combination of such methods, each of which is incorporated herein by reference.

VII. Mixtures

The present invention provides for mixtures that improve the efficiency of generation of iPSCs For example, the invention provides for mixtures of a TGFβ receptor/ALK5 inhibitor, a MEK/ERK pathway inhibitor, a Rho GTPase/ROCK inhibitor, in particular embodiments, with mammalian cells. For example, the mixtures can be included in cell culture media, with or without cells. The contents of cell culture media are generally known in the art. Exemplary cell culture media are described in detail in the Examples. Generally, cell cultures comprising mammalian cells and agents of the invention (TGFβ receptor/ALK5 inhibitor, a MEK/ERK pathway inhibitor, and a Rho GTPase/ROCK inhibitor) will initially contain all or substantially all non-pluripotent cells. However, over time, especially under the conditions of the protocols described here, a portion of the cells will become pluripotent (i.e., iPSCs).

Cells to be induced to pluripotency can be cultured according to any method known in the art. General guidelines for culture conditions to generate iPSCs can be found in, e.g., Maherali, et al., *Cell Stem Cell* 3:595-605 (2008).

In some embodiments, the cells are cultured in contact with feeder cells. Exemplary feeder cells include, but are not limited to fibroblast cells, e.g., mouse embryonic fibroblast (MEF) cells. Methods of culturing cells on feeder cells are known in the art.

In some embodiments, the cells are cultured in the absence of feeder cells. Cells, for example, can be attached directly to a solid culture surface (e.g., a culture plate), e.g., via a molecular tether. The inventors have found that culturing cells induced to pluripotency have a much greater efficiency of induction to pluripotency (i.e., a greater portion of cells achieve pluripotency) when the cells are attached directly to the solid culturing surface compared the efficiency of otherwise identically-treated cells that are cultured on feeder cells. Exemplary molecular tethers include, but are not limited to, Matrigel®, an extracellular matrix (ECM), ECM analogs, laminin, fibronectin, or collagen. Those of skill in the art however will recognize that this is a non-limiting list and that other molecules can be used to attach cells to a solid surface. Methods for initial attachment of the tethers to the solid surface are known in the art.

As described herein, in some embodiments, the mixtures of the invention can include or exclude mammalian cells (including pluripotent or non-pluripotent cells), and one or more of a HDAC inhibitor, GSK3 inhibitor, or an L-type Ca channel agonist; an activator of the cAMP pathway; a DNA methyltransferase (DNMT) inhibitor; a nuclear receptor ligand, e.g., as described in PCT WO/2009/117439.

VIII. Kits

The present invention also provides kits, e.g., for use in generating induced pluripotent stem cells. Such kits can comprise any or all of the reagents described herein, including but not limited to: a TGFβ receptor/ALK5 inhibitor, a MEK/ERK pathway inhibitor, and/or a Rho GTPase/ROCK inhibitor, as described herein. These three agents, or subsets thereof, can be present in the kit in separate vials, or together as a mixture. The kits of the invention can also include, one or more of an HDAC inhibitor, a GSK3 inhibitor, or an L-type Ca channel agonist; an activator of the cAMP pathway; a DNA methyltransferase (DNMT) inhibitor; and a nuclear receptor ligand.

In one embodiment, the kits of the invention will include one or more types of mammalian (e.g., human, mouse, rat, etc.) cells and/or cell culture media.

In a particular embodiment, the kits of the invention will include one or more polynucleotides comprising expression cassettes for expression of one or more of Oct polypeptide, a Klf polypeptide, a Myc polypeptide, and a Sox polypeptide. In addition, or alternatively, the kits can comprise one or more isolated transcription factor proteins, e.g., one, two, three or all four of an Oct polypeptide, a Klf polypeptide, a Myc polypeptide, and a Sox polypeptide. In another particular embodiment, the transcription factor proteins can be fused to a polypeptide sequence for enhancing transport of the transcription factor proteins across cell membranes.

VI. Uses for Pluripotent Cells

The present invention allows for the further study and development of stem cell technologies, including but not limited to, prophylactic or therapeutic uses. For example, in some embodiments, cells of the invention (either pluripotent cells or cells induced to differentiate along a desired cell fate) are introduced into individuals in need thereof, including but not limited to, individuals in need of regeneration of an organ, tissue, or cell type. In some embodiments, the cells are originally obtained in a biopsy from an individual; induced into pluripotency as described herein, optionally induced to differentiate (for examples into a particular desired progenitor cell) and then transplanted back into the individual. In some embodiments, the cells are genetically modified prior to their introduction into the individual.

In some embodiments, the pluripotent cells generated according to the methods of the invention are subsequently induced to form, for example, hematopoietic (stem/progenitor) cells, neural (stem/progenitor) cells (and optionally, more differentiated cells, such as subtype specific neurons, oligodendrocytes, etc), pancreatic cells (e.g., endocrine progenitor cell or pancreatic hormone-expressing cells), hepatocytes, cardiovascular (stem/progenitor) cells (e.g., cardiomyocytes, endothelial cells, smooth muscle cells), retinal cells, etc.

A variety of methods are known for inducing differentiation of pluripotent stem cells into desired cell types. A non-limiting list of recent patent publications describing methods for inducing differentiation of stem cells into various cell fates follows: U.S. Patent Publication Nos.: 2007/0281355; 2007/0269412; 2007/0264709; 2007/0259423; 2007/0254359; 2007/0196919; 2007/0172946; 2007/0141703; 2007/0134215.

A variety of diseases may be ameliorated by introduction, and optionally targeting, of pluripotent cells of the invention to a particular injured tissue. Examples of disease resulting from tissue injury include, but are not limited to, neurodegeneration disease, cerebral infarction, obstructive vascular disease, myocardial infarction, cardiac failure, chronic obstructive lung disease, pulmonary emphysema, bronchitis, interstitial pulmonary disease, asthma, hepatitis B (liver damage), hepatitis C (liver damage), alcoholic hepatitis (liver damage), hepatic cirrhosis (liver damage), hepatic insufficiency (liver damage), pancreatitis, diabetes mellitus, Crohn disease, inflammatory colitis, IgA glomerulonephritis, glomerulonephritis, renal insufficiency, decubitus, burn, sutural wound, laceration, incised wound, bite wound, dermatitis, cicatricial keloid, keloid, diabetic ulcer, arterial ulcer, and venous ulcer.

In one embodiment, iPSCs can be used in various assays and screen to identify molecules that modulate their function, including but not limited to promoting iPSC survival and/or differentiation.

EXAMPLES

The following examples are offered to illustrate, but not to limit the claimed invention.

Example 1: A Chemical Platform for Improved Induction of Human iPSCs

Mesenchymal type fibroblasts reprogrammed with the "four-factors" (OCT4, SOX2, KLF4 & c-MYC; 4TFs hereafter) underwent dramatic morphological changes that resulted in iPSCs with distinct cell polarity, boundaries and cell-cell interactions. The reprogrammed cells expressed E-cadherin, a marker for epithelial cells (Hay, E. D., *Acta Anat.* (*Basel*) 154, 8-20 (1995)), which is also highly expressed in human embryonic stem cells (hESCs). We reasoned that factors that promote the mesenchymal to epithelial transition (MET), such as TGFβ pathway antagonists, would have a direct impact on the reprogramming process. In addition, MEK-ERK pathway inhibition was previously shown to play an important role in various steps of reprogramming (Chen, S. et al., *Proc. Natl. Acad. Sci. USA* 104, 10482-87 (2007); Shi, Y. et al., *Cell Stem Cell* 2, 525-8 (2008)). Furthermore, factors promoting cell survival could also be beneficial in improving reprogramming efficiency. Consequently, we focused on small molecules that can regulate these three processes and pathways, as small molecules have many advantages (Feng, B. et al., *Cell Stem Cell* 4, 301-12 (2009); Shi, Y. et al., *Cell Stem Cell* 2, 525-8 (2008); Xu, Y. et al., *Nature* 453, 338-44 (2008)) in studying biological processes and are a safer choice than genetic manipulation. Here we describe a simple chemical platform that substantially enhances generation of fully reprogrammed human iPSCs from fibroblasts through a much faster and more efficient process.

We tested known inhibitors of the TGFβ receptor and MEK on $1\times10^4$ (Feng, B. et al., *Cell Stem Cell* 4, 301-12 (2009)) human primary fibroblasts (CRL2097 or BJ) that were retrovirally transduced with the 4TFs, for their effect on reprogramming kinetics and efficiency (see FIG. 1a for details). On day 7 (D7) post-infection, the compounds were added, individually or in combinations, and the cultures were examined for iPSCs over the next 1-3 weeks.

On day 7 post-treatment (D14), we observed the strongest effect in the cultures treated with a combination of ALK5 inhibitor SB431542 (2 μM) and MEK inhibitor PD0325901

Figure 1E:
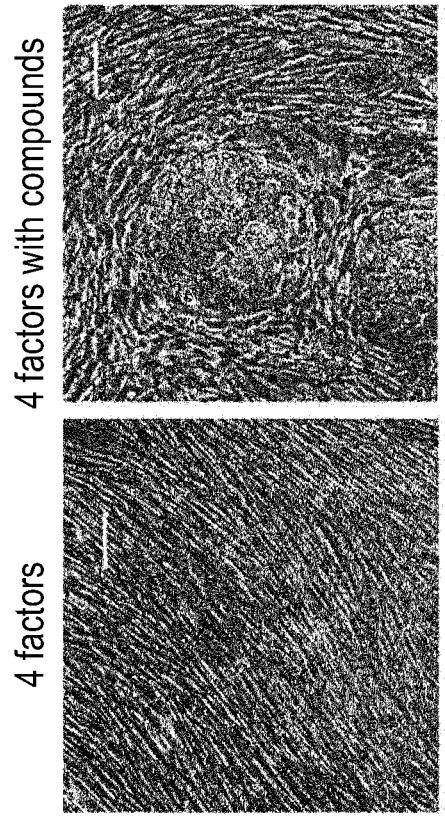
Figure 1F:
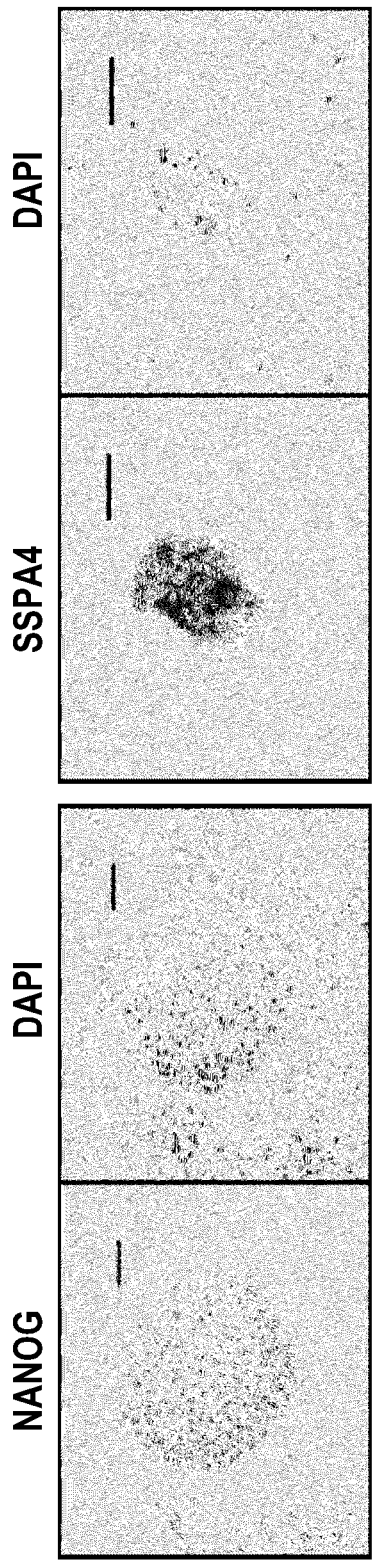

(0.5 µM), which resulted in ~45 large ALP⁺ colonies (FIG. 1b) with characteristic hESC-like morphology, of which over 24 colonies were TRA-1-81⁺ (FIG. 1d), and about 6-10 colonies stained positive for SSEA4 and NANOG, a mature pluripotency factor that is not ectopically introduced (FIGS. 1e and 10. Moreover, the treated cultures showed high level expression of endogenous mRNA for the pluripotency genes (FIG. 1c). In contrast, no NANOG colonies were observed in the untreated control cultures (FIG. 1e & FIG. 4a) or in cultures that were treated with PD0325901 alone (FIG. 4a). However, in the cultures treated with only SB431542, we still observed 1-2 ALP⁺ hESC-like colonies (FIG. 4a). Importantly, the combined effect of both the inhibitors (FIGS. 4b & 4c), as well as the individual effect of SB431542 was dose dependent.

Figures 2D, 2E, 2F:
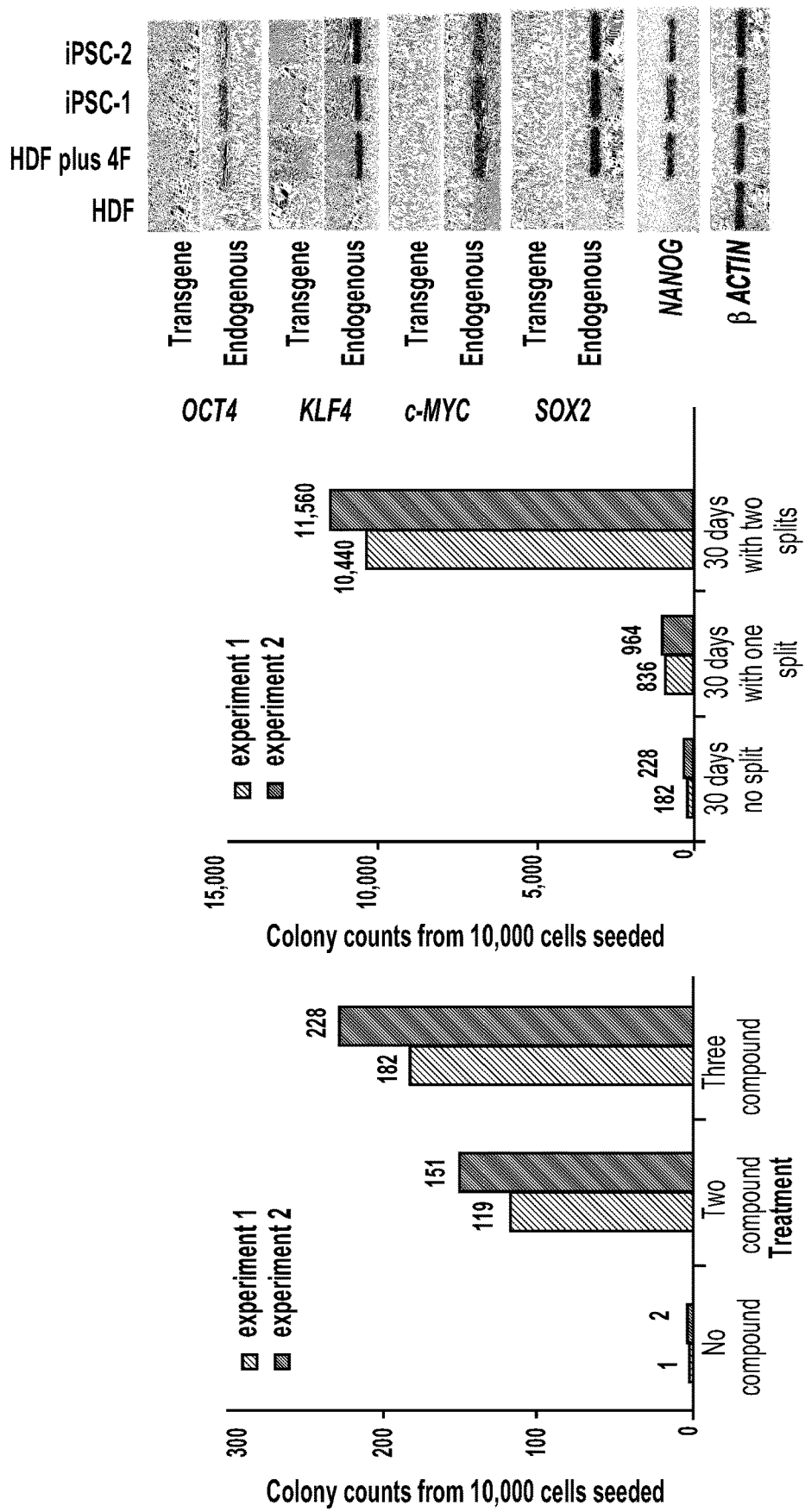

When we maintained the SB431542 plus PD0325901 treated cultures for 30 days without splitting, we obtained about 135 iPSC colonies per well (FIG. 2d), a >100 fold improvement in efficiency over the conventional method. Consistent with previous reports (Takahashi, K. et al., Cell 131, 861-72 (2007)), in untreated controls carrying 4TFs, we observed 1-2 iPSC colonies in addition to several granulate colonies (FIG. 2c). These granulate structures have been suggested to be partially reprogrammed colonies (Takahashi, K. et al., Cell 131, 861-72 (2007)). We also observed granulate colonies in the SB431542 treated cultures, which outnumbered by several fold the few hESC-like colonies. Interestingly, the number of granulate colonies was dramatically reduced in the combined SB431542 and PD0325901 treatment, which resulted in a concomitant increase in the number of hESC-like colonies. This suggested that a combined inhibition of ALK5 and MEK may guide partially reprogrammed colonies to a fully reprogrammed state and thereby improve the overall reprogramming process. Moreover, the fact that we observed improved induction of iPSCs as early as 7 days post-treatment suggests that treatment with these small molecules not only improved the efficiency of the reprogramming process but may also have accelerated its kinetics (FIG. 1a). Additional experiments are required to determine whether the reprogrammed cells at this stage indeed become fully independent of exogenous reprogramming factors earlier than in untreated cultures.

Figure 7:
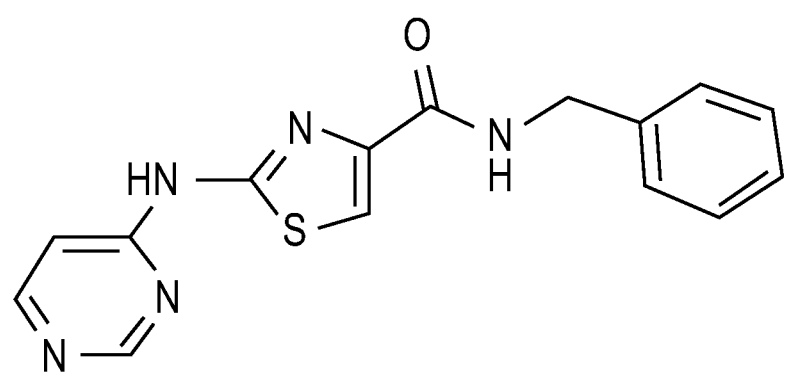
FIG. 7. Chemical structure of Thiazovivin.

Although iPSC colonies were picked and expanded, as in hESC cultures, the cultures split by trypsinization resulted in poor survival. From a recent screen performed in our laboratory we identified a novel small molecule, Thiazovivin (FIG. 7), which dramatically improved the survival of hESCs upon trypsinization. Addition of Thiazovivin to our cocktail of SB431542 and PD0325901 also vastly improved the survival of iPSCs after splitting by trypsinization (FIG. 2a), and a large number of reprogrammed colonies were obtained. From 10,000 cells that were originally seeded, a single 1:4 splitting on day 14 resulted in 1,000 hESC-like colonies on day 30 (FIG. 2e), while two rounds of splitting (on day 14 and on day 21 (1:10)) resulted in 11,000 hESC-like colonies (FIGS. 2c & 2e) on day 30. These colonies showed high levels of endogenous mRNA (FIG. 2f and protein expression (FIGS. 2b & 2c) of pluripotency markers, while the expression of the four transgenes could hardly be detected (FIG. 2f. In contrast, no iPSC colonies were obtained from untreated or 2 compound-treated samples that were trypsinized (Table 1).

TABLE 1

A comparison of the number of iPSC colonies observed in untreated, 2 compound treated and 3 compound treated cultures on day 30.

|  | No compound | 2 compounds | 3 compounds |
| --- | --- | --- | --- |
| No splitting | 1 | 135 | 205 |
| 1 splitting (on day 14) | 0 | 0 | 900 |
| 2 splitting (on day 14 & day 21) | N/A | N/A | 11,000 |

To examine whether the positive effect of Thiazovivin is solely due to survival of colonies after splitting or whether it also augments the reprogramming effect of combined SB431542 and PD0325901 treatment, we tested the 3 compound cocktail on 4TF-transduced cells that were not subjected to splitting. In these cultures, by day 14 we observed ~25 large colonies that were all expressing Nanog (FIG. 1e). By day 30 we observed ~205 very large NANOG⁺ colonies (FIG. 2d), that were also TRA-1-81⁺ and SSEA4⁺ (data not shown), which translated to a more than 200 fold improvement in efficiency over no compound treatment, and a two-fold increase over 2 compound treatment.

Figure 6A:
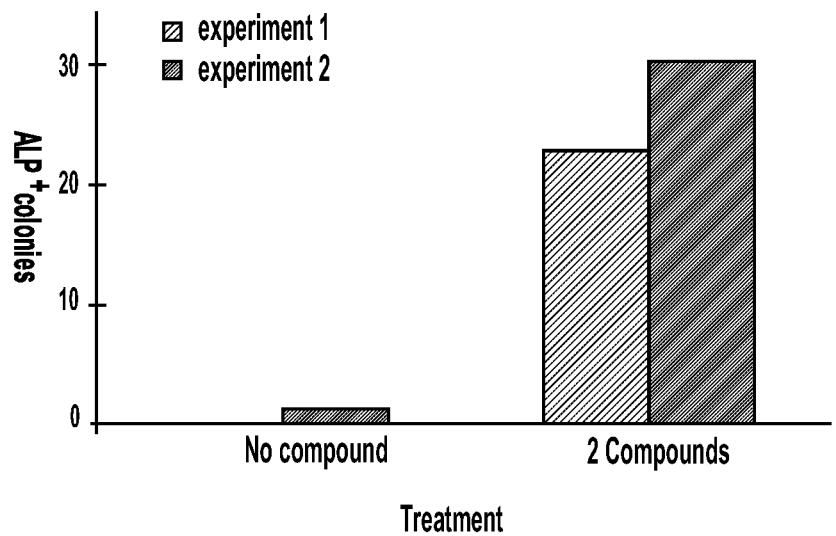
FIG. 6A-6F. Transgene expression and silencing are independent of compound treatment.
Figure 6B:
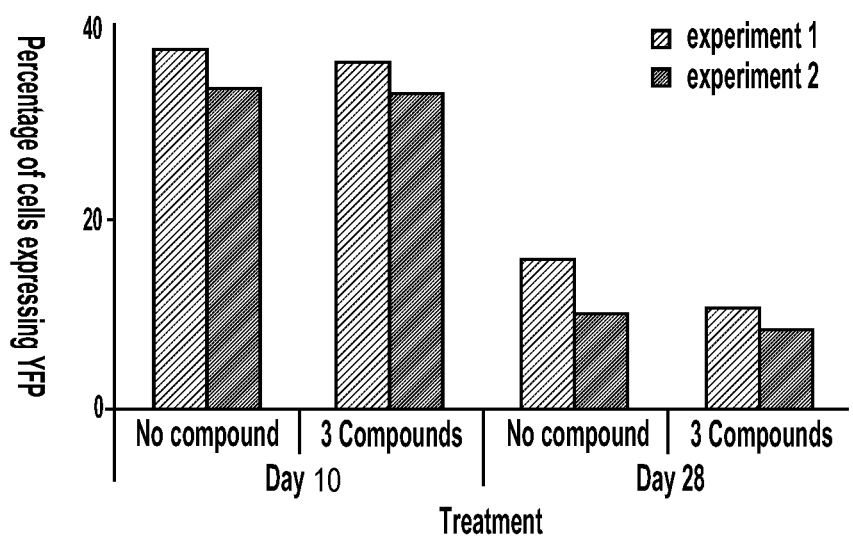
Figure 6C:
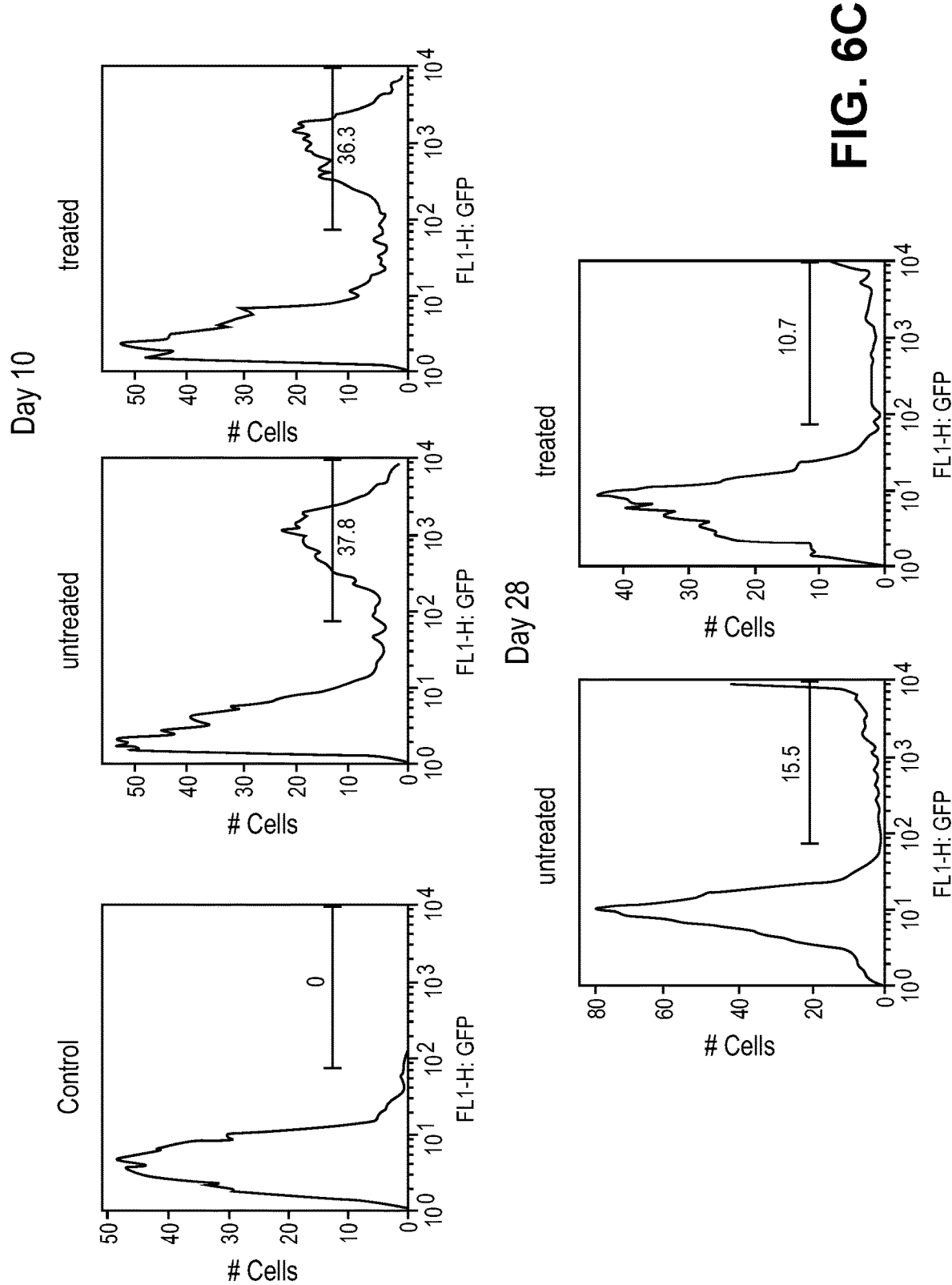
Figures 6D, 6E, 6F:
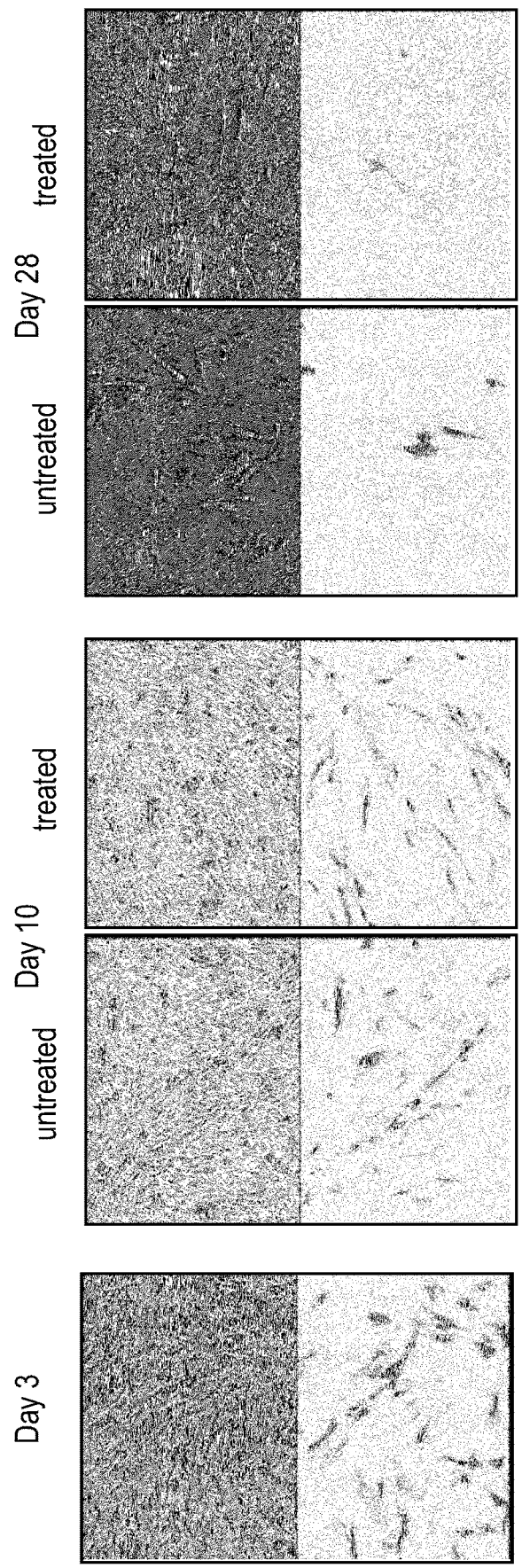

Two compound treatment also resulted in a larger number of alkaline phosphatase-positive colonies compared to untreated controls when the reprogramming factors were introduced using a lentiviral, rather than a retroviral system (FIG. 6a). Furthermore, the 3 compound cocktail did not appear to influence reprogramming factor expression from retroviral vectors (FIG. 6b-f).

Figure 5:
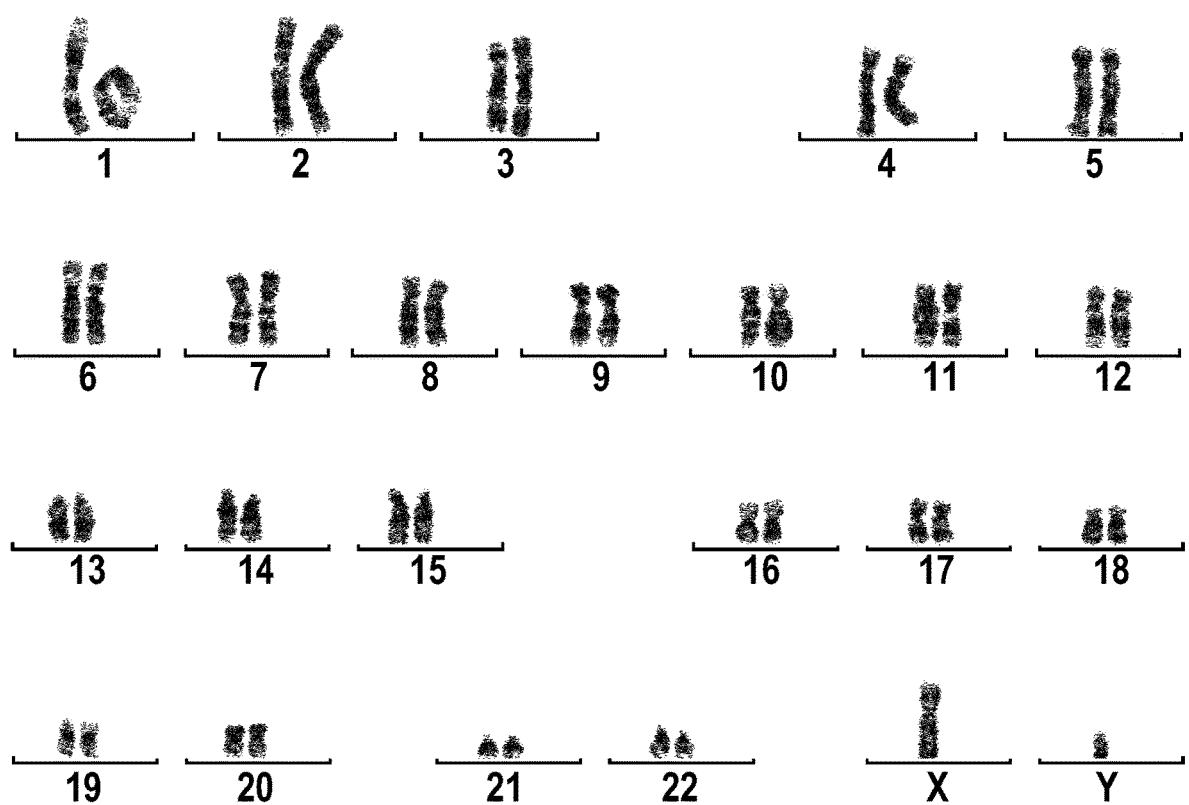
FIG. 5. Stably expanded iPS cell colonies generated through compound treatment exhibited normal karyotype.

The iPSC colonies generated using the 3 compound cocktail were readily and stably expanded for long term under conventional hESC culture conditions (over 20 passages) and they closely resembled hESCs in terms of morphology, typical pluripotency marker expression and differentiation potentials. They exhibited a normal karyotype (FIG. 5) and could be differentiated into derivatives of all three germ layers, both in vitro (FIGS. 3a & 3b) and in vivo (FIG. 3c). These results also suggested that there is no short term adverse effect associated with the much more convenient trypsinization procedure.

The demonstration that TGFβ and MEK-ERK pathway inhibition improved fibroblast reprogramming suggested critical roles for these two signaling pathways and MET mechanisms in the process. Consistently, addition of TGFβ had an inhibitory effect on 4 factor-mediated reprogramming of fibroblasts (data not shown). TGFβ and its family members play important contextual roles in self-renewal and differentiation of ESCs (Watabe, T. and Miyazono, K., Cell Res. 19, 103-15 (2009)). Moreover, TGFβ is a prototypical cytokine for induction of epithelial mesenchymal transition (EMT) and maintenance of the mesenchymal state (Willis, B. C. and Borok, Z., Am. J. Physiol. Lung Cell Mol. Physiol. 293, L525-34 (2007)). A major end point of this signaling, in this context, is down regulation of E-cadherin (Thiery, J. P. and Sleeman, J. P., Nat. Rev. Mol. Cell Biol., 7, 131-42 (2006)). E-cadherin has been shown to be important for the maintenance of pluripotency of ESCs and has been recently suggested to be a regulator of NANOG expression (Chou, Y. F. et al., Cell 135, 449-61 (2008)). Therefore inhibition of TGFβ signaling, which results in de-repression of epithelial fate, could benefit the reprogramming process in multiple ways. ERK signaling also promotes EMT (Thiery, J. P. and Sleeman, J. P., Nat. Rev. Mol. Cell Biol. 7, 131-42 (2006)), and is downstream of TGFβ in the process (Chou, Y. F. et al., Cell 135, 449-61 (2008)). We had previously shown that the effect of reversine, a small molecule which can reprogram myoblasts to a multipotent state, is mediated in part through inhibition of MEK-ERK (Chen, S. et al., *Proc. Natl. Acad. Sci. USA* 104, 10482-87 (2007)). This may explain the effect observed in reprogramming when it was combined with TGFβ inhibition.

The chemical platform described here is unique, in that it modulates upstream signaling pathways and could radically improve reprogramming on a general cell type, like fibroblasts. The chemical conditions described here provide a basic platform for non-viral and non-DNA based (Zhou, H. et al., *Cell Stem Cell* 4, 381-84, (2009)), more efficient and safer reprogramming methods, which could yield an unlimited supply of safe human iPSCs for various applications.

Methods

Cell Culture

Primary skin fibroblasts CRL2097 and BJ (neonatal foreskin) were purchased from ATCC. All cell culture media reagents were purchased from Invitrogen Corporation, Calif. The cells were maintained in DMEM (10313-021) containing 10% FBS (10439-024), 1×MEM Non-Essential Amino acid (11140-050), 1× Glutamax (35050-061), 10 mM Hepes (15630-080) and 0.11 mM 2-Mercaptoethanol (21985-023). Cells were passaged 1:5 using 0.05% (1×) trypsin-EDTA (25300-054).

Plasmids

The pMXs vector encoding the human cDNAs for OCT4, SOX2, c-MYC and KLF4, described before (Takahashi, K. et al., *Cell* 131, 861-72 (2007)), were obtained from ADDGENE. Mouse Slc7a1 ORF was cloned into pWPXLD (Addgene), as described previously (Takahashi, K. et al., *Cell* 131, 861-72 (2007)).

Retroviral Infection and iPS Cell Generation

Lentiviruses carrying OCT4, NANOG, SOX2 & LIN28 were produced as described before (Yu, J. et al., *Science* 318, 1917-20 (2007)). For retrovirus production, PLAT-E packaging cells were plated at 1×10$^6$ cells/well of a 6-well plate. After 24 hours, the cells were transfected with pMXs vectors carrying OCT4, SOX2, c-MYC and KLF4 cDNAs using Fugene 6 transfection reagent (Roche) according to manufacturer's instructions. Twenty-four hours after transfection, the medium was replaced with fresh medium and the plate was transferred to 32° C. for retrovirus production. The viruses were collected at 48 hours and 72 hours, and filtered with 0.45 µm filter before transduction.

The Slc7a1-expressing human fibroblast cells were seeded at 1×10$^5$ cells/well of a 6 well plate on the day 1. On day 2, 0.25 ml of each retroviral supernatant was added to the cells in the presence of 6 µg/ml polybrene. A second round of transduction was done on day 3. Infection efficiency was estimated by fluorescence microscopy on cells transduced in parallel with GFP or RFP gene-carrying retroviruses. Seven days after initial transduction, fibroblasts were harvested by trypsinization and re-plated at 1×10$^4$ cells/well of a 6 well plate coated with matrigel (1:50 dilution, cat 354234, BD Biosciences). For compound treatment, the cells were cultured in human reprogramming medium (DMEM/F12, 20% Knockout serum replacer, 1x MEM Non-Essential amino acid, 1x glutamax, 0.11 mM 2-Mercaptoethanol, 20 ng/ml bFGF and 1,000 U/ml LIF) and were treated with 2 µM SB431542 (Stemgent), 0.5 µM PD0325901 (Stemgent), 0.5 µM Thiazovivin, or combinations of the compounds. The media were changed every 2-3 days depending on the cell density. Seven days after compound treatment, either the plates were fixed and stained for Alkaline phosphatase (ALP) activity, or stained for protein markers, or the cultures were continued with or without indicated splitting by trypsinization till day 30. For split cultures, the cells were split (1:4) and re-plated onto irradiated CF-1 MEF feeder layer (2.5×105 cells/well) in each well of 6 well plate and were split (1:10) again on day 21. The cells were maintained in the same media and compound cocktail described above except for the concentrations of PD0325901 (0.5 µM for D14 and 1 µM for D21) and SB431542 (0.5-1 µM after D14). The iPSC colonies were subsequently maintained in conventional hESC media in the absence of the above compounds.

Alkaline Phosphatase Staining and Immunocytochemistry

Alkaline phosphatase staining was performed using ALP detection kit (cat no: SCR004, Chemicon) according to the product instructions. For immunocytochemistry, cells were fixed in 4% paraformaldehyde (10 min, RT), washed twice with PBS, blocked using 5% normal donkey serum (Chemicon) and 0.1% TritonX-100 (15 min, RT) and then treated with primary antibodies overnight at 4° C. The primary antibodies used were anti-NANOG (cat no: AB9220, Chemicon, 1:1,000); anti-OCT4 (cat no: sc-5279, Santa Cruz biotech, 1:200), anti-SSEA 4 (cat no: mab4304, Chemicon, 1:500), anti-Tra-1-81 (cat 560123, BD Biosciences, 1:100), anti-Tra-1-81 (mAb 4381, Chemicon, 1:500), anti-βIII TUBULIN (cat no: MMS-435P, Covance Research Products Inc, 1:1000), anti-PDX 1 (1:500) (a kind gift from Dr. C. Wright), anti-BRACHYURY (cat No: AF2085, R & D, final concentration 0.2 µg/ml). The cells were washed twice with PBS and then treated with secondary antibodies for 1 hour at room temperature. The secondary antibodies used were Alexa fluor 488 donkey anti-rabbit or anti-mouse IgG (Invitrogen, 1:1,000) and Alexa fluor 555 donkey anti-rabbit or anti-mouse IgG (Invitrogen, 1:1,000). Nuclei were stained with 0.5 µg/ml DAPI (Sigma). Images were captured using a Nikon Eclipse TE2000-U/X-cite 120 EXFO microscope with a photometric CoolSnap HQ2 camera.

In Vitro Differentiation and Teratoma Assay

Generation of embryoid bodies and in vitro differentiation were performed as described elsewhere (Takahashi, K. et al., *Cell* 131, 861-72 (2007)). For the teratoma assay, 3-5 million cells were injected under the kidney capsule of SCID mice. Thirty one days later the tumors were excised and fixed in 4% paraformaldehyde and histologically analyzed at the TSRI histology core facility. The use of SCID mice was approved by the UCSD animal research committee.

RT-PCR

Total RNA was extracted from cells using RNeasy minikit (Qiagen). cDNAs were synthesized according to product instructions using superscript III first strand synthesis kit (Invitrogen). Two microliters of the reaction product was used for 24-28 PCR cycles using respective primers. The sequences of the primers are described elsewhere (Takahashi, K. et al., *Cell* 131, 861-72 (2007)).

Flow Cytometry

For flow cytometry analysis, the cultures were mildly trypsinized and harvested from 6 well plates. The cells were washed and resuspended in FACS buffer (PBS, 2 mM EDTA, 2 mM HEPES, 1% FBS), and were analyzed on a FACS Calibur cytometer (Becton Dickinson, San Jose, Calif.) with the CellQuest program.

Example 2: Synthesis of N—(cyclopropylmethyl)-4-(4-(6-hydroxy-3,4-dihydroquinolin-1(2H)-yl)pyrimidin-2-ylamino)benzenesulfonamide (Thiazovivin)

The reaction flask containing 2,4-dichloropyrimidine (372 mg, 2.5 mmol), 6-methoxy-1,2,3,4-tetrahydroquinoline (489 mg, 3 mmol) and diisopropylethylamine (0.52 mL, 3 mmol) in n-butanol (10 mL) was heated at 40° C. overnight. The solvent was evaporated, and the residue was purified by flash column chromatography to give 2-Chloro-4-(6-methoxy-3,4-dihydroquinolin-1(2H)-yl)pyrimidine (551 mg, 80%). This intermediate (250 mg, 0.91 mmol) was then dissolved in dichloromethane and treated with BBr$_3$ (1 M in dichloromethane) (1 mL, 1 mmol) at −78° C. The reaction mixture was slowly warmed up to room temperature and stirred for 1 hr, poured into water, extracted with dichloromethane. The combined organics were dried over anhydrous Na$_2$SO$_4$ and concentrated. The residue was purified by flash column chromatography to give 2-Chloro-4-(6-hydroxy-3,4-dihydroquinolin-1(2H)-yl)pyrimidine (154 mg, 65%). To a stirred solution of 2-chloro-4-(6-hydroxy-3,4-dihydroquinolin-1(2H)-yl)pyrimidine (29 mg, 0.11 mmol) and 4-amino-N—(cyclopropylmethyl)benzenesulfonamide (27 mg, 0.12 mmol) in DMF (0.5 mL) was added p-toluenesulfonic acid (2 M in dioxane) (55 µL, 0.11 mmol). The reaction mixture was stirred at 90° C. overnight, then purified by HPLC to give the title compound (27 mg, 56%).

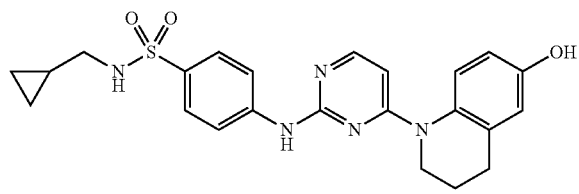 [SMILES: O=S(=O)(NCC1CC1)c1ccc(Nc2nccc(N3CCCc4cc(O)ccc43)n2)cc1]

Example 3: Reprogramming of Human Primary Somatic Cells by OCT4 and Chemical Compounds Here we report a novel small molecule cocktail that enables reprogramming of human primary somatic cells to iPSCs with exogenous expression of only OCT4.

Figure 8A:
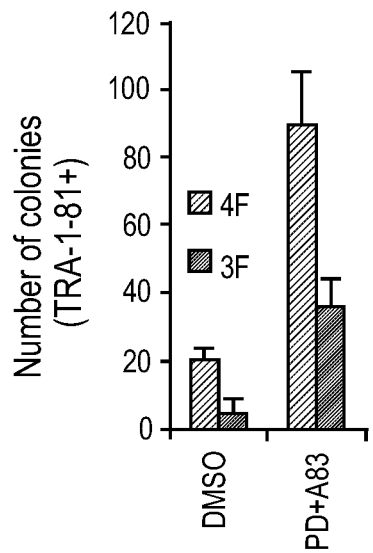
FIG. 8A-8E. Generation of human induced pluripotent stem cells from primary keratinocytes by single gene, OCT4, and small molecules.
Figure 8B:
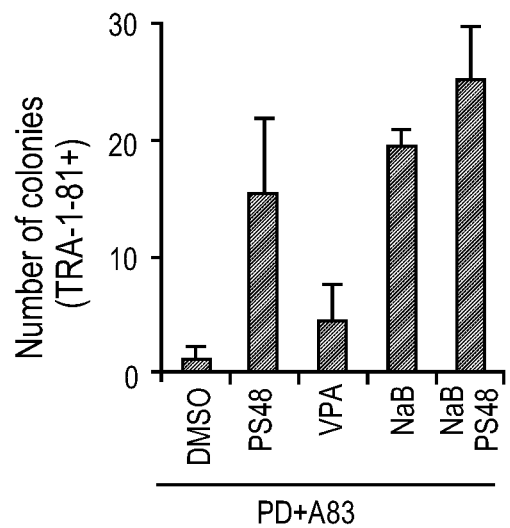
Figure 8C:
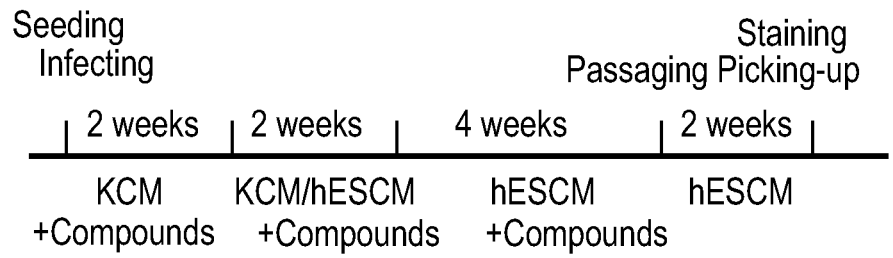
Figure 8D:
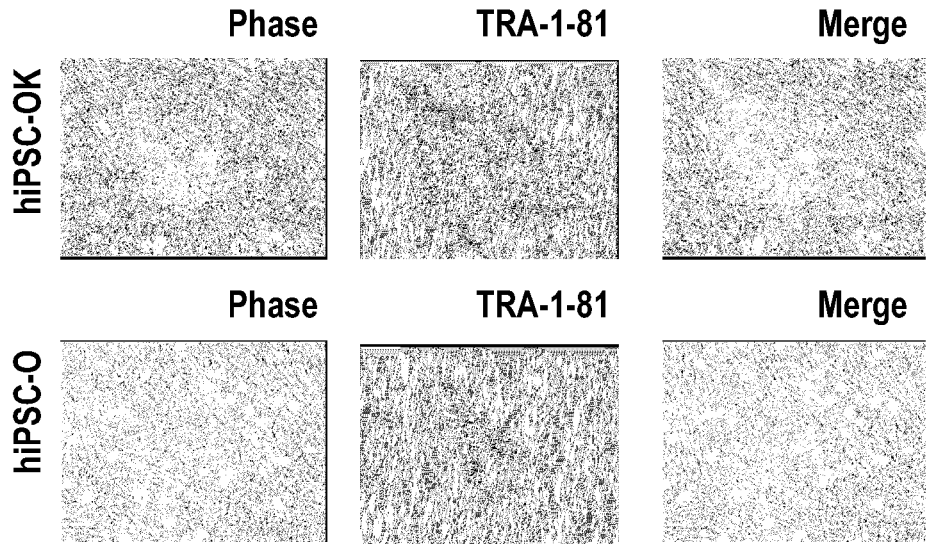
Figure 8E:
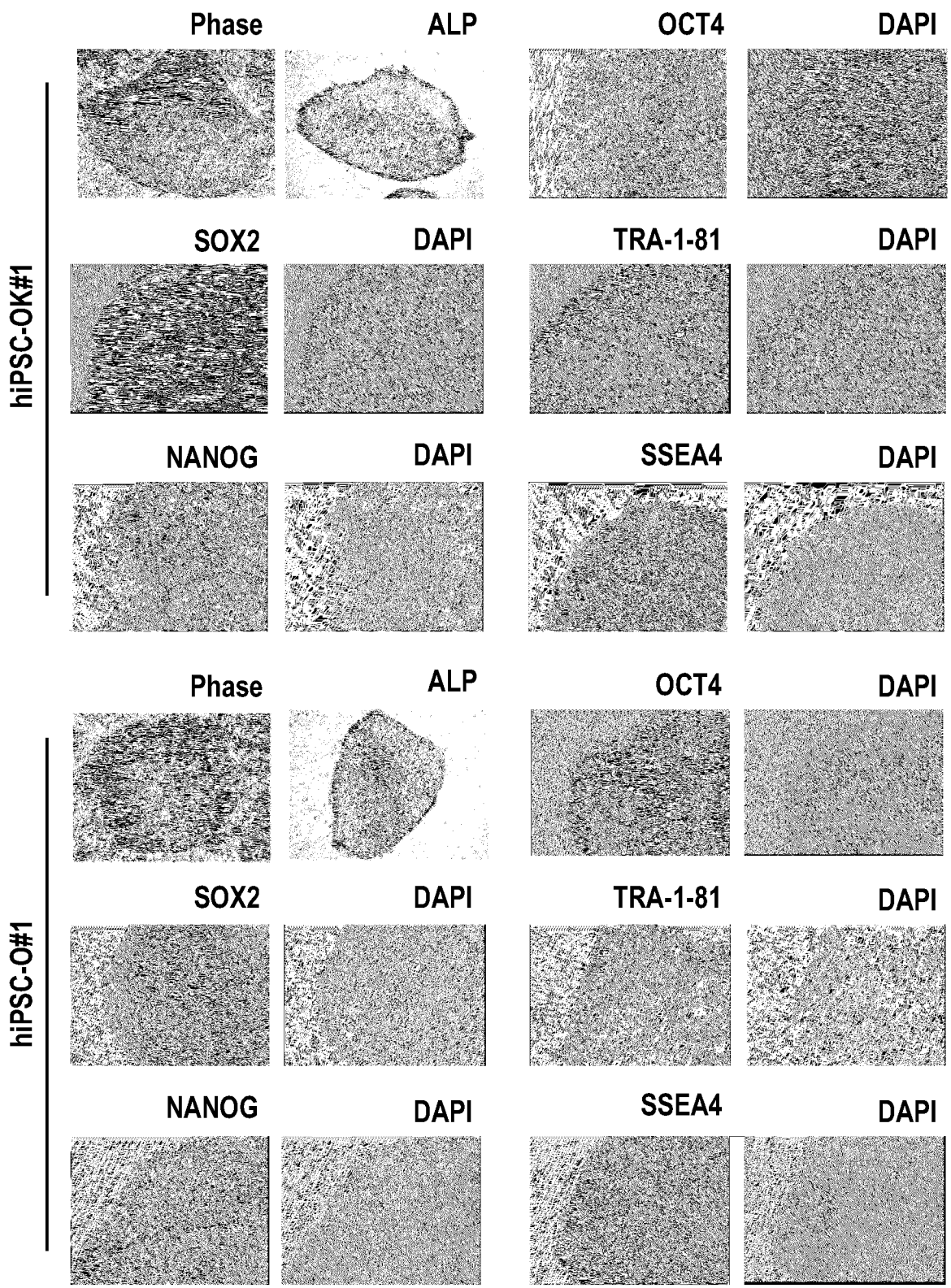

Among several readily available primary human somatic cell types, keratinocytes that can be easily isolated from human skin or hair follicle represent an attractive cell source for reprogramming, because they endogenously express KLF4 and cMYC, and were reported to be reprogrammed more efficiently using the conventional four TFs or three TFs (without MYC) (Aasen, T. et al., Nat Biotechnol 26:1276-1284 (2008); Maherali, N. et al., Cell Stem Cell 3, 340-345 (2008)). More recently, we reported that dual inhibition of TGFβ and MAPK/ERK pathways using small molecules (i.e. SB431542 and PD0325901, respectively) provides a drastically enhanced condition for reprogramming of human fibroblasts with four exogenous TFs (i.e. OSKM) (Lin, T. et al., Nat Methods 6:805-808 (2009)). Furthermore, we have shown that such dual pathway inhibition could also enhance reprogramming of human keratinocytes by two exogenous TFs (i.e. OK) with two small molecules, Parnate (an inhibitor of lysine-specific demethylase 1) and CHIR99021 (a GSK3 inhibitor) (Li, W. et al., Stem Cells 27:2992-3000 (2009)). However, such 2-TFs reprogramming process was very inefficient and complex (e.g. involving two exogenous TFs and four chemicals), and reprogramming with even one less TF appeared daunting. Toward the OCT4 only reprogramming, we developed a step-wise strategy in refining reprogramming condition and identifying new reprogramming chemical entities. We first attempted to further optimize the reprogramming process under the four or three TFs (i.e. OSKM or OSK) condition in neonatal human epidermal keratinocytes (NHEKs) by testing various inhibitors of TGFβ and MAPK pathways at different concentrations using previously reported human iPSC characterization methods (Lin, T. et al., Nat Methods 6:805-808 (2009)). Encouragingly, we found that the combination of 0.5 µM PD0325901 and 0.5 µM A-83-01 (a more potent and selective TGFβ receptor inhibitor) was more effective in enhancing reprogramming of human keratinocytes transduced with OSKM or OSK (FIG. 8a). Remarkably, when we further reduced viral transductions to only two factors/OK, we could still generate iPSCs from NHEKs when they were treated with 0.5 µM PD0325901 and 0.5 µM A-83-01, although with low efficiency. Then we began screening additional small molecules from a collection of known bioactive compounds at various concentrations as previously reported. Among dozens of compounds tested so far, surprisingly we found that a small molecule activator of PDK1 (3'-phosphoinositide-dependent kinase-1), PS48 (5 µM) that has never been reported in reprogramming, can significantly enhance the reprogramming efficiency about fifteen fold. Interestingly, we also found that 0.25 mM sodium butyrate (NaB, a histone deacetylase inhibitor) turned out to be much more reliable and efficient than the previously reported 0.5 mM VPA for the generation of iPSCs under OK condition (FIG. 8b). Subsequent follow-up studies demonstrated that combination of 5 µM PS48 and 0.25 mM NaB could further enhance the reprogramming efficiency over twenty-five fold (FIG. 8b and Table 4). With such unprecedented efficiency in reprogramming NHEKs under only two TFs, we further explored the possibility of generating iPSCs with OCT4 alone by refining combinations of those small molecules during different treatment windows. Primary NHEKs were transduced with OCT4 and treated with chemicals (FIG. 8c). Among various conditions, small iPSC colonies resembling hESCs (four to six colonies out of 1,000,000 seeded cells) appeared in OCT4 infected NHEKs that were treated with 0.25 mM NaB, 5 µM PS48 and 0.5 µM A-83-01 during the first four weeks, followed by treatment with 0.25 mM NaB, 5 µM PS48, 0.5 µM A-83-01 and 0.5 µM PD0325901 for another four weeks (FIG. 8c). Such TRA-1-81 positive iPSC colonies (FIG. 8d) grew larger under conventional hESC culture media and could be serially passaged to yield stable iPSC clones that were further characterized (FIGS. 8e and 9). More significantly, OCT4 only iPSCs could also be generated from human adult keratinocytes by addition of 2 µM Parnate and 3 µM CHIR99021 (which had been shown to improve reprogramming of NHEKs under OK condition) to this chemical cocktail. After the reliable reprogramming of primary keratinocytes to iPSCs by OCT4 and small molecules, we further applied the conditions to other human primary cell types, including HUVECs (differentiated mesoderm cells) and AFDCs (amniotic fluid derived cells). Similarly, TRA-1-81 positive iPSC colonies appeared in OCT4 infected HUVECs and AFDCs that were treated with chemicals. Remarkably, it appeared that reprogramming of HUVECs and AFDCs was more efficient and faster than reprogramming of NHEKs under the OCT4 and small molecule conditions (Table 4). Two clones of iPSCs from each cell type were long-term expanded for over 20 passages under conventional hESC culture condition and further characterized (Table 5).

Figure 9B:
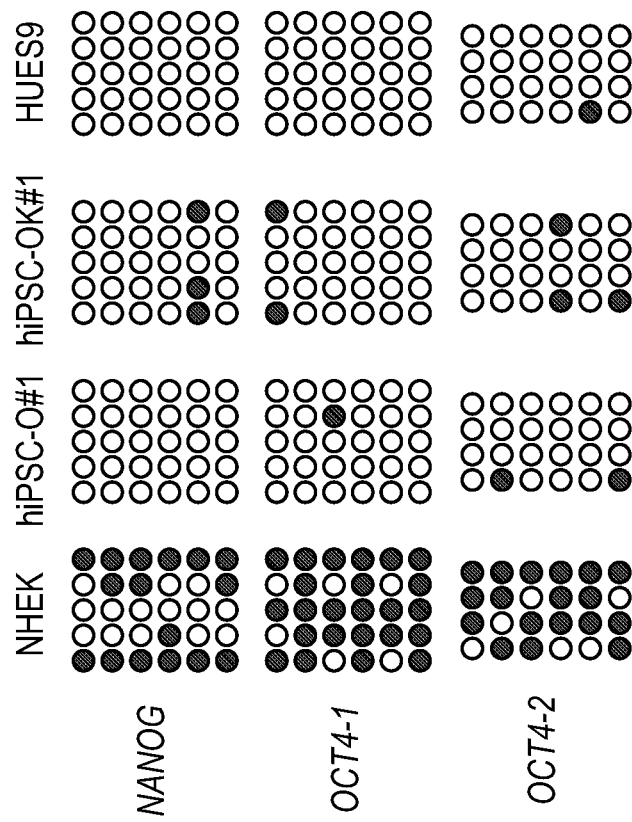
FIG. 9A-9F. In depth characterizations of human iPSC-OK and iPSC-O cells.
Figure 9A:
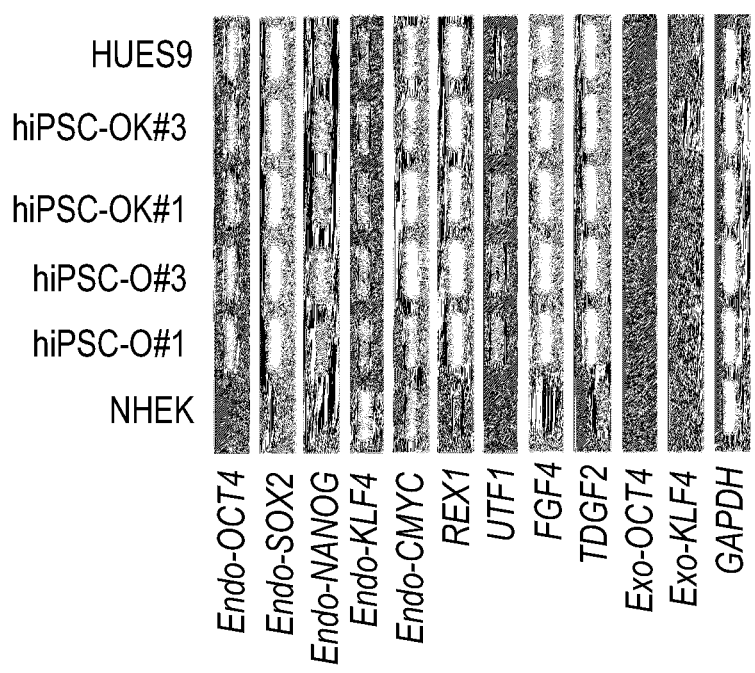
Figure 9D:
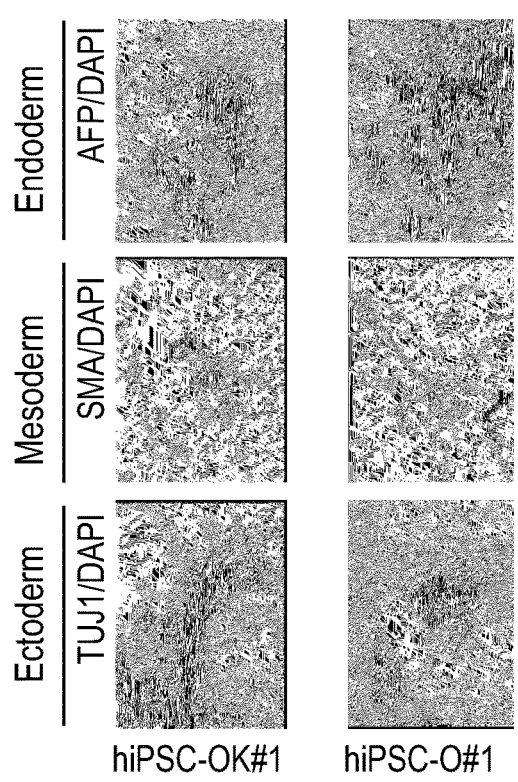
Figure 9C:
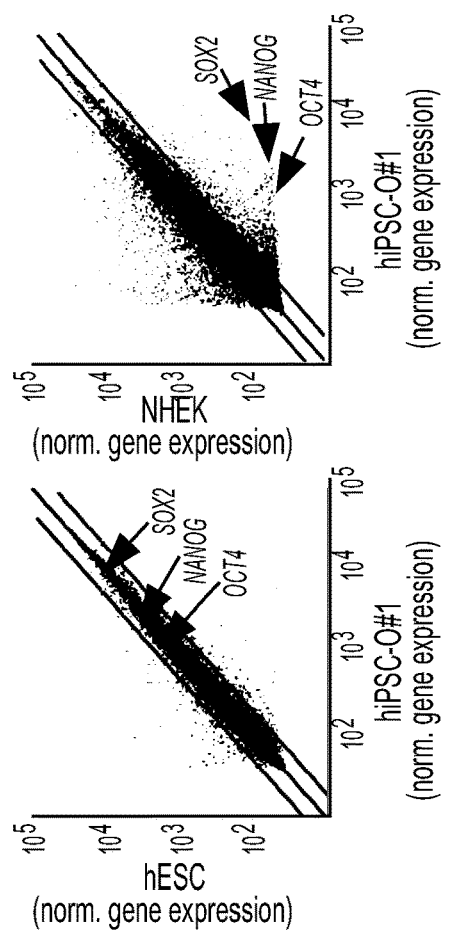
Figure 9F:
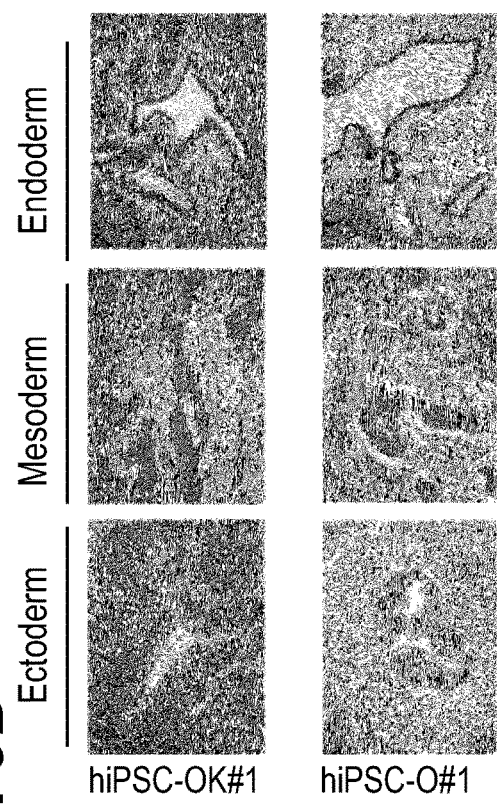
Figure 9E:
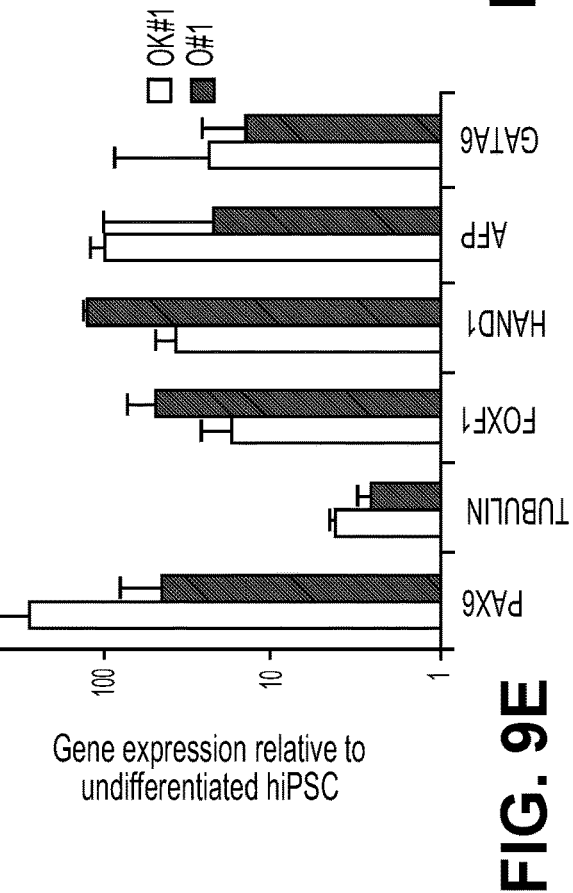
Figure 10E:
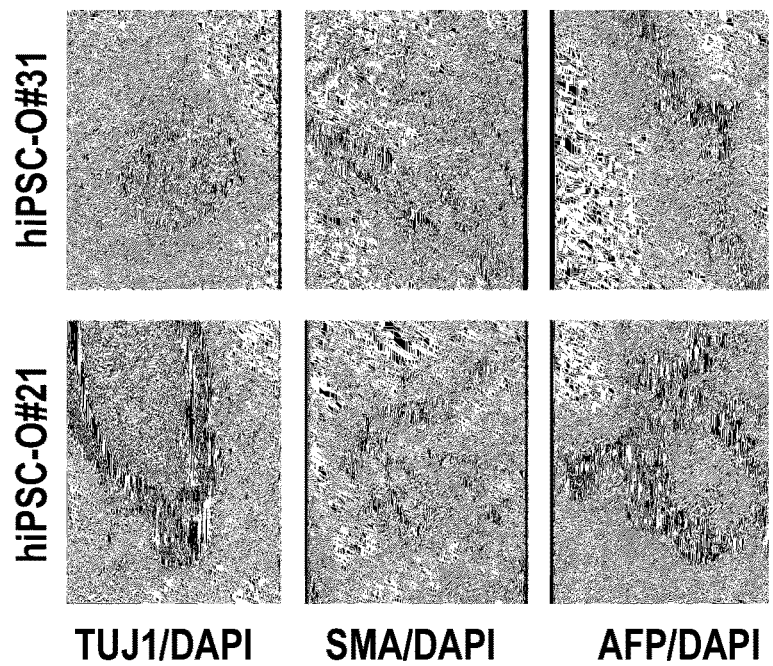
Figure 10D:
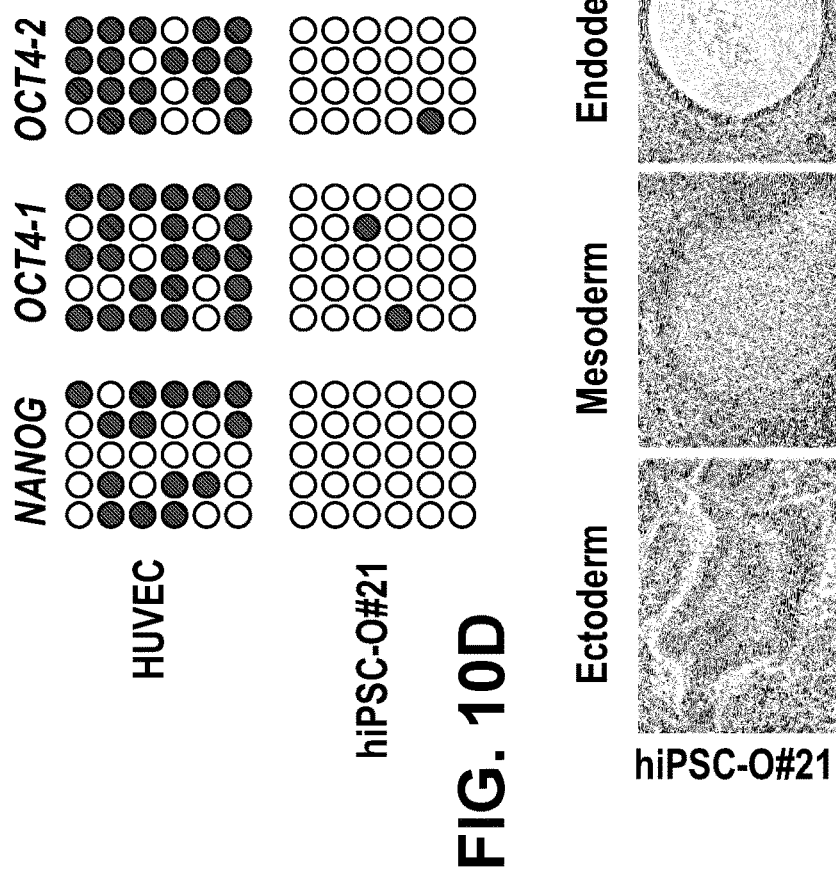
Figure 10F:
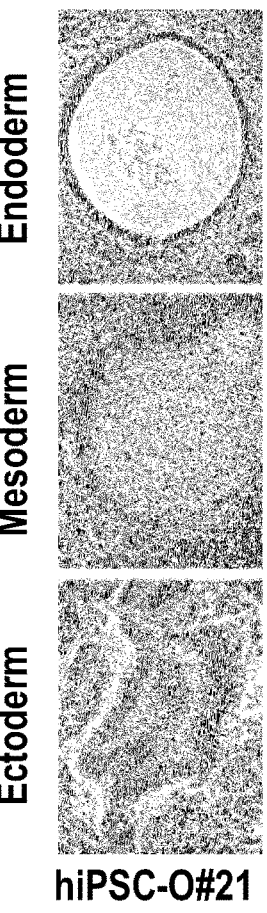
Figure 11A:
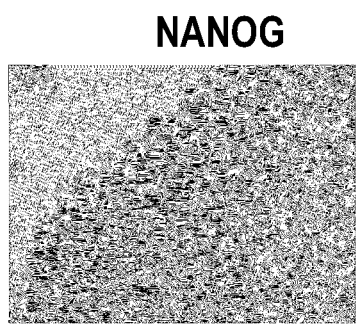
FIG. 11A-11B. Characterization of human iPSC-O cells from AHEKs.
Figure 11A:
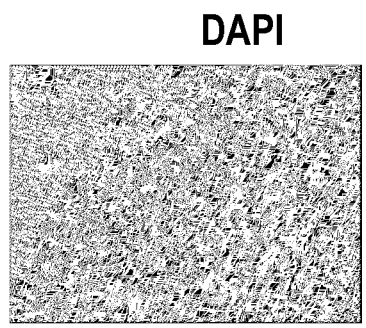
Figure 11A:
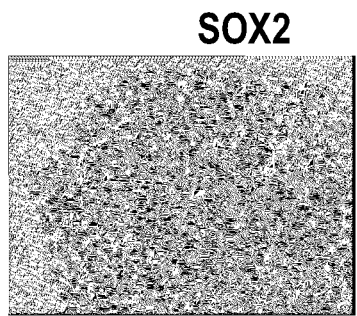
Figure 11A:
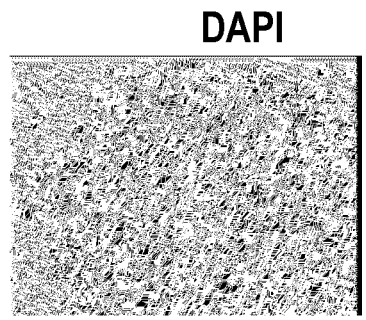
Figure 11A:
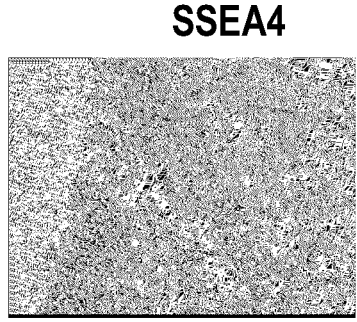
Figure 11A:
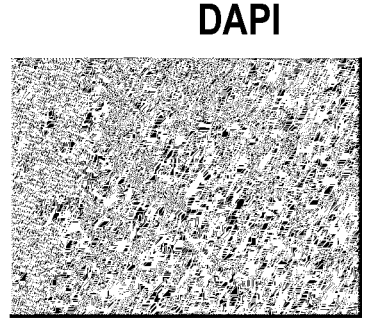
Figure 11B:
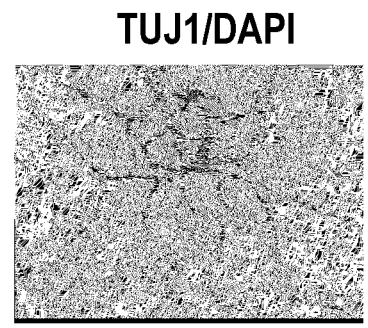
Figure 11B:
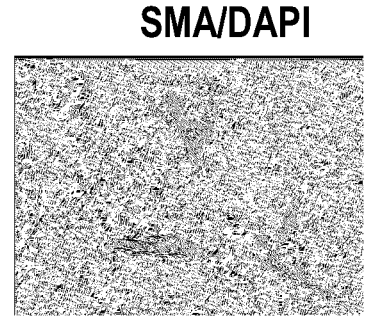
Figure 11B:
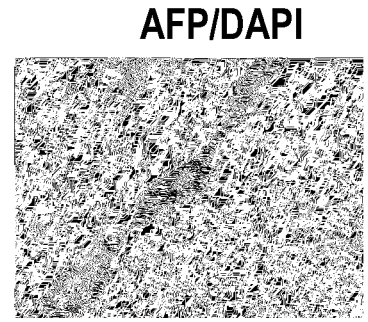
Figure 12A:
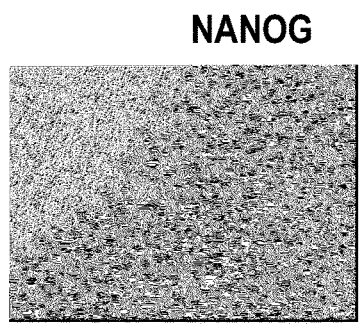
FIG. 12A-12B. Characterization of human iPSC-O cells from AFDCs.
Figure 12A:
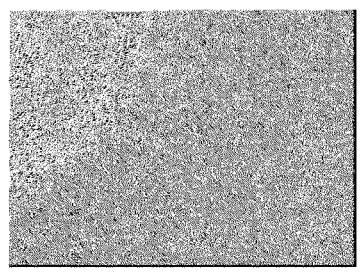
Figure 12A:
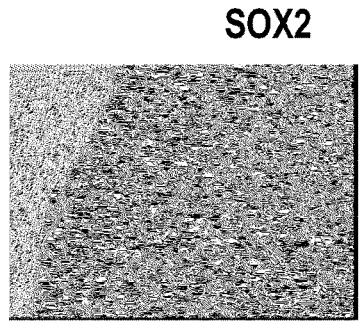
Figure 12A:
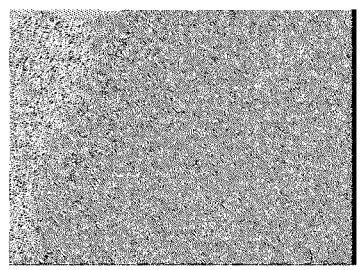
Figure 12A:
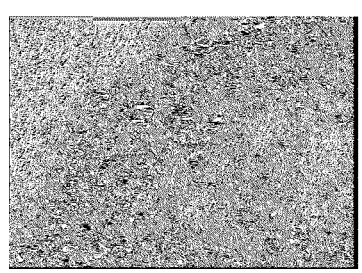
Figure 12A:
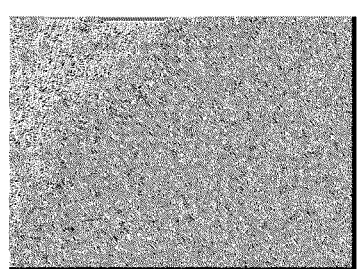
Figure 12B:
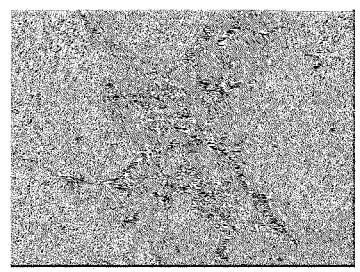
Figure 12B:
Figure 12B:
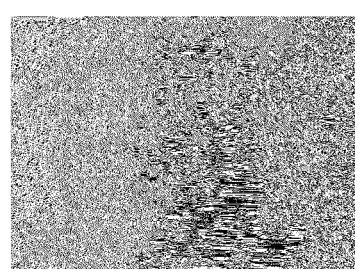
Figure 13:
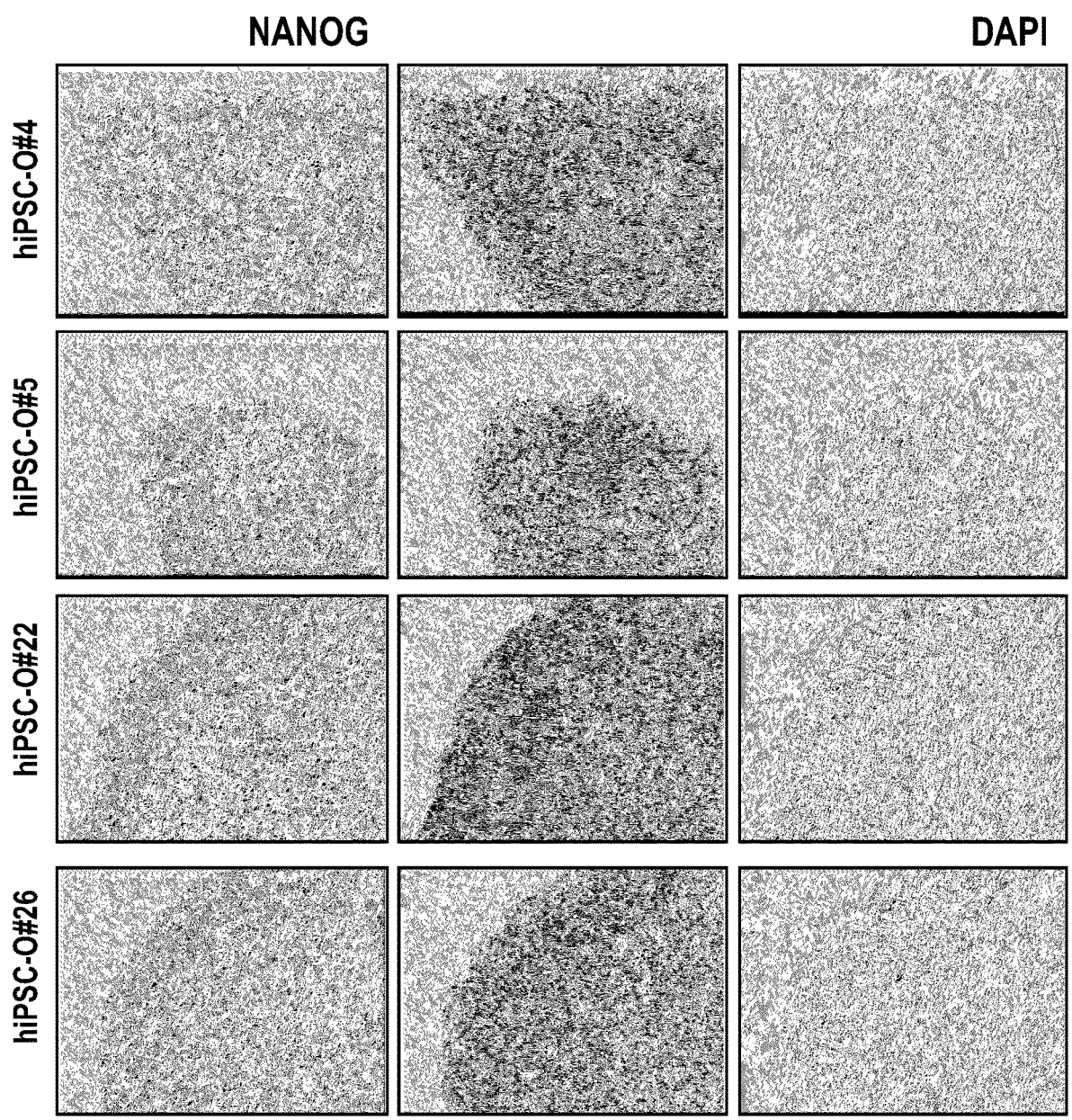
FIG. 13. Additional hiPSC cell lines express typical pluripotency markers. The other established hiPSC-O cell lines express typical pluripotency markers, including NANOG and SSEA-4. Nuclei were stained with DAPI.
Figure 14:
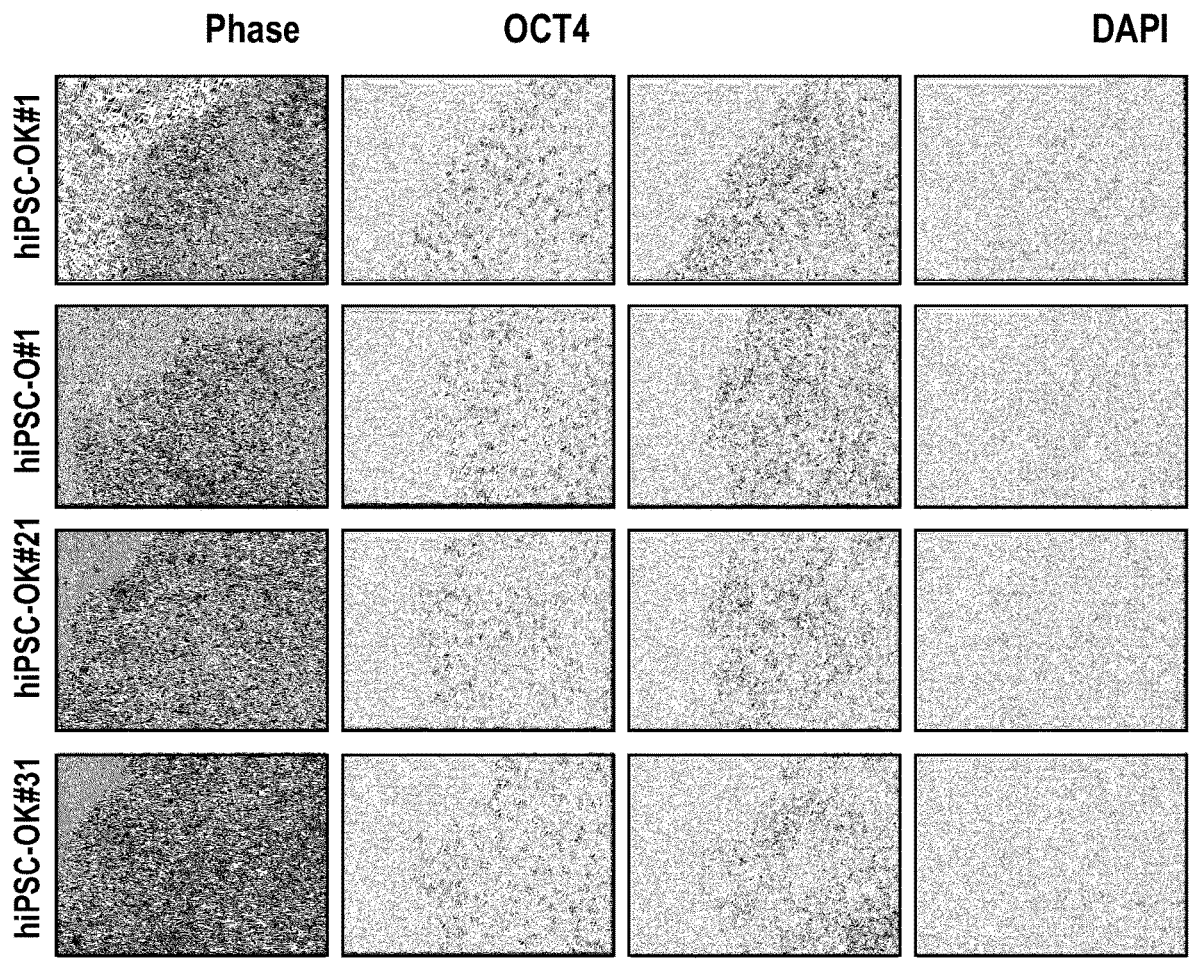
FIG. 14. Feeder free culture of hiPSC cell lines. hiPSCs were split onto Matrigel/ECM-coated plates in chemically defined hESC medium as previously reported. These hiPSCs could be maintained and expanded in a feeder-free environment. ICC showed the expression of pluripotency markers, OCT4 and SSEA4. Nuclei were stained with DAPI.
Figure 15A:
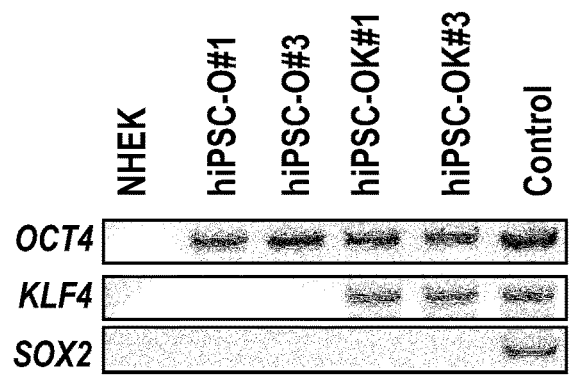
FIG. 15A-15B. Genotyping of hiPSCs. RT-PCR analysis using genomic DNA shows that only OCT4 transgene integrated in the genome of hiPSC-O lines (hiPSC-O#1, hiPSC-O#3, hiPSC-O#21, hiPSC-O#26 and hiPSC-O#31). NHEKs (FIG. 15A) and HUVECs (FIG. 15B) used as negative controls, while vectors used as positive controls.
Figure 15B:
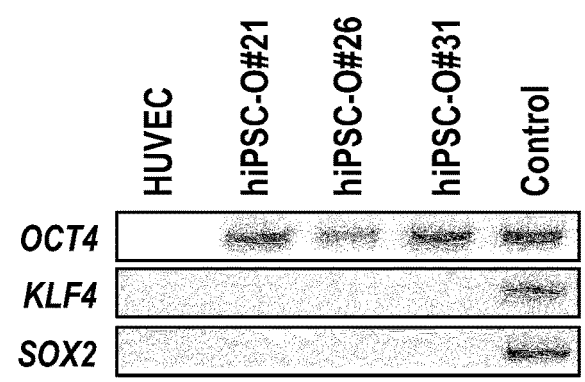
Figure 16:
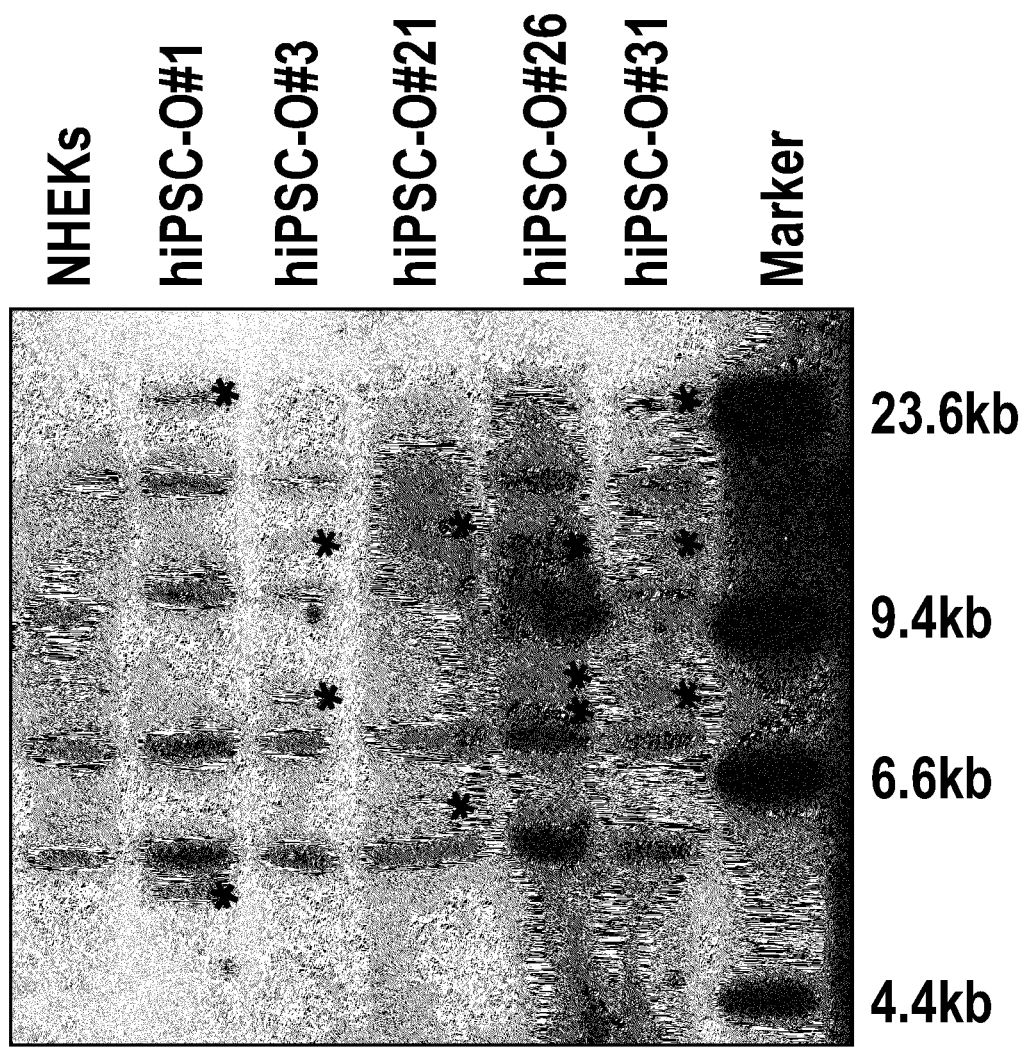
FIG. 16. Integration of the OCT4 transgene in hiPSCs. Genomic DNA (10 μg) were digested with EcoRI and hybridized with the OCT4 cDNA probe (an EcoRI/SpeI fragment of pSin-EF2-OCT4-Pur). Multiple transgenic integrations were detected.
Figure 17A:
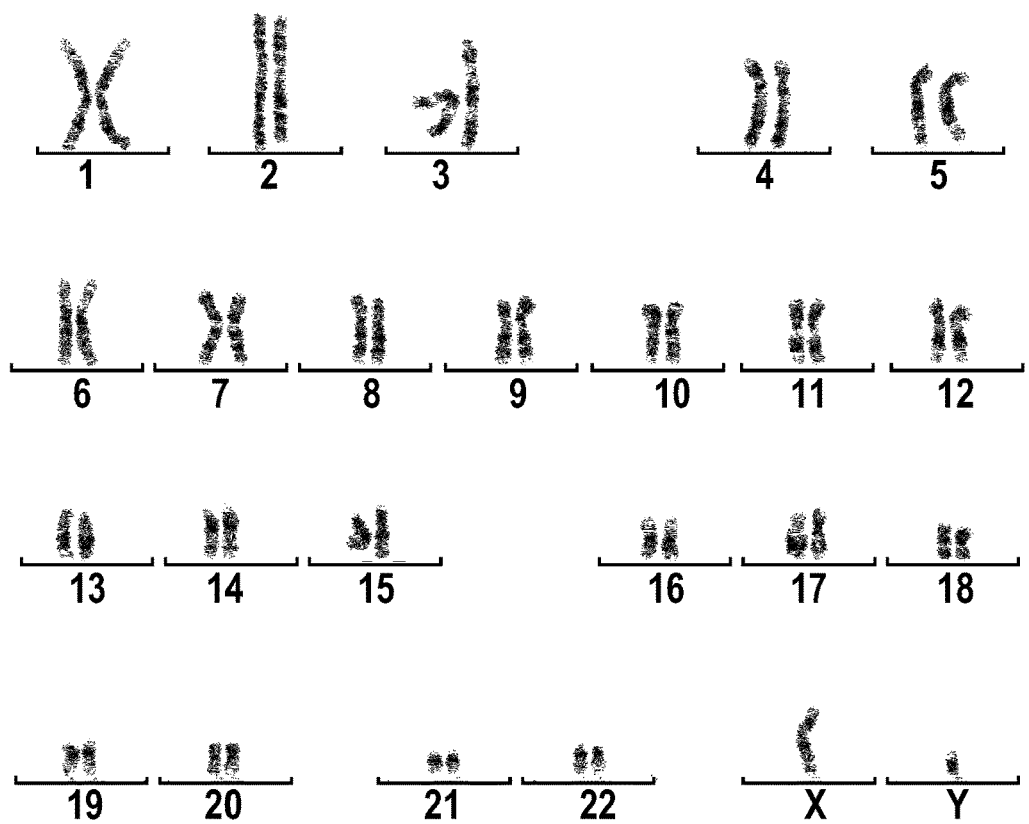
FIG. 17A-17B. Karyotyping for hiPSC cell lines. Metaphase spread of hiPSC-O#1 (FIG. 17A) and hiPSC-O#21 (FIG. 17B) show normal karyotype after passage 15.
Figure 17B:
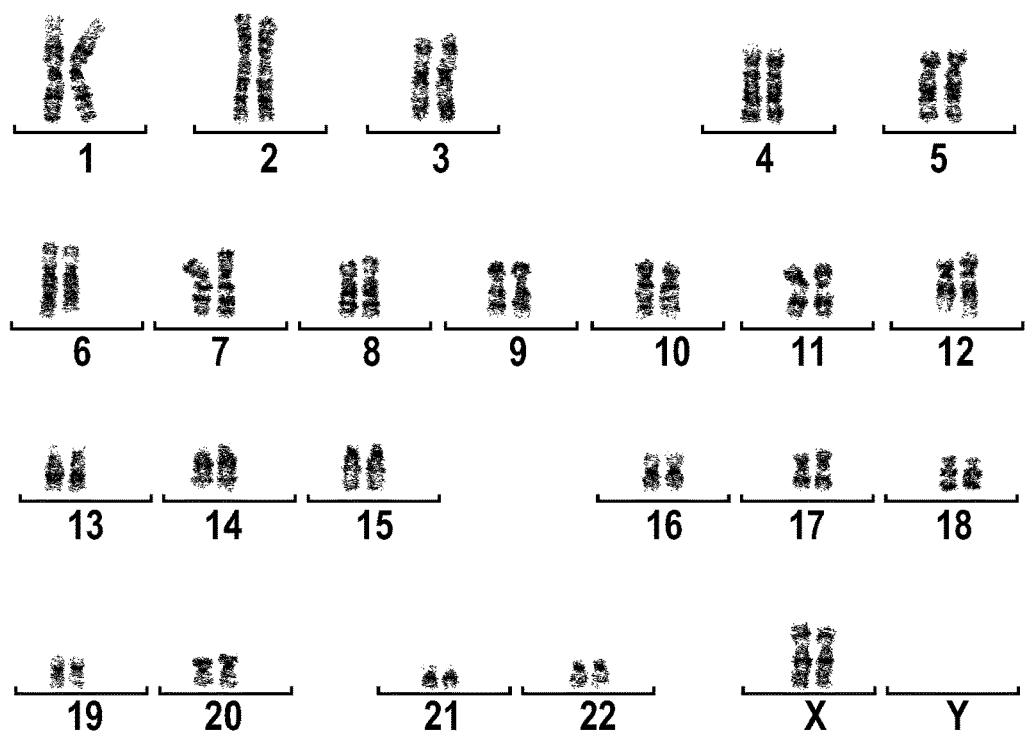

These stably expanded hiPSC-OK and hiPSC-O cells are morphologically indistinguishable to hESCs, and could be cultured on ECM-coated surface under feeder-free and chemically defined conditions (FIG. 8e and FIG. 13). They stained positive for alkaline phosphatase (ALP) and expressed typical pluripotency markers, including OCT4, SOX2, NANOG, TRA-1-81 and SSEA4, detected by immunocytochemistry/ICC (FIGS. 8e, 10b, 11-12). In addition, RT-PCR analysis confirmed the expression of the endogenous human OCT4, SOX2, NANOG, REX1, UTF1, TDGF2, FGF4 genes, and silencing of exogenous OCT4 and KLF4 (FIGS. 9a and 10c). Furthermore, bisulfite sequencing analysis revealed that the OCT4 and NANOG promoters of hiPSC-OK and hiPSC-O cells are largely demethylated (FIGS. 9b and 10d). This result provides further evidence for reactivation of the pluripotency transcription program in the hiPSC-OK and hiPSC-O cells. Global gene expression analysis of hiPSC-O cells, NHEKs and hESCs showed that hiPSC-O cells are distinct from NHEKs (Pearson correlation value: 0.87) and most similar to hESCs (Pearson correlation value: 0.98) (FIG. 9c). Genotyping analysis showed that hiPSC-O cells only contained the OCT4 transgene without the contamination of transgene KLF4 or SOX2 (FIG. 15). Southern blot analysis showed that there were multiple different integration sites of the OCT4 transgene (FIG. 16) among different clones. In addition, karyotyping result demonstrated that hiPSC-O maintained normal karyotype during the whole reprogramming and expansion process (FIG. 17). Furthermore, DNA fingerprinting test excluded the possibility that these hiPSCs arose from hESC contamination in the laboratory (Table 6). To examine the developmental potential of these hiPSC-O cells, they were differentiated in vitro by the standard embryoid body (EB) differentiation method. ICC analyses demonstrated that they could effectively differentiate into βIII-tubulin$^+$ characteristic neuronal cells (ectoderm), SMA$^+$ mesodermal cells, and AFP$^+$ endodermal cells (FIGS. 9d and 10e). Quantitative PCR analyses further confirmed the expression of these and additional lineage specific marker genes, including ectodermal cells (βIII-tubulin and NESTIN), mesodermal cells (MSX1 and MLC2a), and endodermal cells (FOXA2 and AFP) (FIG. 9e). Following EB protocol, these hiPSC-OK and hiPSC-O cells could also give rise to rhythmically beating cardiomyocytes. To test their in vivo pluripotency, they were transplanted into SCID mice. Four-six weeks later, these hiPSC-O cells effectively generated typical teratomas containing derivatives of all three germ layers (FIGS. 9f and 10f). Collectively, these in vitro and in vivo characterizations demonstrated that a single transcription factor, OCT4, combined with a defined small molecule cocktail is sufficient to reprogram several human primary somatic cells to iPSCs that are morphologically, molecularly and functionally similar to pluripotent hESCs.

The studies presented above have a number of important implications: (1) Although fetal NSCs were shown to be reprogrammed to iPSCs by ectopic expression of Oct4 alone, there have been significant skepticisms around whether exogenous Oct4 gene alone would be sufficient to reprogram other more practical human somatic cells that do not endogenously express Sox2 (one of the two master pluripotency genes in reprogramming), are at later developmental stages (e.g. early embryonic/fetal vs. born/adult), and can be obtained without significant harms to the individual. To our knowledge, our study is the first demonstration that iPSCs can be practically derived from readily available primary human somatic cells (e.g. keratinocytes) transduced with a single exogenous reprogramming gene, Oct4. In contrast to neural stem cells from the brain, keratinocytes are more accessible and can be easily obtained from born individuals with less invasive procedures. This further strengthens the strategy of exploiting various practically accessible human somatic cells for iPSC generation with safer approaches and/or better qualities. Thus, this new method and its further development would significantly facilitate production of patient-specific pluripotent stem cells for various applications. (2) Although small molecules and their combinations have been identified to replace only one or two reprogramming TFs, it becomes exponentially challenging to generate iPSCs when more exogenous reprogramming TFs are omitted together. The identification of this new small molecule cocktail, which functionally replaces three master transcription factors all together (i.e. Sox2, Klf4 and cMyc) in enabling generation of iPSCs with Oct4 alone, represents another major step toward the ultimate reprogramming with only small molecules, and further proved and solidified the chemical approach to iPSCs. (3) This demonstrated single gene condition also has a significant implication for protein-induced pluripotent stem cell (piPSC) technology. A practical challenge for piPSC technology is large-scale and reliable production of the four transducible reprogramming proteins, each of which behaves differently in manufacture (e.g. their expression, folding, stability etc.). Clearly, combining this small molecule cocktail with a single transducible protein would significantly simplify the piPSC technology and facilitate its applications. (4) More significantly, we identified a new small molecule, PS48, with a new target/mechanism in enhancing reprogramming. PS48 is an allosteric small molecule activator of PDK1, which is an important upstream kinase for several AGC kinases, including Akt/PKB (Alessi et al., *Curr Biol* 7, 261-269 (1997)). Its reprogramming enhancing effect may be partly attributed to the activation of Akt/PKB, which promotes cell proliferation and survival (Manning, B. D., Cantley, L. C., *Cell* 129, 1261-1274 (2007)). Further in-depth characterizations on how PDK1-involved mechanisms are precisely regulated during reprogramming process should provide additional insights underlying reprogramming and pluripotency. Furthermore, because there might be even greater hidden risks (e.g. more subtle genetic and/or epigenetic abnormalities could be generated or selected during the reprogramming process) imposed by the low efficiency and slow kinetics of reprogramming, identification of new small molecules for enhancing reprogramming as illustrated again in this study would always be highly valuable toward a safer, easier and more efficient procedure for human iPSC generation. (5) Finally, this new and powerful small molecule cocktail for reprogramming validated the step-wise chemical optimization and screening strategy presented here as a productive approach toward the ultimate purely chemical-induced pluripotent stem cells. Moreover, the finding that different small molecules modulating the same target/mechanism could have significantly different effects on reprogramming in a different context, exemplified by A-83-01's and NaB's better reprogramming enhancing activities in human keratinocytes, suggests the importance of "individualized" optimization and treatment with different regimens for specific reprogramming context.

Cell Culture

Normal Human Epidermal Keratinocytes (Lonza) were maintained in Keratinocyte culturing medium (KCM, Lonza). Human Umbilical Vein Endothelial Cells (HU-VECs, Millipore) were maintained in EndoGRO-VEGF Complete Medium (HCM, CHEMICON). Human ESCs and hiPSCs were cultured on MEF feeder cells in conventional human ESC culture media (hESCM: DMEM/F12, 15% Knockout serum replacement, 1% Glutamax, 1% Non-essential amino acids, 1% penicillin/streptomycin, 0.1 mM β-mercaptoethanol and 10 ng/ml bFGF). All cell culture products were from Invitrogen/Gibco BRL except where mentioned.

Lentivirus Production

The lentivirus supernatants were produced and harvested as previously described (Yu, J. et al., *Science* 318:1917-1920 (2007)). The plasmids used for lentivirus production include pSin-EF2-Puro-hOCT4, pSin2-EF2-Puro-hSOX2, pLove-mKlf4, pLove-mMyc, the packaging plasmid psPAX2 and the envelop-coding plasmid pMD2.G (Yu, J. et al., *Science* 318:1917-1920 (2007) and Li, W. et al., *Stem Cells* 27:2992-3000 (2009)).

Reprogramming of NHEKs

NHEKs were cultured in a 100 mm tissue culture dish and transduced 3 times (3-4 hours each transduction) with freshly produced lentivirus supernatants. 1,000,000 transduced NHEKs were seeded on the irradiated x-ray inactivated CF1 MEF feeder cells in a 100-mm dish and cultured in KCM and treated with 5 µM PS48, 0.25 mM NaB (Stemgent) and 0.5 µM A-83-01 (Stemgent) for 2 weeks, followed by changing half volume of media to hESCM and supplementing with 5 µM PS48, 0.25 mM NaB and 0.5 µM A-83-01 for another 2 weeks. Then cell culture media were changed to hESCM and supplemented with 5 µM PS48, 0.25 mM NaB, 0.5 µM A-83-01 and 0.5 µM PD0325901 (Stemgent) for additional four weeks. The same OCT4 infected keratinocytes cultured in media without chemicals were used as a control. The culture was split by Accutase (Millipore) and treated with 1 µM Thiazovivin (Stemgent) in the first day after splitting. The iPSC colonies stained positive by Alexa Fluor 555 Mouse anti-Human TRA-1-81 antibody (BD Pharmingen) were picked up for expansion on feeder cells in hESCM and cultured routinely.

Reprogramming of HUVECs

HUVECs were cultured in a 100 mm tissue culture dish and transduced 2 times (4-6 hours each transduction) with freshly produced lentivirus supernatants. 200,000 transduced HUVECs were seeded on gelatin coated 100-mm dish, cultured in HCM, and treated with 5 µM PS48, 0.25 mM NaB and 0.5 µM A-83-01 for 2 weeks, followed by changing half volume of media to hESCM and supplementing with 5 µM PS48, 0.25 mM NaB and 0.5 µM A-83-01 for another 2 weeks. Then cell culture media were changed to hESCM and supplemented with 5 µM PS48, 0.25 mM NaB, 0.5 µM A-83-01 and 0.5 µM PD0325901 for additional 1-2 weeks. The iPSC colonies stained positive by Alexa Fluor 555 Mouse anti-Human TRA-1-81 antibody were picked up for expansion on feeder cells in hESCM and cultured routinely. The culture was split by Accutase and treated with 1 µM Thiazovivin in the first day after splitting.

In Vitro Differentiation

The in vitro differentiation of hiPSCs was carried out by the standard embryoid body (EB) method. Briefly, the hiPSCs were dissociated by Accutase (Millipore), cultured in ultra-low attachment 6-well plate for eight days and then transferred to Matrigel-coated 6-well plate in differentiation medium. The cells were fixed for immunocytochemical analysis or harvested for RT-PCR tests eight days later. Differentiation medium: DMEM/F12, 10% FBS, 1% Glutamax, 1% Non-essential amino acids, 1% penicillin/streptomycin, 0.1 mM β-mercaptoethanol.

Alkaline Phosphatase Staining and Immunocytochemistry Assay

Alkaline Phosphatase staining was performed according to the manufacturer's protocol using the Alkaline Phosphatase Detection Kit (Stemgent). Standard immunocytochemistry assay was carried out as previously reported (Li, W. et al., *Stem Cells* 27:2992-3000 (2009)). Primary antibodies used can be found in the Table 3. Secondary antibodies were Alexa Fluor 488 donkey anti-mouse or anti-rabbit IgG (1:1000) (Invitrogen). Nuclei were visualized by DAPI (Sigma-Aldrich) staining. Images were captured using a Nikon Eclipse TE2000-U microscope.

Gene Expression Analysis by RT-PCR and qRT-PCR

For RT-PCR and qRT-PCR analysis, total RNA was extracted from human iPSCs using the RNeasy Plus Mini Kit in combination with QIAshredder (Qiagen). First strand reverse transcription was performed with 2 µg RNA using iScript™ cDNA Synthesis Kit (BioRad). The expression of pluripotency markers was analyzed by RT-PCR using Platinum PCR SuperMix (Invitrogen). The expression of lineage specific markers after differentiation was analyzed by qRT-PCR using iQ SYBR Green Supermix (Bio-Rad). The primers can be found in the Table 2.

Microarray Analysis

The Human Ref-8_v3 expression Beadchip (Illumina, Calif., USA) was used for microarray hybridizations to examine the global gene expression of NHEKs, hiPSC and hES cells. Biotin-16-UTP-labeled cRNA was synthesized from 500 ng total RNA with the Illumina TotalPrep RNA amplification kit (Ambion AMIL1791, Foster City, Calif., USA). The hybridization mix containing 750 ng of labeled amplified cRNA was prepared according to the Illumina BeadStation 500× System Manual (Illumina, San Diego, Calif., USA) using the supplied reagents and GE Healthcare Streptavidin-Cy3 staining solution. Hybridization to the Illumina Human Ref-8 v3 expression Beadchip was for 18 h at 55° C. on a BeadChip Hyb Wheel. The array was scanned using the Illumina BeadArray Reader. All samples were prepared in two biological replicates. Processing and analysis of the microarray data were performed with the Illumina BeadStudio software. The data were subtracted for background and normalized using the rank invariant option.

Bisulfate Genomic Sequencing

Genomic DNAs were isolated using the Non Organic DNA Isolation Kit (Millipore) and then treated with the EZ DNA Methylation-Gold Kit (Zymo Research Corp., Orange, Calif.). The treated DNAs were then used as templates to amplify sequences of interest. Primers used for OCT4 and NANOG promoter fragment amplification are indicated in Table 2. The resulting fragments were cloned using the TOPO TA Cloning Kit for sequencing (Invitrogen) and sequenced.

Genotyping of hiPSCs

Genotyping of hiPSC lines was performed using RT-PCR of genomic DNA with specific primers (Table 2; Yu, J. et al., *Science* 318:1917-1920 (2007) and Li, W. et al., *Stem Cells* 27:2992-3000 (2009)).

Teratoma Formation

The hiPSC lines were harvested by using 0.05% Trypsin-EDTA. Five million cells were injected under the kidney capsule of SCID mice (n=3). After 4-6 weeks, well developed teratomas were harvested, fixed and then histologically analyzed at TSRI histology core facility.

TABLE 2

Primers used

| Gene | Forward (SEQ ID NO:) | Reverse (SEQ ID NO:) |
|---|---|---|
| For RT-PCR | | |
| Endo-OCT4 | AGTTTGTGCCAGGGTTTTTG (1) | ACTTCACCTTCCCTCCAACC (2) |
| Endo-SOX2 | CAAAAATGGCCATGCAGGTT (3) | AGTTGGGATCGAACAAAAGCTATT (4) |
| Endo-NANOG | TTTGGAAGCTGCTGGGGAAG (5) | GATGGGAGGAGGGGAGAGGA (6) |
| Endo-KLF4 | ACGATCGTGGCCCCGGAAAAGGACC (7) | GATTGTAGTGCTTTCTGGCTGGGCTCC (8) |
| Endo-cMYC | GCGTCCTGGGAAGGGAGATCCGGAGC (9) | TTGAGGGGCATCGTCGCGGGAGGCTG (10) |
| REX1 | CAGATCCTAAACAGCTCGCAGAAT (11) | GCGTACGCAAATTAAAGTCCAGA (12) |
| UTF1 | CCGTCGCTGAACACCGCCCTGCTG (13) | CGCGCTGCCCAGAATGAAGCCCAC (14) |
| TDGF2 | CTGCTGCCTGAATGGGGGAACCTGC (15) | GCCACGAGGTGCTCATCCATCACAAGG (16) |
| FGF4 | CTACAACGCCTACGAGTCCTACA (17) | GTTGCACCAGAAAAGTCAGAGTTG (18) |
| Exo-OCT4 | TGTCTCCGTCACCACTCTGG (19) | ATGCATGCGGATCCTTCG (20) |
| PAX6 | TGTCCAACGGATGTGAGT (21) | TTTCCCAAGCAAAGATGGAC (22) |
| βIII TUBULIN | CAACAGCACGGCCATCCAGG (23) | CTTGGGGCCCTGGGCCTCCGA (24) |
| FOXF1 | AAAGGAGCCACGAAGCAAGC (25) | AGGCTGAAGCGAAGGAAGAGG (26) |
| HAND1 | TCCCTTTTCCGCTTGCTCTC (27) | CATCGCCTACCTGATGGACG (28) |
| AFP | AGCAGCTTGGTGGTGGATGA (29) | CCTGAGCTTGGCACAGATCCT (30) |
| GATA6 | TGTGCGTTCATGGAGAAGATCA (31) | TTTGATAAGAGACCTCATGAACCGACT (32) |
| GAPDH | GTGGACCTGACCTGCCGTCT (33) | GGAGGAGTGGGTGTCGCTGT (34) |
| For bisulfate-sequencing | | |
| OCT4-1 | TTAGGAAAATGGGTAGTAGGGATTT (35) | TACCCAAAAAACAAATAAATTATAAAACCT (36) |
| OCT4-2 | GGATGTTATTAAGATGAAGATAGTTGG (37) | CCTAAACTCCCCTTCAAAATCTATT (38) |
| NANOG | GAGTTAAAGAGTTTTGTTTTTAAAAATTAT (39) | TCCCAAATCTAATAATTTATCATATCTTTC (40) |
| For genotyping | | |
| OCT4-Int | CAGTGCCCGAAACCCACAC (41) | AGAGGAACTGCTTCCTTCACGACA (42) |
| SOX2-Int | TACCTCTTCCTCCCACTCCA (43) | AGAGGAACTGCTTCCTTCACGACA (44) |
| KLF-Int | CACCTTGCCTTACACATGAAGAGG (45) | CGTAGAATCGAGACCGAGGAGA (46) |

TABLE 3

Primary antibodies applied

| Antibody | Species | Dilution | Vendor |
|---|---|---|---|
| Anti-OCT4 (1) | Mouse | 1:500 | Santa Cruz Biotechnology |
| Anti-OCT4 (2) | Rabbit | 1:500 | Stemgent |
| Anti-SOX2 | Rabbit | 1:1000 | Chemicon |
| Anti-NANOG | Rabbit | 1:500 | Abcam |
| Anti-SSEA4 | Mouse | 1:500 | Stemgent |
| Anti-TRA-1-81 | Mouse | 1:500 | Stemgent |
| TUJ1 (Anti-βIII TUBULIN) | Mouse | 1:3000 | Covance Research Products |
| Anti-SMA | Mouse | 1:500 | Sigma |
| Anti-AFP | Mouse | 1:500 | Sigma |

TABLE 4

Summary of reprogramming experiments

| Donor Cells | Induction factors | Chemicals | Experiments | TRA-1-81 positive colonies |
|---|---|---|---|---|
| NHEKs (lot number: 0000087940) | OCT4 + KLF4 + SOX2 + MYC | DMSO | #1 | 17 |
| | | | #2 | 20 |
| | | | #3 | 23 |
| | | A83 + PD | #1 | 72 |
| | | | #2 | 104 |
| | | | #3 | 91 |
| | OCT4 + KLF4 + SOX2 | DMSO | #1 | 2 |
| | | | #2 | 3 |
| | | | #3 | 8 |
| | | A83 + PD | #1 | 26 |
| | | | #2 | 35 |
| | | | #3 | 44 |
| | | A83 + PD | #1 | 1 |
| | | | #2 | 2 |
| | | | #3 | 0 |

TABLE 4-continued

Summary of reprogramming experiments

| Donor Cells | Induction factors | Chemicals | Experiments | TRA-1-81 positive colonies |
|---|---|---|---|---|
| | | A83 + PS48 + PD | #1 | 15 |
| | | | #2 | 18 |
| | | | #3 | 5 |
| | OCT4 + KLF4 | A83 + VPA + PD | #1 | 6 |
| | | | #2 | 0 |
| | | | #3 | 3 |
| | | A83 + NaB + PD | #1 | 20 |
| | | | #2 | 17 |
| | | | #3 | 18 |
| | | A83 + PS48 + NaB + PD | #1 | 21 |
| | | | #2 | 30 |
| | | | #3 | 27 |
| | OCT4 | A83 + PS48 + NaB + PD | #1 | 4 |
| | | | #2 | 0 |
| | | | #3 | 3 |
| NHEKs (lot number: 2F0661) | OCT4 | A83 + PS48 + NaB + PD | #1 | 2 |
| | | | #2 | 3 |
| | | | #3 | 0 |
| AHEKs | OCT4 | A83 + PS48 + NaB + PD + Par + CHIR | #1 | 3 |
| | | | #2 | 2 |
| HUVECs | OCT4 | A83 + PS48 + NaB + PD | #1 | 4 |
| | | | #2 | 7 |
| | | | #3 | 4 |
| HUVECs | OCT4 | A83 + PS48 + NaB + PD + Par + CHIR | #1 | 23 |
| | | | #2 | 17 |
| AFDCs | OCT4 | A83 + PS48 + NaB + PD + Par + CHIR | #1 | 5 |
| | | | #2 | 11 |

NHEKs, Neonatal Human Epidermal Keratinocytes; HUVECs, Human Umbilical Vein Endothelial Cells; AHEKs, Adult Human Epidermal Keratinocytes; AFDCs, Amniotic Fluid Derived Cells. Chemical concentration used: PD, 0.5 μM PD0325901; A83, 0.5 μM A-83-01; PS48, 5 μM PS48; VPA, 0.5 mM Valproic acid; NaB, 0.25 mM Sodium butyrate; Par, 2 μM Parnate; CHIR, 3 μM CHIR99021. For four-factor or three-factor induced reprogramming, NHEKs were seeded at a density of 100,000 transduced cells per 10 cm dish and positive colonies were counted four-week later; For two-factor induced reprogramming, NHEKs were seeded at a density of 100,000 transduced cells per 10 cm dish and positive colonies were counted six-week later; For one-factor induced reprogramming, NHEKs and AHEKs were seeded at a density of 1,000,000 transduced cells per 10 cm dish and positive colonies were counted eight-week later; HUVECs and AFDCs were seeded at a density of 200,000 transduced cells per 10 cm dish and positive colonies were counted six-week later.

TABLE 5

Characterization of established human iPSC cell lines

| hiPSC clone | Induction factors | Cell source | Marker expression | RT-PCR test | EB differentiation | Teratoma test |
|---|---|---|---|---|---|---|
| hiPSC-OK#1 | OCT4 + KLF4 | NHEKs | ✓ | ✓ | ✓ | ✓ |
| hiPSC-OK#3 | | | ✓ | ✓ | ✓ | |
| hiPSC-O#1 | OCT4 | NHEKs | ✓ | ✓ | ✓ | ✓ |
| hiPSC-O#3 | | | ✓ | ✓ | ✓ | |
| hiPSC-O#4 | | | ✓ | | | |
| hiPSC-O#5 | | | ✓ | | | |
| 2 more lines | | | | | | |
| hiPSC-O#21 | OCT4 | HUVECs | ✓ | ✓ | ✓ | ✓ |
| hiPSC-P#22 | | | ✓ | | | |
| hiPSC-O#26 | | | ✓ | ✓ | ✓ | |
| hiPSC-O#31 | | | ✓ | ✓ | ✓ | ✓ |
| 7 more lines | | | | | | |
| hiPSC-O#52 | OCT4 | AHEKs | ✓ | | ✓ | |
| hiPSC-O#57 | | | ✓ | | | |
| hiPSC-O#63 | OCT4 | AFDCs | ✓ | | ✓ | |
| hiPSC-O#65 | | | ✓ | | | |

Those cell lines characterized were long-term expanded for over 20 passages under conventional hESC culture condition and further characterized for marker expression and pluripotency; while other cell lines established were stored at passage 5 or 6. Blank entries indicate not determined.

TABLE 6

DNA fingerprint analysis on Oct4 induced iPSCs and parental cell lines

| Genomic loci | NHEK (pooled) | hiPSC-O#1 | HUVEC | hiPSC-O#21 |
|---|---|---|---|---|
| Amelogenin | X, Y | X, Y | X | X |
| vWA | 11, 15, 17, 18, 19 | 15, 18 | 15; 16 | 15; 16 |
| D8S1179 | 10, 13, 16 | 13, | 10; 13 | 10; 13 |
| TPOX | 8, 9, 11, 12 | 8 | 8 | 8 |
| FGA | 19, 22, 23, 24 | 19, 22 | 24; 27 | 24; 27 |
| D3S1358 | 13, 14, 15, 17 | 17 | 14; 16 | 14; 16 |
| THO1 | 6, 7, 9, 9.3 | 7, 9 | 6 | 6 |
| D21S11 | 24.2, 29, 30.2, 35 | 24.2, 29 | 28; 30.2 | 28; 30.2 |
| D18S51 | 13, 14, 16, 17, 18, 19 | 13, 17 | 13; 18 | 13; 18 |
| Penta E | 5, 8, 13, 14, 19 | 13, 19 | 12 | 12 |
| D5S818 | 8, 11, 12, 13 | 11, 13 | 12; 13 | 12; 13 |
| D13S317 | 8, 9, 11, 12, 13 | 9, 12 | 11; 14 | 11; 14 |
| D7S820 | 8, 9, 10, 11 | 9, 10 | 11 | 11 |
| D16S539 | 9, 10, 11, 12, 13 | 9, 13 | 9; 11 | 9; 11 |
| CSF1PO | 10, 11, 12 | 11, 12 | 11; 12 | 11; 12 |
| Penta D | 2.2, 10, 12 | 10 | 12; 13 | 12; 13 |

Fifteen polymorphic short tandem repeat (STR) DNA loci and the sex chromosome marker amelogenin were investigated.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inducing non-pluripotent mammalian cells into induced pluripotent stem cells, comprising:
   (a) introducing Oct-3/4, and optionally, one or both of Klf and Sox2, into the non-pluripotent cells; and
   (b) contacting the non-pluripotent cells with a mixture comprising an ALK5 inhibitor, a MEK inhibitor, and a ROCK inhibitor, wherein the ALK5 inhibitor, the MEK inhibitor, and the ROCK inhibitor increase efficiency of inducing the non-pluripotent mammalian cells into induced pluripotent stem cells, as compared to non-pluripotent mammalian cells treated with the ALK5 inhibitor and the MEK inhibitor without the ROCK inhibitor.

2. The method of claim 1, wherein the introducing step comprises introducing a polynucleotide encoding Oct-3/4, and optionally, one or both of Klf and Sox2 operably linked to a regulatory sequence into the non-pluripotent cells, wherein the polynucleotide is expressed in the non-pluripotent cells.

3. The method of claim 1, wherein the introducing step comprises contacting the non-pluripotent cells with Oct-3/4, Klf, Sox2, and optionally c-Myc polypeptides.

4. The method of claim 1, further comprising contacting the non-pluripotent cells with a glycogen synthase kinase 3 (GSK3) inhibitor.

5. The method of claim 1, further comprising contacting the non-pluripotent cells with a histone deacetylase (HDAC) inhibitor.

6. The method of claim 1, wherein the mammalian cells are human cells.

* * * * *